US011135341B2

(12) United States Patent
Lynch et al.

(10) Patent No.: US 11,135,341 B2
(45) Date of Patent: Oct. 5, 2021

(54) PLATELET-DERIVED GROWTH FACTOR COMPOSITION AND METHODS FOR THE TREATMENT OF TENDON AND LIGAMENT INJURIES

(71) Applicant: BioMimetic Therapeutics, LLC, Franklin, TN (US)

(72) Inventors: Samuel E. Lynch, Franklin, TN (US); Leslie Wisner-Lynch, Franklin, TN (US); Hans K. Kestler, Brentwood, TN (US); Yanchun Liu, Franklin, TN (US)

(73) Assignee: BioMimetic Therapeutics, LLC, Franklin, TN (US)

( * ) Notice: Subject to any disclaimer, the term of this patent is extended or adjusted under 35 U.S.C. 154(b) by 0 days.

(21) Appl. No.: 16/537,353

(22) Filed: Aug. 9, 2019

(65) Prior Publication Data

US 2020/0139013 A1 May 7, 2020

Related U.S. Application Data

(63) Continuation of application No. 14/500,354, filed on Sep. 29, 2014, now Pat. No. 10,556,039, which is a
(Continued)

(51) Int. Cl.
*A61L 27/54* (2006.01)
*A61L 27/24* (2006.01)
(Continued)

(52) U.S. Cl.
CPC .............. *A61L 27/54* (2013.01); *A61L 27/24* (2013.01); *A61L 27/26* (2013.01); *A61L 27/56* (2013.01);
(Continued)

(58) Field of Classification Search
CPC .............. A61F 2/08; A61F 2/00; A61K 38/18
USPC ....................... 623/13.11–13.2, 14.12, 14.13, 623/23.61–23.63, 23.72–23.76; 424/93.7, 424/42, 63, 426; 514/7.6–8.2
See application file for complete search history.

(56) References Cited

U.S. PATENT DOCUMENTS 3,943,072 A  3/1976  Thomson et al.
4,845,075 A  7/1989  Murray et al.
(Continued)

FOREIGN PATENT DOCUMENTS

EP   0 289 584 B1   11/1988
EP   0 479 799 B1   4/1992
(Continued)

OTHER PUBLICATIONS

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware% . . . >, last visited on Feb. 24, 2010, 2 pages.
(Continued)

*Primary Examiner* — Yashita Sharma
(74) *Attorney, Agent, or Firm* — Foley Hoag LLP; Hilary Dorr Lang

(57) ABSTRACT

The invention provides compositions and methods for treatment of tendon and ligament injuries and/or repair of damaged tendons and ligament. The invention provides compositions comprising a biocompatible matrix and platelet-derived growth factor (PDGF).

34 Claims, 19 Drawing Sheets

Related U.S. Application Data continuation of application No. 12/556,555, filed on Sep. 9, 2009, now Pat. No. 8,870,954, which is a continuation-in-part of application No. PCT/US2009/056418, filed on Sep. 9, 2009.

(60) Provisional application No. 61/191,641, filed on Sep. 9, 2008, provisional application No. 61/144,126, filed on Jan. 12, 2009, provisional application No. 61/144,088, filed on Jan. 12, 2009.

(51) Int. Cl.
    *A61L 27/58*     (2006.01)
    *A61L 27/56*     (2006.01)
    *A61L 27/26*     (2006.01)

(52) U.S. Cl.
    CPC ......... *A61L 27/58* (2013.01); *A61L 2300/414* (2013.01); *A61L 2300/602* (2013.01); *A61L 2430/10* (2013.01)

(56) References Cited

U.S. PATENT DOCUMENTS

| | | |
|---|---|---|
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,376,636 A | 12/1994 | Rutherford et al. |
| 5,418,222 A | 5/1995 | Song et al. |
| 5,457,093 A | 10/1995 | Cini et al. |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,783,217 A | 7/1998 | Lee et al. |
| 5,804,176 A | 9/1998 | Grotendorst |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 7,799,754 B2 | 9/2010 | Hart et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0123805 A1 | 9/2002 | Murray et al. |
| 2002/0127265 A1 | 9/2002 | Bowman et al. |
| 2002/0131989 A1 | 9/2002 | Brown et al. |
| 2002/0193883 A1 | 12/2002 | Wironen |

(56) References Cited

U.S. PATENT DOCUMENTS

| | | |
|---|---|---|
| 2003/0006025 A1 | 1/2003 | Manini et al. |
| 2003/0021827 A1 | 1/2003 | Malaviya et al. |
| 2003/0049328 A1 | 3/2003 | Dalal et al. |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1 | 1/2004 | Garrett |
| 2004/0022825 A1 | 2/2004 | Lagow |
| 2004/0033949 A1 | 2/2004 | Bunting et al. |
| 2004/0037813 A1 | 2/2004 | Simpson et al. |
| 2004/0043031 A1 | 3/2004 | Hart et al. |
| 2004/0059416 A1 | 3/2004 | Murray et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0260326 A1 | 11/2007 | Williams et al. |
| 2007/0232455 A1 | 12/2007 | Luginbuehl et al. |
| 2008/0027470 A1 | 1/2008 | Hart et al. |
| 2008/0317816 A1 | 12/2008 | Ma et al. |
| 2009/0092674 A1 | 4/2009 | Ingram et al. |
| 2009/0130173 A1 | 5/2009 | Behnam et al. |
| 2009/0254104 A1 | 10/2009 | Murray |

FOREIGN PATENT DOCUMENTS

| | | |
|---|---|---|
| EP | 0 530 804 A1 | 3/1993 |
| EP | 0 530 804 B1 | 3/1993 |
| EP | 0 741 785 B1 | 11/1996 |
| EP | 0 741 785 B2 | 11/1996 |
| EP | 0 896 825 A1 | 2/1999 |
| EP | 0 896 825 B1 | 2/1999 |
| EP | 0 994 694 B1 | 4/2000 |
| EP | 1 025 871 A1 | 8/2000 |
| EP | 1 100 488 B1 | 5/2001 |
| EP | 1 146 897 B1 | 10/2001 |
| EP | 1 234 552 A1 | 8/2002 |
| EP | 1 234 552 B1 | 8/2002 |
| EP | 1 242 129 B1 | 9/2002 |
| EP | 1 374 857 A1 | 1/2004 |
| EP | 1 410 811 A1 | 4/2004 |
| EP | 1 410 811 B1 | 4/2004 |
| EP | 1 464 307 A1 | 10/2004 |
| EP | 1 464 307 B1 | 10/2004 |
| EP | 1 561 481 A2 | 8/2005 |
| EP | 1 561 481 A3 | 8/2005 |
| EP | 1 563 846 A1 | 8/2005 |
| EP | 1 681 087 A2 | 7/2006 |
| EP | 1 681 087 A3 | 7/2006 |
| EP | 1 712 244 A1 | 10/2006 |
| EP | 1 719 531 A2 | 11/2006 |
| EP | 1 719 532 A2 | 11/2006 |
| GB | 2 367 497 A | 4/2002 |
| JP | 7-250688 A | 10/1995 |
| JP | 2003-265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO 94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/16035 A3 | 6/1995 |
| WO | WO-95/18856 A1 | 7/1995 |
| WO | WO-95/20967 A1 | 8/1995 |
| WO | WO-95/28124 A2 | 10/1995 |
| WO | WO-95/28124 A3 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-96/17924 A3 | 6/1996 |
| WO | WO-97/13857 A1 | 4/1997 |
| WO | WO-98/00183 A2 | 1/1998 |
| WO | WO-98/00183 A3 | 1/1998 |
| WO | WO-93/40113 A1 | 9/1998 |
| WO | WO-98/41246 A2 | 9/1998 |
| WO | WO-98/41246 A3 | 9/1998 |

(56) References Cited

FOREIGN PATENT DOCUMENTS

| | | |
|---|---|---|
| WO | WO-98/51354 A2 | 11/1998 |
| WO | WO-98/51354 A3 | 11/1998 |
| WO | WO-99/30726 A1 | 6/1999 |
| WO | WO-99/38543 A2 | 8/1999 |
| WO | WO-99/38543 A3 | 8/1999 |
| WO | WO-99/67289 A1 | 12/1999 |
| WO | WO-00/04940 A1 | 2/2000 |
| WO | WO-01/32197 A2 | 5/2001 |
| WO | WO-01/32197 A3 | 5/2001 |
| WO | WO-01/35932 A2 | 5/2001 |
| WO | WO-01/35932 A3 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/60424 A3 | 8/2001 |
| WO | WO-01/66044 A2 | 9/2001 |
| WO | WO-01/66044 A3 | 9/2001 |
| WO | WO-01/66130 A1 | 9/2001 |
| WO | WO-01/68135 A2 | 9/2001 |
| WO | WO-01/68135 A3 | 9/2001 |
| WO | WO-02/00244 A2 | 1/2002 |
| WO | WO-02/00244 A3 | 1/2002 |
| WO | WO-02/00272 A2 | 1/2002 |
| WO | WO-02/00272 A3 | 1/2002 |
| WO | WO-02/36147 A1 | 5/2002 |
| WO | WO-02/062405 A2 | 8/2002 |
| WO | WO-02/062405 A3 | 8/2002 |
| WO | WO-02/067978 A1 | 9/2002 |
| WO | WO-02/070029 A2 | 9/2002 |
| WO | WO-02/070029 A3 | 9/2002 |
| WO | WO-02/102783 A1 | 12/2002 |
| WO | WO-03/006025 A1 | 1/2003 |
| WO | WO-03/043576 A2 | 5/2003 |
| WO | WO-03/043576 A3 | 5/2003 |
| WO | WO-03/065996 A2 | 8/2003 |
| WO | WO-03/065996 A3 | 8/2003 |
| WO | WO-03/070186 A2 | 8/2003 |
| WO | WO-03/070186 A3 | 8/2003 |
| WO | WO-03/071997 A1 | 9/2003 |
| WO | WO-2004/002539 A2 | 1/2004 |
| WO | WO-2004/002539 A3 | 1/2004 |
| WO | WO-2004/002539 C1 | 1/2004 |
| WO | WO-2004/010907 A1 | 2/2004 |
| WO | WO-2004/071543 A1 | 8/2004 |
| WO | WO-2004/073563 A2 | 9/2004 |
| WO | WO-2004/073563 A3 | 9/2004 |
| WO | WO-2004/110308 A2 | 12/2004 |
| WO | WO-2004/110308 A3 | 12/2004 |
| WO | WO-2004/110308 C2 | 12/2004 |
| WO | WO-2005/009496 A1 | 2/2005 |
| WO | WO-2005/032461 A2 | 4/2005 |
| WO | WO-2005/032461 A3 | 4/2005 |
| WO | WO-2005/042048 A2 | 5/2005 |
| WO | WO-2005/042048 A3 | 5/2005 |
| WO | WO-2005/046746 A2 | 5/2005 |
| WO | WO-2005/054279 A1 | 6/2005 |
| WO | WO-2005/054279 C1 | 6/2005 |
| WO | WO-2005/072656 A1 | 8/2005 |
| WO | WO-2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO 2006/044334 | 4/2006 |
| WO | WO-2006/050493 A2 | 5/2006 |
| WO | WO-2006/050493 A3 | 5/2006 |
| WO | WO-2006/093808 A1 | 9/2006 |
| WO | WO-2006/133403 A2 | 12/2006 |
| WO | WO-2006/133403 A3 | 12/2006 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO 2007092622 | 8/2007 |
| WO | WO 2008/005427 | 1/2008 |

OTHER PUBLICATIONS

Adalberto et al. "Periodontal Regeneration," *J. Periodontal*, 2005, 76(9):1601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7):971-977.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H, et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Master's Abstracts International* 46(6):61.

American Dental Association (Jun. 2006). *Expert Panel Recommendations: Dental Management of Patients on Oral Bisphosphonate Therapy*, Report of the Council of Scientific Affairs, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res.* 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-756.

Anusaksathien et al. "Effect of Sustained Gene Delivery of Platelet-Derived Growth Factor or its Antagonist (PDGF-1308) on Tissue-Engineered Cementum," *J. Periodontal*, Mar. 2004, 75(3):429-440.

Arm, D.M. et al. "Effect of Controlled Release of Platelet-derived Growth Factor from a Porous Hydroxyapatite Implant on Bone Ingrowth," *Biomaterials*, 1996, 17(7):703-709.

Assael, L.A. (2006). "A Time for Perspective on Bisphosphonates," *J. Oral Maxiliofac. Surg.* 64:877-879.

Babbush, C.A. DDS MSCD et al. "An In Vitro and In Vivo Evaluation of Autologous Platelet Concentrate in Oral Reconstruction," *Implant Dent.*, 2003, 12(1):24-34.

Barker, K. et al. (Jun. 2005). "Bisphosphonate-Associated Osteonecrosis of the Jaws: A Guide for the General Dental Practitioner," *Dental Update* pp. 270-275.

Rasa, S. et al. (2004). "Alternative Bono Expansion Technique for Immediate Placement of Implants in the Edentulous Posterior Mandibular Ridge: A Clinical Report," *International Journal of Oral & Maxofacial Implants* 19(4):554-558.

(56) References Cited

OTHER PUBLICATIONS

Bateman, J. et al. "Platelet-Derived Growth Factor Enhancement of Two Alloplastic Bone Matrices," *J. Periodontal.* (Nov. 2005) 76(11):1833-1841.

Becker. W. et al. (Nov. 1992). "A Comparison of ePTFE Membranes Alone or in Combination with Platelet-Derived Growth Factor and Insulin-Like Growth Factor-I, or Demineraiized Freeze Dried Bone in Promoting Bone Formation Around Immediate Extraction Socket Implants: A Study in Dogs," *J. Periodtonol.* 63(11):929-940.

Berlemann, U. et al. (2002). "Adjacent Vertebral Failure After Vertebroplasty," *J. Bone Joint Surg. BR* 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedti.htm&StoryID=76&>, last visited on May 18, 2010, 5 pages.

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.

Biomimetic Therapeutics (Jul. 15, 2004). "BioMimetic Pharmaceuticals' Receives Approvable Recommendation from FDA Advisory Panel for GEM 21S®," located at <http://biomimetics.com/cgi-bin/aw/acuweb.cgi?s=biomimetics&t=pressreleasedtl,htm&StoryID=73&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressreleasedtl.htm&StoryID=79&>, last visited on May 20, 2010, 5 pages.

Biomimetic Therapeutics (May 18, 2005). "Biomimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.

Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasetl.htm&StoryID=81&>, last visited on May 20, 2010, 6 pages.

Biomimetic Therapeutics (Nov. 21, 2005). "BioMimetic Therapeutics Announces FDA Approval of GEM 21S® Growth-Factor Enhanced Matrix for the Treatment of Periodontally-Related Bone Detects," located at <http://biomimetics.com/cgi-bin/acuweb.cgi?s=biomimetics&t=pressreleasedtl.htm&StoryID=87&>, last visited on May 18, 2010, 6 pages.

Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.

Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&1=NewsDetail.htm&StoryID=166&>, 5 pages.

Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.

Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics&t=pressreleasedtl.htm&StoryID=94&>, last visited on May 13, 2010, 6 pages.

Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressreleasedtl.htm&StoryID=97&>, last visited on May 20, 2010, 6 pages.

Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101&>, last visited on May 18, 2010, 7 pages.

Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedti.htm&StoryID=104&>, last visited on May 13, 2010, 7 pages.

Biomimetic Therapeutics (Jan. 25, 2007). "BioMimetic Therapeutics Reports Positive Clinical Results Using GEM OS® 1 to Treat Distal Radius Fractures," located at <http://biomimetics.com/cgi-bin/aw/acuweb.cgi?s=biomimetics&t=pressreleasedtl.htm&StoryID=105&>, last visited on May 18, 2010, 6 pages.

Biomimetic Therapeutics (Feb. 21, 2007). "BioMimetic Therapeutics Receives Orphan Drug Designation for rhPDGF-BB Treatment of Osteonecrosis of the Jaw," located at <http://biomimetics.com/cgi-bin/aw/acuweb.cgi?s=biomimetics&t=pressreleasedtl.htm&StoryID=112&>, last visited on Apr. 5, 2010, 6 pages.

Biomimetic Therapeutics (Mar. 28. 2007). "BioMimetic Therapeutics Reports 2006 Fourth Quarter and Year-End Results; Company Receives Clearance to Initiate Enrollment in GEM OS1 US Pivotal Trial," located at <http://blomimetics.com/cgi-bin/aw/acuweb.cgi?s=biomimetics&t=pressreleasedtl.htm&StoryID=113&>, last visited on May 18, 2010, 8 pages.

Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.

Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm&StoryID=116&>, last visited on May 18, 2010, 7 pages.

Biomimetic Therapeutics (Jun. 7, 2007). "BioMimetic Therapeutics Initiates Enrollment in E.U. Registration Trial for GEM Os®1 Bone Graft; U.S, GEM OS1 Pivotal Study Protocol Amended to Allow Shorter Follow-Up Time and More Patients," located at <http://biomimetics.com/cgi-bin/aw/acuweb.cgi?s=biomimetics&t=pressreleasedtl.htm&StoryID=119&>, last visited on May 13, 2010, 6 pages.

Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics&t=pressreleasedtl.htm&StoryID=123&>, last visited on May 18, 2010, 3 pages.

Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressreleasedtl.htm&StoryID=125&>, last visited on May 18, 2010, 7 pages.

Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressreleasedtl.htm&StoryID=127&>, last visited on May 18, 2010, 7 pages.

(56) References Cited

OTHER PUBLICATIONS

Biomimetic Therapeutics (Dec. 13, 2007). "BioMimetic Therapeutics reports Positive Clinical Results for GEM OS®1 in Canadian Foot and Ankle Fusion Study; Clinical Success Rate of 90% Achieved in High Risk Patient Population," located at <http://biomimetics.com/cgi-bin/aw/acuweb.cgi?s=biomimetics&t=pressreleasedtl.htm&StoryID=131&>, last visited on May 18, 2010, 6 pages.

Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm&StoryID=149&>, last visited on May 18, 2010, 7 pages.

Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136&>, last visited on May 18, 2010, 6 pages.

Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.

Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.

Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&Story ID=151&>, last visited on May 18, 2010, 8 pages.

Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&Story ID=153&>, last visited on May 18, 2010, 7 pages.

Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.

Biomimetic Therapeutics (Nov. 10, 2008). "BioMimetic Therapeutics Reports 2008 Third Quarter Results," located at at <http://biomimetics.com/cgi-bin/aw/acuweb.cgi?s=biomimetics&t=pressreleasedtl.htm&StoryID=157&>, last visited on May 18, 2010, 3 pages.

Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.

Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.

Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.

Biomimetic Therapeutics (Feb. 19, 2009). "BicMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.

Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.

Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.

Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.

Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at < http://biomimetics.com/cgi-bin/aw/acuweb.cgi?s=biomimetics&t=pressreleasedtl.htm&StoryID=188&>, last visited on May 18, 2010, 8 pages.

Biomimetic Therapeutics (Nov. 3, 2009). "BioMimetic Therapeutics Receives First Orthopedic Marketing Approval for Augment Bone Graft," located at <http://biomimetics.com/cai-bin/aw/acuweb.cgi?s=biomimetics&t=pressreleasedtl.htm&StoryID=190&>, last visited on May 18, 2010, 6 pages.

Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm&StoryID=191&>, last visited on May 18, 2010, 8 pages.

Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 13, 2010, 5 pages.

Biomimetic Therapeutics (Mar. 4, 2010). "BioMimetic Therapeutics, Inc. to Highlight Pre-Ciinical and Ciinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.

Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.

Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.

Biomimetic Therapeutics (Mar. 12, 2010). "Morningstar® Document ResearchSM Form 10-K," United States Securities and Exchange Commission Annual Report, located at <http://investor.biomimetics.com/phoenix.zhtml?c=196896&p=irol-sec>, last visited on May 19, 2010, 247 pages.

(56) References Cited

OTHER PUBLICATIONS

Björkenheim, J-M. (1989). "Structure and Function of the Rabbit's Supraspinatus Muscle After Resection of its Tendon," *Acta Orthop. Scand.* 60(4):461-463.

Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.

Bolander, "Regulation of Fracture Repair by Growth Factors," *P.S.E.B.M.*, 1992, 200:165-170.

Bonfini, T. et al. (Jan. 1, 2006). "Autologous Marrow and Platel Gel in Bone Tissue Regeneration," *Cytotherapy* 8(1), Abstract No. 239, 2 pages.

Bora, F.W. Jr. et al. (Aug. 1987). "Joint Physiology, Cartilage Metabolism, and the Etiology of Osteoarthritis," *Hand Clin.* 3(3):325-336.

Boyden, E.M. et al. (Aug. 1995). "Late Versus Early Repair of Achilles Tendon Rupture: Clinical and Biomechanical Evaluation," *Clin. Orthop. Relat. Res.* 317:150-158.

Braddock, M. et al. (Oct. 2001). "Born Again Bone: Tissue Engineering for Bone Repair," *News Physiool. Sci.* 16:208-213.

Buser, D. et al. (1991). "Effects of Growth Factors on Bone Regeneration Around Titanium Implants," Abstract No. 282, *J. Dental Res.* 70:301.

Business Wire (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/1G1-68027113.html>, last visited on Apr. 26, 2010, 3 pages.

Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3 pages.

Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry*. 2001, 21(2):109-120.

Camelo, M. et al. (Nov. 3, 2003). "Periodontal Regeneration in Human Class II Furcations Using Purified Recombinant Human Platelet-Derived Growth Factor-Bb (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol.* 71(1):1743-1749.

Catalano, L. et al. (2006). "Bisphoshonates and Risk cf Osteonecorisis of the Jaws," *Haema* 9(3):410-414.

Cenni. E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.

Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.

Chalmers, J. (Jun. 2000). "Review Article: Treatment of Achilles Tendon Ruptures," *J. Orthop. Surg.* 8(1):97-99.

Chan, B.P. et al. (Jul. 2006). "Supplementation-time Dependence of Growth Factors in Promoting Tendon Healing," *Clinical Orthopaedics and Related Research* 448:240-247.

Chen et al. "Adenoviral Gene Transfer of PDGF Downregulates Gas Gene Product PDGFR and Prolongs ERK and AktIPKB Activation," *Am J Physiol Cell Physiol.*, Mar. 2002, 232:C538-C544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.

Cho et al. (Jun. 1995). "Platelet Derived Growth Factor—Modulated Guided Tissue Regenerative Therapy," *J. Peridontol.* 66(6):522-530.

Clain, M.R. et al. (Oct. 1992). "Achilles Tendinitis," *Foot Ankle Int.* 13(8):482-487.

Clergeau, L.P. et al. (Feb. 1996). "Healing Response to Anorganic Bone Implantation in Periodontal Intrabony Defects in Dogs Part 1, Bone Regeneration. A Microradiographic Study," *J. Periodontool.* 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res.* 82:253-262.

Cooke et al. "Effect of rhPDGR-BB Delivery on Mediators of Periodontal Wound Repair," *Tissue Engineering*, 2006, 12(6):1441-1450.

Cossolin, G.S.I. et al. ( Date Unknown) "Treatment of Avascular Osteonecrosis of the Jaws in Cancer Patients with a Histroy of Bisphosphonate Therapy by Combining Bone Resection and Autologous Platelet-Rich Plasma," *Hospital Santa Catarina* 10 pages.

Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.

Courneya, J-P. et al, (2010). "Normal and Diseased Primary Human Tenocytes in Response to rhPDGF-BB," Poster No. 1118, *56th Annual Meeting of the Orhopaedic Research Society*, located at < http://www.ors.org/web/Transactions/56/1118.pdf>, last visited on Feb. 23, 2010, 1 page.

Creaney, L. et al. (May 2008, e-pub. Nov. 5, 2007). "Growth Factor Delivery Methods in the Management of Sports Injuries: The State of Play," *Br. J. Sports Med.* 42(5):314-320, Abstract Only.

Curt et al. (Jan. 19, 2007). "Treatment of Avascular Osteonecorsis of the Mandible in Cancer Patients with a History of Bisphosphonate Therapy by Combining Bone Resection and Autologous Platelet Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (c-sis) of the Simian Sarcoma Virus onc Gene," *Science* 218:686-688.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Dines J.S. et al. (Sep./Oct. 2007). "Tissue Engineering and Rotator Cuff Tendon Healing," *J. Shoulder Elbow Surg.* 16(5S):204S-207S.

Dines, J.S. et al. (Sep./Oct. 2007). "The Effect of Growth on Differentiation Factor-5-Coated Sutures on Tendon Repair in a Rat Model," *J. Shoulder Elbow Surg.* 16(5S):215S-221S.

(56) References Cited

OTHER PUBLICATIONS

Donnelly, B.P. et al. (Jul. 2006). "Nucleotide Structure of Equine Platelet-Derived Growth Factor-A and -B and Expression in Horses with Induced Acute Tendinitis," *Am. J. Vet. Res.* 67(7):1218-1225, Abstract Only.

Doolittle et al. (Jul. 15, 1983). "Simian Sarcoma Virus onc Gene v-sis, Is Derived from the Gene (or Genes) Encoding a Platelet-Derived Growth Factor," *Science* 221:275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res.* 6(3):207-215.

Erikson, A. et al. (Nov. 5, 1991). "Induction of Platelet-Derived Growth Factor α- and β-Receptor mRNA and Protein by Platelet Derived Growth Factor BB," *J. Biol. Chem.* 266(31):21138-21144.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," *The BBI Newsletter*, located at http://findarticles.com/p/articles/mi_m3570/is_n9_v21/ai_n27541529>, last visited on Mar. 12, 2009, 2 pages.

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol.* 32:1123-1128.

Finkelman, R.D. et al. (1995). "Systematic PDGF ± Alendronate Increases Bone Density in OVX Rats," Abstract No. 1281, *J. Dental Res.* 74:172.

Fontana et al. "Effect of Platelet-Rich Plasma on the Pert-implant Bone Response: An Experimental Study," *Implant Dentistry*, 2004, 13:73-78.

Franco, B. et al. (Jan.-Jun. 2008). "Tissue Engineering Approaches for the Construction of a Completely Autologous Tendon Substitute," *Indian J. Plast. Surg.* 41(1):38-46, 13 pages.

Freedonia (Sep. 2006). "Biocompatible Materials. US Industry Study with Forecasts to 2010 & 2015," Study #2111, located at <http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," *Spine* 29(20):2270-2276.

Fukui, A. et al. (Sep. 1993). "Isolation and Characterization of *Xenopus* activin and Follistatin," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86-A(2):219-244.

Gamradt, S.C. et al. (Mar. 2007). "Platelet Rich Plasma in Rotator Cuff Repair," *Tech. in Orthop.* 22(1):26-33.

Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An In Vivo Biomechanic Study at 3 Weeks in Canines," *J. Hand Surg. Am.* 32A(3):373-379.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors-I (IGF-I) with Other Growth Factors on Bone Formation in vitro," Abstract No. 831, *J. Dental Res.* 73:205.

Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.

Giannobile, W.V, et al. (Nov. 1995). "Platelet Derived Growth Factor (PDGF) and Insulin-Like Growth Factor (IGF-I) Enhances Periodontal Regeneration in Macaca fascicularis," Abstract No. 28, *Advanced Dental Research* 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," *Bone*, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Perlodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Giddings, V.L. et al. (2000). "Calcaneal Loading During Walking and Running," *Med. Sci. Sports Exerc.* 32(3):627-634.

Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.

Goutallier, D. et al. (Jul. 1994). "Fatty Muscle Degeneration in Cuff Ruptures: Pre- and Postoperative Evaluation by CT Scan," *Clin. Orthop.* 304:78-83.

Grageda, "Piatelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-α and β-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs cf the Rotator Cuff," *J. Bone Joint Surg. Am.* 73-A(7):982-989.

Hart et al. "Synthesis, Phosphorylation, and Depreciation of Multiple Forms of the Platelet-derived Growth Factor Receptor Studied Using a Monoclonal Antibody," *The Journal of Biological Chemistry*, Aug. 5, 1987, 262(22):10780-10785.

(56) References Cited

OTHER PUBLICATIONS

Hart et al. "Two Classes of PDGF Receptor Recognize Different Isoforms of PDGF," *Science*, Jun. 1988, 240:1529-1531.

Hart, C.E, et al. "Purification of PDGF-AB and PDGF-BB from Human Platelet Extracts and Identification of all Three PDGF Dimers in Human Platelets," *Biochemistry*, Jan. 9, 1990, 29(1):166-172.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub, Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Hess, G.W. (Feb. 2010). "Achilles Tendon Rupture: A Review of the Etiology, Population, Anatomy, Risk Factors, and Injury Prevention," *Foot Ankle Spec.* 3(1):29-32.

Higashi, T. et al. (Jun. 1996). "influence of Particle Size of Calcium Phosphate Ceramics as a Capping Agent on the Formation of a Hard Tissue Barrier in Amputated Dental Pulp," *Journal of Endodontics* 22(6):281-283.

Hildebrand, K.A. et al. (1998). "The Effects of Platelet-Derived Growth Factor-BB on Healing of the Rabbit Medial Collateral Ligament. An In Vivo Study," *American Journal of Sports Medicine* 25(4):549-554.

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.

Hollinger, J.O. et al. (2008). "Protein Therapeutics and Bone Healing," Chapter 1 in *Tissue Engineering: Applications in Maxillofacial Surgery and Periodontics*. Second Edition, Lynch, S.E. et al. eds., Quintessence Publishing Co.: Hanover Park, IL, pp. 3-25.

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.

Howell, T.H. et al. (1996). "Polypeptide Growth Factors for Periodontal Regeneration," *Current Opinion in Periodontology* 3:149-156.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Huang, L-H. et al. "The Effect of Platelet-Rich Plasma on the Coronally Advanced Flap Root Coverage Procedure: A Pilot Human Trial," *J. Periodontal*, Oct. 2005, 76(10):1768-1777.

Hsu et al. (Jul. 2004). "Clinical Implications of Growth Factors in Flexor Tendon Wound Healing," *The Journal of Hand Surgery* 29A(4):551-563.

Ignotz, R.A. et al. (Mar. 25, 1986). "Transforming Growth Factor-β Simulates the Expression of Fibronectin and Collagen arid Their Incorporation in the Extracellular Matrix," *J. Biol.Chem*.261(9):4337-4345.

Ikezawa et al. "Characterization of Cementum Derived Growth Factor as an Insulin-Like Growth Factor-I Like Molecule," *Connective Tissue Research*, 1997, 36(4):309-319.

Inglis, A.E. et al. (Oct. 1976). "Ruptures of the Tendo Achilles: An Objective Assessment of Surgical and Non-Surgical Treatment," *J. Bone Joint Surg.* 58A(7):990-993.

Ito, Y. et al. (2004, e-pub. Mar. 25, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.

Jensen et al. "Platelet rich plasma and fresh frozen bone allograft as enhancement of implant fixation—an experimental study in dogs," *Journal of Orthopaedic Research*, 2004, 22:653-658.

Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.

Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.

Jiang, D. et al. "Modification of an Osteoconductive Anorganic Bovine Bone Miami Matrix with Growth Factors," *J. Periodonlol.*, Aug. 1999, 70(8):834-839.

Jin et al. "Engineering of Tooth-Supporting Structures by Delivery of PDGF Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis in Vivo," *PLoS ONE* 3(3):e1729, pp. 1-9.

Jones et al. (1992). "Isolation of Vgr-2, a Novel Member of the Transforming Growth Factor-Beta-related Gene Family," *Mol Endocnnol.* 6(11):1961-1968.

Jozsa, L. et al. (Aug. 1989). "Fibronectin and Laminin in Achilles Tendon," *Acta Orthop Sacninavica* 60(4):469-471.

Kademani, D. et al. (Aug. 2006). "Primary Surgical Therapy for Osteonecrosis of the Jaw Secondary to Bisphosphonate Therapy," *Mayo Clin. Proc.* 81(8):1100-1103.

Kaigler, "Growth factor delivery for oral and periodontal tissue engineering," *Expert Opin Drug Deliv.*, 2006, 3(5):647-662.

Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.

Kassolis et al. "Alveolar Ridge and Sinus Augmentation Utilizing Platelet-Rich Plasma in Combination with Freeze-Dried Bone Allograft: Case Series," Journal of Periodontology, Oct. 2000, 71(10):1654-1661.

Kazlauskas et al. "Different effects of homo- and heterodimers of platelet-derived growth factor A and B chains on human and mouse fibroblasts," *The EMBO Journal* (1988) 7 (12):3727-3735.

Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.

Kobayashi, M. et al. (May/Jun. 2006). "Expression of Growth Factors in Early Phase of Supraspinatus Tendon Healing in Rabbits," *J. Shoulder Elbow Surg.* 15(3):371-377.

(56) References Cited

OTHER PUBLICATIONS

Kovacevic, D. et al. (Mar. 2008). "Biological Augmentation of Rotator Cuff Tendon Repair," *Clin. Orthop. Relat. Res.* 466(3):622-633.

Kovacs et al. "Comparative Study of β-Tricalcium Phosphate Mixed with Platelet-Rich Plasma versus β-Tricalcium Phosphate, A Bone Substitute Material in Dentistry," *Acts Veterinaria Hungarica*, 2003, 51(4):475-484.

Landesberg et al. "Quantification of Growth Factor Levels Using a Simplified Method of Platelet-Rich Plasma Gel Preparation," *J. Oral Maxillofac. Surg.*, 2000, 58:297-301.

Lasa et al. "Delivery of Demineralized Bone Powder by Fibrin Sealant," *Plast. Reconstr. Surg.*, 1995, 96(6):1409-1417.

Lasa Jr., C. et al. (1996). "Bone Induction by Demineralized Bone Powder and Partially Purified Osteogenin Using a Fibrin-Sealant Carrier," Chapter 14 in *Surgical Adhesives arid Sealants: Current Technology and Applications*, Sierra, D. et al. eds., Technomic Publishing Company, Inc.: Lancaster, PA, pp. 135-144.

Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.

Lee., S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.

Lee et al. "Enhanced bone formation by controlled growth factor delivery from chitosan-based biomaterials," *Journal of Controlled Release*, 2002, 78: 187-197.

Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

Letson, A.K. et al. (1994). "The Effect of Combinations of Growth Factors on Ligament Healing," *Clinical Orhopaedics and Related Research* 308:207-212.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO. , Sep. 9-13, 1994, p. S135.

Liang et al. (Sep. 2000). "Effect of Cytokines on Repair of Tendon Injury," *Pub Med* 14(5):283-285, Abstract Only.

Liang, H.W. et al. (Aug. 2009). "Effect of Platelet-Derived Growth Factor-BB on Proliferation of Tendon Cells Cultured in vitro," *Zhonghua Shao Shang Za Zhi* 25(4):298-300, Abstract Only.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation byGBR: an experimental study in rats," *J. Clin. Periodontol.*, 2005, 32:1247-1253.

Lioubavina-Hack et al. "Effect of Bio-Oss® with or without platelet-derived growth factor on bone formation by 'guided tissue regeneration': a pilot study in rats," *J Clin. Periodontol*, 2005, 21(12):1254-1260.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1988). "Synergistic Effects of Recombinant Platelet-Derived Growth Factor Two Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," *Executive Committee on Chemotherpeutics; Amer. Acad Peridontal—Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontal.* 62(11):710-717.

Lynch, S.E. (1991). "Platelet-Derived Growth Factor and Insulin-Like Growth Factor. I: Mediators of Healing Soft Tissue and Bone Wounds," *Periodontal Case Reports NE Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration* Abstract, 2(1):84.

Lynch, S.E. et al. (1994). "Polypeptide Growth Factors: Molecular Mediators of Tissue Repair," Chapter 33 in *Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 in *Periodontal Regeneration: Current Status and Directions*, Polson, A. ed. Quintessence Publishing Co, Inc: Chicago, IL, 11:179-197.

Lynch, S.E. (1995). "Introduction," in *Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 in *Bone Regeneration and Repair: Biology and Clinical Applications*, Lieberman, J.R. et al. eds., Humana Press Inc,: Totowa, NJ, pp. 359-390.

Lynch, S.E. et al. (Dec. 2006). "A New Era in Periodontal and Periimplant Regeneration: Use of Growth-Factor Enhanced Matrices Incorporating rhPDGF," *Compendium of Continuing Education in Dentistry* 27(12):672-679.

Lynch, S.E. et al. (2008). "Use of rhPDGF to Improve Bone and Periodontal Regeneration," Chapter 6 in *Tissue Engineering: Applications in Maxillofacial Surgery and Periodontics*, Second Edition, Lynch, S.E. et al. eds., Quintessence Publishing Co.: Hanover Park, IL, pp. 87-102.

Maffulli, N. et al. (2002). "Tendon Healing: Can It Be Optimized?" *British Journal of Sports Medicine* 36:315-316.

Maffulli, N. et al. (2003). "Types and Epidemiology of Tendinopathy," *Clinics in Sports Medicine* 22:675-692.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

(56) References Cited

OTHER PUBLICATIONS

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 in *Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 in *Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with Anorganic Bovine Bone in the Chimpanzee," *The International Journal of Oral & Maxillofacial Implants*, 1999, 14(3):361-368.

Mccarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.

Mcguire, M.K. et al. (2006). "rhPDGF-BB Promotes Healing of Periodontal Defects: 24-Month Clinical and Radiographic Observations," *Int. J. Periodontics Restorative Dent.* 26(3):223-231.

Mcguire, M.K. (2008). "Soft Tissue Engineering Applications in Dentistry," Chapter 7 in *Tissue Engineering: Applications in Maxillofacial Surgery and Periodontics*, Second Edition, Lynch, S.E. et al. eds., Quintessence Publishing Co.: Hanover Park, IL, pp. 103-118.

Mcmurty, R.Y. et al. (1992). "Fractures of the Distal Radius," Chapter 35 in *Skeletal, Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphophonate Treatment," *Lancet Oncol.* 7:508-514.

Millette, E. et al. (2006). "Platelet-Derived Growth Factor-BB Transactivates the Fibroblast Growth Factor Receptor to Induce Proliferation in Human Smooth Muscle Cells," *Trends Cardiov. Med.* 16(1):25-28.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in In Vitro Wound Model," *J. Periodontal.* 72(3):331-340.

Nakamura, N. et al. (1998). "Early Biological Effect of In Vivo Gene Transfer of Platelet-derived Grown Factor (PDGF)-B into Healing Patellar Ligament," *Gene Therapy* 5:1165-1170.

Nancollas, G.H. el al. (2006, e-pub. Jul. 20, 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Pest. Dent.* 23(1):9-17.

Nevins et al. "Periodontal Regeneration in Humans Using Recombinant Human Platelet-derived Growth Factor-BB (rh PDGF-BB) and Allogenic Bone," *J. Periodontal*, Sep. 2003, 74(9):1282-1292.

Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4):365-373.

Nevins et al. "Platelet-Derived Growth Factor Stimulates Bone Fill and Rate of Attachment Level Gain: Results of a Large Multicenter Randomized Controlled Trial," *J. Periodontal*, Dec. 2005, 76(12):2205-2215.

Nevins, M. et al. (Oct. 2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nevins, M. et al. (2008). "Treatment of Advanced Periodontal Defects Using Bioactive Therapies," Chapter 5 in *Tissue Engineering: Applications in Maxillofacial Surgery and Periodontics*, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 in *Tissue Engineering: Applications in Maxillofacial Surgery and Periodontics*, Second Edition, Lynch, S.E. et al. eds., Quintessence Publishing Co.: Hanover Park, IL, pp. 119-131.

Nickols, J.C. et al. (2008). "The Role of Growth Factors in Tendon Healing," Chapter 20 in *Tissue Engineering: Applications in Maxillofacial Surgery and Periodontics*, Second Edition, Lynch, S.E. et al. eds., Quintessence Publishing Co.: Hanover Park, IL, pp. 276-289.

Nistor, L. (Mar. 1981). "Surgical and Non-Surgical Treatment of Achilles Tendon Rupture: A Prospective Randomized Study," *J. Bone Joint Surg Am.* 63A(3):394-399.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," *International Journal of Oral and Maxillofacial Surgery* 23(2):110-114, abstract only.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary, *Vitoss™ Scaffold* Syntehtic Cancellous Bone Void Filler," located at <http://www.accessdata.fda.gov/cdrh_docs/pdf/k994337.pdf, last visited on Mar. 30, 2010, 6 pages.

Orthovita, Inc. (Nov. 19, 2002). "Morningstar® Document Research™. Form 10-Q, Quarterly Repot Which Provides a Continuing View of

(56) References Cited

OTHER PUBLICATIONS a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedure—-Guided Tissue Regeneration and Demineralized Freeze-Dried Bone Allograft—in the Treatment of Intrabony Defects: A Clinical and Radiographic Study," *J. Periodontal*, 69(7):751-758.

Park et al. (Jun. 1995). "Periodontal Regeneration in Class III Furcation Defects of Beagle Dogs Using Guided Tissue Regenerative Therapy with Platelet-Derived Growth Factor," *J. Periodontol*. 66:462-477.

Paul, W. et al. (1999). "Development of Porous Spherical Hydroxyapatite Granules: Application Towards Protein Delivery," *J. Mater Sci. Mater. Med*. 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol*. 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts," *Arch. Orthop. Trauma Surg*. 123(9):435-488.

Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor β," *Endocrinology* 127(1):69-75.

Philippart et al. "Human Recombinant Tissue Factor, Platelet-rich Plasma, and Tetracycline Induce a High-Quality Human Bone Graft A 5-year Survey," *The International Journal of Oral and Maxillofacial Implants*, 2003, 18(3):411-416.

Phillips, S. et al. (1988). "The Direct Medical Costs of Osteoporosis for American Woman Aged 45 and Older, 1986," *Bone* 9(4):271-279.

Pickett, F.A. (Jul. 2006). "Bisphosphonate-Associated Osteonecrosis of the Jaw: A Literature Review and Clinical Practice Guidelines," *Journal of Dental Hygiene* 80(3):1-12.

Pietrzak, W.S. et al. (Jul. 2000). "Calcium Sulfate Bone Void Filler: A Review and a Lock Ahead," *J. Craniofac. Surg*. 11(4):327-333; discussion p. 334.

Polverini, P.J. (Aug. 2002). "Angiogenesis in Health and Disease: Insights into Basic Mechanisms and Therapeutic Opportunities," *Journal of Dental Education* 66(8):962-975.

Premdas, J. et al. (2001). "The Presence of Smooth Muscle Action in Fibroblasts in the Torn Human Rotator Cuff," *Journal of Orthopaedic Research* 19:221-228.

Qiu, Y. et al. (2009). "Combination of PDGF-BB and bFGF Reduces Differentiation but Maintains Proliferation of Human Tenocytes in Low Bovine Serum Culture in vitro," *European Cells and Materials* 18(Suppl. 2):86.

Qu, Z. et al. (Nov. 1994). "Immunolocalization of Basic Fibroblast Growth Factor and Platelet-Derived Growth Factor-A During Adjuvant Arthritis in the Lewis Rat," *Am. J. Pathol*. 145(5):1127-1139.

R&D Systems, Inc. (Date Unknown). "Quantikine Human PDGF-BB Immunoassay," *Package Insert*, Catalog No. DBB00, SBB, and PDB00, located at <http://www.rndsystems.com/pdf/dbb00.pdf>, last visited on Mar. 30, 2010, 16 pages.

Rao, C.D. et al. (Apr. 1986). "Structure and Sequence of the Human c-sis/Platelet-Derived Growth Factor 2 (SIS/PDGF2) Transcriptional Unit," *Proc. Natl. Acad. Sci. USA* 83:2392-2395.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med*. 23(3):407-413, Abstract Only, 2 pages.

Rasubala, L. et al. "Platelet-derived Growth Factor and Bone Morphogenetic Protein in the Healing of Mandibular Fractures in Rats," *British Journal of Oral and Maxillofacial Surgery*, 2003, 41:173-178.

Rettig, A.C. et al. (2005). "Potential Risk of Rerupture in Primary Achilles Tendon Repair in Athletes Younger Than 30 Years of Age," *Am. J. Sports Med*. 33(1):119-123.

Rickert, M. et al. (2001). "A Growth and Differentiation Factor-5 (GDF-5)-Coated Suture Stimulates Tendon Healing in an Achilles Tendon Model in Rats," *Growth Factors* 19:115-126.

Riley, G. (2004, e-pub. Jul. 16, 2003). "The Pathogenesis of Tendinopathy. A Molecular Perspective," *Rheumatology* 43(2):131-142.

Robbins, K.C. et al. (Oct. 13, 1983). "Structural and Immunological Similarities Between Simian Sarcoma Virus Gene Product(s) and Human Platelet-Derived Growth Factor," *Nature* 305:605-608.

Rodeo, S.A. et al. (Dec. 1993). "Tendon Healing in a Bone Tunnel," *J. Bone Joint Surg. Am*. 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med*. 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxillofac. Surg*., 2003, 61:157-163.

Rohrich et al. (Nov. 1999). "Mersilene Suture as a Vehicle for Delivery of Growth Factors in Tendon Repair," *Journal of the American Society of Plastic Surgeons* 104(6):1713-1717.

Rolf, C.G. et al. (2001). "Increased Cell Proliferation and Associated Expression of PDGFRβ Causing Hypercellularity in Patellar Tendinosis," *Rheumatology* 40:256-261.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.

Ruiz, G. et al. (1991). "Short Term Administration of Growth Factors Enhances Periodontal Regeneration," Abstract No. 1615, *J. Dental Res*. 70:468.

Russell, T.A. et al. (Date Unknown). "Trigen® IM Nail System Surgical Technique. Trochanteric Antegrade Nail (TAN™)," 24 pages.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.

Sakiyama-Elbert, S.E. et al. (Nov. 2008). "Controlled-Release Kinetics and Biologic Activity of Platelet-Derived Growth Factor-BB for Use in Flexor Tendon Repair," J. Hand Surg. Am. 33(9):1548-1557, Abstract Only.

Sandberg, "Matrix in Cartilage and Bone Development: Current Views on the Function and Regulation of Major Organic Components," *Annals of Medicine*, 1991, 23:207-217.

Sarment, D.P. et al. (Feb. 1, 2006). "Effect of rhPDGF-BB on Bone Turnover During Periodontal Repair," *Journal of Clinical Periodontolgy* 33(2):135-140.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res*. 14(3):369-372.

Sasai, Y. et al. (Dec. 2, 1994). "Xenopus chordin: A Novel Dorsalizing Factor Activated by Organizer-Specific Homeobox Genes," *Cell* 79:779-790.

Saygin et al. "Molecular and Cell Biology cf Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

(56) References Cited

OTHER PUBLICATIONS

Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.
Schmidt et al. "A review of the effects of insulin-like growth factor and platelet derived growth factor on in vivo cartilage healing and repair," *Osteoarthritis and Cartilage*, 2006, 14(5):403-412.
Schmidt, M.B. et al. (2008). "Tissue Engineering Strategies in the Treatment of TMDs," Chapter 18 in *Tissue Engineering: Applications in Maxillofacial Surgery and Periodontics*, Second Edition, Lynch, S.E. et al. eds., Quintessence Publishing Co.: Hanover Park, IL, pp. 252-264.
Schmitt, J.M. et al. (Nov. 1997). "Comparison of Porous Bone Mineral and Biologically Active Glass in Critical-Sized Defects," *J. Periodontol.* 68(11):1043-1053.
Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.
secinfo.com (Mar. 31, 2003). "Interpore International Inc/DE 10-K for Dec. 31, 2002," located at <http://www.secinfo.com/dV179.2kp.htm, last visited on May 20, 2010, 57 pages.
Seeherman, H.J. et al. (Oct. 2008). "rhBMP-12 Accelerates Healing of Rotator Cuff Repairs in Sheep Model," *J. Bone Joint Surg. Am.* 90A(10):2206-2219.
Shahgaldi, B.F. et al. (Jan. 1991). "Repair of Cartilage Lesions Using Biological Implants. A Comparative Histological and Biomechanical Study in Goats," *J. Bone Joint Surg, Br.* 73-B(1):57-64.
Sharma, P. et al. (2008). "Tendinopathy and Tendon Injury: The Future," *Disability and Rehabilitation* 30(20-22):1733-1745.
Sigma (Date Unknown). "Platelet Derived Growth Factor-BB," Product Information Sheet, 2 pages.
Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.
Simion, M. et al. (1994). "Vertical Ridge Augmentation Using a Membrane Technique Associated with Osseointegrated Implants," *Int. J. Periodontics Restorative Dent.* 14(6):497-511.
Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.
Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.
Simion, M. et al. (1999). "Effect of Different Microstructures if e-PTFE Membranes on Bone Regeneration and Soft Tissue Response: A Histologic Study in Canine Mandible," *Clin. Oral Implants Res.* 10:73-84.
Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.
Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.
Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.
Smith & Nephew (Date Unknown). "Trigen. Humeral Nail," Surgical Technique Pamphlet, 27 pages.
Sode, J. et al. (May 2007, e-pub. Mar. 3, 2007). "Use of Fluroquinolone and Risk of Achilles Tendon Rupture: A Population-based Cohort Study," *Eur. J. Clin. Pharmacol.* 53(5):499-503.

Solheim, E. "Growth Factors in Bone," *International Orthopedics (SICOT)*, 1998, 22:410-416. -------.
Spector, M. (2008). "Basic Principles of Scaffolds in Tissue Engineering," Chapter 2 in *Tissue Engineering: Applications in Maxillofacial Surgery and Periodontics Second Edition*, Lynch, S.E., et al. eds., Quintessence Publishing Co.: Hanover Park, IL, pp. 26-36.
Spindler, K.P. et al. (1995). "Proliferative Response to Platelet-Derived Growth Factor in Young and Old Rat Patellar Tendon," *Connective Tissue Research* 31(2):171-177.
Spindler, K.P. et al. (Jul. 1996). "Patellar Tendon and Anterior Cruciate Ligament Have Different Mitogenic Responses to Platelet-Derived Growth Factor and Transforming Growth Factor β," *Journal of Orthopaedic Research* 14(4):542-546.
Stephan, E.B. et al. (Apr. 1999). "Anogranic Bovine Bone Supports Osteoblastic Cell Attachment and Proliferation," *J. Periodontol.* 70(4):364-369.
Stephen et al. "Platelet-Derived Growth Factor Enhancement of a Mineral-Collagen Bone Substitute," *J. Periodontal*, Dec. 2000, 71:1887-1892.
Strom, T.B. (Sep. 6, 2005). "Saving Islets from Allograft Rejection," *PNAS USA* 102(36):12651-12652.
Suba et al. "Facilitation of 6-Tricalcium Phosphate-Induced Alveolar Bone Regeneration by Platelet-Rich Plasma in Beage Dogs: A Histologic and Histomorphometric Study," *The International J. of Oral and Maxillofacial Implants*, 2004, 19(6):832-838.
Tadic, D. et al. (2004). "A Novel Method to Produce Hydroxyapatite Objects with Interconnecting Porosity that Avoids Sintering," *Biomaterials* 25(16):3335-3340.
Tamai, N. et al. (2002). "Novel Hydroxyapatite Ceramics with an Interconnective Porous Structure Exhibit Superior Osteoconduction in vivo," *J. Biomed. Mater. Res.* 59:110-117.
Teraoka. K. et al. (2004). "Construction of an Interconnected Pore Network Using Hydroxyapatite Beads," *Key. Eng. Mater.* 254-256:257-259.
Teraoka, K. et al. (Sep. 2004). "Construction of Interconnected Pore Network Using Hydroxyapatite Small Components," *Trans. Mater. Res. Soc. Jpn.* 29(6):2919-2921.
Thompoulos, S. et al. (May 2005). "Effect of Several Growth Factors on Canine Flexor Tendon Fibroblast Proliferation and Collagen Synthesis in vitro," *J. Hand Surg. Am.* 30(3):441-447, Abstract Only.
Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.
Thomopoulos, S. et al. (Sep. 2009, e-pub. Mar. 25, 2009). "Enhanced Flexor Tendon Healing through Controlled Delivery of PDGF-BB," *J. Orthop. Res.* 27(9):1209-1215.
Thomopoulos, S. et al. (Feb. 2010, e-pub. Nov. 24, 2009). "bFGF and PDGF-BB for Tendon Repair: Controlled Release and Biologic Activity by Tendon Fibroblasts In Vitro," *Ann. Biomed. Eng.* 38(2):225-234.
Tinti, C. et al. (1996). "Vertical Ridge Augmentation: What is the Limit?" *Int. J. Periodontics Restorative Dent.* 16(3):221-229.
trending123.com (Date Unknown). "Stock Sectors, Medical Instruments Supls," located at <http://www.trending123.com/stock-sectors/Medical_Instruments_Supls.html>, last visited on May 3, 2010, 11 pages.
Uggen, C. et al. (2010). "The Effect of Recombinant Human Platelet-Derived Growth Factor Bb-Coated Sutures on Rotator Cuff Healing in a Sheep Model," *Arthroscopy* 26(11):1456'1462.
Uggen, J.C. et al. (Jan. 2005). "Tendon Gene Therapy Modulates the Local Repair Enviornment in the Shoulder," *J. Am. Osteopath. Assoc.* 105(1):20-21.
U.S. Appl. No. 10/965,319, filed Oct. 14, 2004, by Lynch (Copy not attached.).
Van Den Wyngaert, T. et al. (Aug. 2006). "Bisphosphonates and Osteonecrosis of the Jaw: Cause and Effect or a post hoc Fallacy?" *Annals of Oncology* 17(8):1197-1204.
Venkatasatya, M. et al. (2008). The Effect of PDGF, Vitamin D and PTH on Osteoblasts Derived From Patients on Chronic Bisphosphonate Therapy, Dissertation for The State University of New York at

(56) References Cited

OTHER PUBLICATIONS

Buffalo, located at <http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (EGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the *Drosophila* Tissue Polarity Gene Frizzled," *J. Biol. Chem.* 271(8):4468-4476.

Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.

Wang, X.T. et al. (Sep. 2004). "Tendon Healing In Vitro: Genetic Modification of Tenocytes With Exogenous PDGF Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

Wei et al. "Nano-Fibrous Scaffold for Controlled Delivery of Recombinant Human PDGF-BB," *Journal of Controlled Release*, 2006, e-pub. Mar. 3, 2006, 112:103-110.

Weiler, A. et al. (2004). "The Influence of Locally Applied Platelet-Derived Growth Factor-BB on Free Tendon Graft Remodeling After Anterior Cruciate Ligament Reconstruction," *Am. J. Sports Med.* 32(4):881-891.

White, E. et al. (1986). "Biomaterial Aspects of Interpore-200 Porous Hydroxyapatite," *Dent. Clin. North Am.* 30(1):49-67, Abstract only.

Wiesen, R.J. et al. (1998). "Efficacy of Bovine Bone Mineral in Vertical Osseous Defects," Abstract No. 1165, *J. Dental Res.* 77:777.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on A. actinomycetemcomitans," *J. Clin. Perrodont.* 16:116-119.

Williams et al. "Tissue Engineering: What Does it Mean? Why is it Important?" *Compendium*, Jan. 2005, 26(11:54-60.

Wisner-Lynch, L.A. (Oct. 2006). "From Passive to Active: Will Recombinant Growth Factor Therapeutics Revolutionize Regeneration?" *Int. J. Periodont. and Rest. Dent.* 26(5):409-411.

Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.

Woo, S.L-Y. et al. (1998). "Engineering the Healing of the Rabbit Medical Collateral Ligament," *Medical and Biological Engineering and Computing* 36:359-364.

Woo, S-B. et al. (May 16, 2006). "Systematic Review: Bisphosphonates and Osteonecrosis of the Jaws," *Annals of Internal Medicine* 144(10):753-761.

Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.

Yazawa et al. "Basic Studies on the Clinical Applications of Platelet-Rich Plasma," *Cell Transplantation*, 2003, 12:509-518.

Yazawa, M. et al. (May 2004). "Basic Studies on the Bone Formation Ability by Platelet Rich Plasma in Rabbits," *Journal of Craniofacial Surgery* 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.

Younger, E.M. et al. (1989). "Morbidity at Bone Graft Donor Sites," *J. Orthop. Trauma* 3(3):192-195.

Zavras, A.I. et al. (2006). "Bisphosphonates Are Associated With Increased Risk for Jaw Surgery in Medical Claims Data: Is it Osteonecrosis?" *J. Oral Maxillofac. Surg.* 64:917-923.

Zhu et al. "Gene Transfer and Expression of Platelet-Derived Growth Factors Modulate Periodontal Cellular Activity," *J. Dent Res*, 2001, 80(3):892-897.

Zimmer, Inc. (2005). "Zimmer® Collagen Repair Patch," Product No. 04-4100-001-00, 6 pages.

Two Planes of Sectioning

PLATELET-DERIVED GROWTH FACTOR
COMPOSITION AND METHODS FOR THE
TREATMENT OF TENDON AND LIGAMENT
INJURIES

CROSS-REFERENCE TO RELATED APPLICATIONS

This application is a continuation of U.S. application Ser. No. 14/500,354, filed Sep. 29, 2014, which is a continuation of U.S. application Ser. No. 12/556,555, filed Sep. 9, 2009, now U.S. Pat. No. 8,870,954, issued on Oct. 28, 2014, which claims the benefit under 35 U.S.C. § 119(e) of U.S. Provisional Application No. 61/191,641, filed Sep. 9, 2008, U.S. Provisional Application No. 61/144,088, filed Jan. 12, 2009, and U.S. Provisional Application No. 61/144,126, filed Jan. 12, 2009; U.S. application Ser. No. 12/556,555 is also a continuation-in-part of PCT Application No. PCT/US2009/056418, filed on Sep. 9, 2009; the entireties of which are herein incorporated by reference.

TECHNICAL FIELD

This invention relates to compositions and methods for treatment of tendon or ligament injuries, such as ruptured, severed, torn, or transected tendons or ligaments or tendon or ligament detachment from bone, and in particular to methods for treatment of tendon or ligament injuries by administering compositions comprising a biocompatible matrix in combination with platelet-derived growth factor (PDGF).

BACKGROUND OF THE INVENTION

Tendons and ligaments are the tough fibers that connect muscle to bone or bone to bone, but tendons and ligaments can be ruptured, severed, or detached from the bone for a variety of reasons. Such tendon or ligament injuries may generally occur due to or resulting from direct trauma to the affected tendon/ligament, weakening of the tendon/ligament due to advanced age, eccentric loading, repetitive motions, overuse and/or increased stress or activity. Such acute injuries are quite dramatic and usually leave the individual unable to move the affected joint.

The most common areas of tendon rupture, tendon severance, or detachment from the bone are (1) the quadriceps (a group of four muscles, the vastus lateralis, vastus medialis, vastus intermedius, and the rectus femoris) which come together just above the kneecap (patella) to form the patellar tendon; (2) the Achilles tendon, located on the back (posterior) portion of the foot just above the heel. The Achilles tendon serves as the attachment of the calf muscle (gastrocnemius muscle) to the heel of the foot (the calcaneus bone); (3) the rotator cuff, located in the shoulder and composed of four muscles (the supraspinatus (the most common tendon ruptured), infraspinatus, teres minor, and subscapularis); (4) the biceps of the arm, which functions as a flexor of the elbow. Ruptures of the biceps are classified into proximal (close) and distal (far) types; and (5) the flexor tendons of the hand, such as the flexor brevis and longus. The most common areas of ligament rupture, ligament severance, or detachment from the bone are the anterior cruciate ligament (ACL), posterior cruciate ligamen (PCL), and medial collateral ligament (MCL). For almost all tendon and ligament injuries there may be consideration pain (either acute or chronic), loss of motion and weakness of the affected joint or limb. For a ruptured or detached tendon/ligament, surgery is the most common course of treatment, in order to secure the tendon or ligament to its bone, or to reconnect the ruptured or severed ends of the affected tendon/ligament. For other tendon/ligament injuries, common treatments include rest, ice, NSAIDs, corticosteroid injections, heat, and ultrasound. However, despite decades of research and increasing clinical attention to these injuries, their clinical outcomes remain unpredictable.

With respect to the quadricepts, rupture of the patellar tendon is a relatively infrequent, yet disabling injury, which is most commonly seen in patients less than 40 years of age. It tends to occur during athletic activities when a violent contraction of the quadriceps muscle group is resisted by the flexed knee. Rupture usually represents the final stage of a degenerative tendinopathy resulting from repetitive microtrauma to the patellar tendon.

With respect to the Achilles tendon, both athletes and non-athletes are at risk for developing injuries at all ages, with most injuries occurring in men between the ages of 30 and 50 years of age (Boyden, E., et al., *Clin Orthop,* 317:150-158 (1995); Hattrup, S. and Johnson, K, *Foot and Ankle,* 6: 34-38 (1985); Jozsa, L., et al., *Acta Orthop Scandinavica,* 60:469-471(1989)). Achilles tendonitis and tendinosis are also common in individuals whose work puts stress on their ankles and feet, as well as in "weekend warriors," those who are less conditioned and participate in athletics only on weekends or infrequently.

In the case of rotator cuff injuries, notwithstanding advances in surgical instrumentation and techniques, the current techniques fall short of producing an enduring repair, with some studies citing failure rates as high as 94%. Failure of tendon repairs may be attributed to poor healing of the damaged tendon and poor reattachment of the injured tendon to the bone.

A firm attachment of ligament to bone is also essential for many ligament reconstruction procedures. Successful ligament substitution procedures, such as anterior cruciate ligament reconstruction, require fixation of a tendon graft into a bone tunnel and progressive ingrowth of bone into the tendon to create a biological attachment between the bone and the tendon. Histological and biomechanical studies show that it generally requires six to twelve weeks after the transplantation of a tendon graft to a bone to achieve bone ingrowth, tendon-bone attachment, mineralization, and greater collagen-fiber continuity between the tendon and the bone. See, Rodeo S. A. et al., *Tendon-Healing in a Bone Tunnel,* 75(12): 1795-1803 (1993).

Accordingly, there is a need to provide new compositions and new methods of treatment for various tendon/ligament injuries and tendon/ligament to bone attachment to improve the healing response associated with surgical repairs or other non-surgical treatments.

All references cited herein, including, without limitation, patents, patent applications and scientific references, are hereby incorporated by reference in their entirety.

SUMMARY OF THE INVENTION

The present invention provides for compositions and methods of treatment of tendon or ligament injuries.

In one aspect of the invention, a composition is provided comprising a biocompatible matrix and platelet-derived growth factor (PDGF), wherein the biocompatible matrix comprises pores, wherein the biocompatible matrix has a porosity of at least about 80%, and wherein at least about 50% of the PDGF is released within about 24 hours.

In another aspect, the invention provides a method for treatment of a tendon injury or a ligament injury not involving a bone in an individual comprising administering to an affected site of the injury of the individual an effective amount of a composition comprising: a biocompatible matrix and platelet-derived growth factor (PDGF), wherein the biocompatible matrix comprises pores, wherein the biocompatible matrix has a porosity of at least about 80%, and wherein at least about 50% of the PDGF is released within about 24 hours. In some embodiments, the method further comprises the step of mechanically stabilizing the tendon or ligament injury. In some embodiments, the step of stabilizing the tendon or ligament injury comprises suturing the tendon or ligament injury, wherein the sutured tendon or ligament is positioned such that the ends of the injured tendon or ligament are substantially re-approximated. In some embodiments, the step of administering comprises administering to the affected site of the injury of said individual the effective amount of the composition using a syringe.

In another aspect, the invention provides a method for attaching or reattaching a tendon to a bone in an individual comprising administering to the individual an effective amount of a composition comprising a biocompatible matrix and platelet-derived growth factor (PDGF) at an interface between the tendon and the bone, wherein the biocompatible matrix comprises pores, wherein the biocompatible matrix has a porosity of at least about 80%, and wherein at least about 50% of the PDGF is released within about 24 hours.

In another aspect, the invention provides a method for attaching or reattaching a ligament to a bone in an individual comprising administering to the individual an effective amount of a composition comprising a biocompatible matrix and platelet-derived growth factor (PDGF) at an interface between the ligament and the bone, wherein the biocompatible matrix comprises pores, wherein the biocompatible matrix has a porosity of at least about 80%, and wherein at least about 50% of the PDGF is released within about 24 hours.

In another aspect, the invention provides a kit for treatment of a tendon or a ligament injury not involving a bone in an individual comprising a first container comprising a biocompatible matrix and a second container comprising a platelet-derived growth factor (PDGF) solution, wherein the biocompatible matrix comprises pores, wherein the biocompatible matrix has a porosity of at least about 80%, and wherein at least about 50% of the PDGF is released within about 24 hours.

In yet another aspect, the invention provides a kit for attaching a tendon or a ligament to a bone in an individual comprising a first container comprising a biocompatible matrix and a second container comprising a platelet-derived growth factor (PDGF) solution, wherein the biocompatible matrix comprises pores, wherein the biocompatible matrix has a porosity of at least about 80%, and wherein at least about 50% of the PDGF is released within about 24 hours.

Any of the compositions as described herein may be used in any of the methods or kits as described herein. The various embodiments as described below may be used in conjunction with any aspects of the invention, as would be apparent to one of ordinary skill in the art.

In some embodiments, the biocompatible matrix has a porosity of at least about 25%, at least about 50%, at least about 75%, at least about 85%, at least about 90%, at least about 92%, at least about 94%, at least about 95%, at least about 96%, at least about 97%, at least about 98%, at least about 99%, about 80% to about 95%, about 85% to about 95%, about 85% to about 90%, about 90% to about 92%, or about 92% to about 95%.

In some embodiments, the pores have an average area ranging from about 800 $\mu m^2$ to about 3,000 $\mu m^2$, about 13,000 $\mu m^2$ to about 50,000 $\mu m^2$, about 2500 $\mu m^2$ to about 20,000 $\mu m^2$, about 4500 $\mu m^2$ to about 20,000 $\mu m^2$, about 5000 $\mu m^2$ to about 19,000 $\mu m^2$, about 6000 $\mu m^2$ to about 18,000 $\mu m^2$, about 6000 $\mu m^2$ to about 15,000 $\mu m^2$, or about 5000 $\mu m^2$ to about 16000 $\mu m^2$.

In some embodiments, the pores have an average perimeter ranging from about 100 $\mu m$ to about 200 $\mu m$, about 400 $\mu m$ to about 800 $\mu m$, about 200 $\mu m$ to about 500 $\mu m$, about 200 $\mu m$ to about 600 $\mu m$, about 300 $\mu m$ to about 600 $\mu m$, or about 300 $\mu m$ to about 500 $\mu m$.

In some embodiments, the pores have average diameters ranging from about 1 $\mu m$ to about 1 mm. In some embodiments, the pores have average diameters at least about 5 $\mu m$, at least about 10 $\mu m$, at least about 20 $\mu m$, at least about 30 $\mu m$, at least about 40 $\mu m$, or at least about 50 $\mu m$, about 5 $\mu m$ to about 500 $\mu m$, about 10 $\mu m$ to about 500 $\mu m$, about 50 $\mu m$ to about 500 $\mu m$, about 100 $\mu m$ to about 500 $\mu m$, or about 100 $\mu m$ to about 300 $\mu m$.

In some embodiments, the pores comprise interconnected pores.

In some embodiments, at least about 50%, at least about 55%, at least about 60%, at least about 65%, at least about 70%, at least about 75%, at least about 80%, at least about 85%, at least about 90%, at least about 95%, about 50% to about 95%, about 60% to about 95%, about 70% to about 95%, about 80% to about 95%, about 90% to about 95%, about 50% to about 85%, about 60% to about 85%, about 70% to about 85%, or about 50% to about 80% of the PDGF is released within about 24 hours. In some embodiments, at least about 50%, at least about 55%, at least about 60%, at least about 65%, at least about 70%, at least about 75%, at least about 80%, at least about 85%, at least about 90%, at least about 95%, about 50% to about 95%, about 60% to about 95%, about 70% to about 95%, about 80% to about 95%, about 90% to about 95%, about 50% to about 85%, about 60% to about 85%, about 70% to about 85%, or about 50% to about 80% of the PDGF is released within about 1 hour, about 6 hours, about 8 hours, about 12 hours, or about 48 hours. In some embodiments, the PDGF release is measured in vivo. In some embodiments, the PDGF release is measured in vitro. In some embodiments, the PDGF is released into the surrounding region. In some embodiments, the PDGF is released onto an injured tendon or ligament. In some embodiments, the PDGF is released onto the surface of the bone near the point of bone-tendon or bone-ligament attachment. In some embodiments, the PDGF is released into the surrounding media.

In some embodiments, the biocompatible matrix is resorbed within about 1 month, about 3 months, about 6 months, or about 9 months of in vivo administration. In some embodiments, the biocompatible matrix is resorbed within about 30 days, about 25 days, about 21 days, about 18 days, about 15 days, about 10-14 days, or about 10 days of in vivo administration.

In some embodiments, the biocompatible matrix comprises collagen. In some embodiments, the collagen comprises Type I collagen. In some embodiments, the collagen is cross-linked.

In some embodiments, the collagen is soluble. In some embodiments, the collagen is insoluble. In some embodiments, the collagen comprises a soluble collagen monomer component and an insoluble collagen polymer component.

In some embodiments, the ratio of soluble collagen monomers to insoluble collagen polymers is about 1:10, about 1:9, about 1:8, about 1:7, about 1:6, about 1:5, about 1:4, about 1:3, about 1:2, or about 1:1.

In some embodiments, the biocompatible matrix further comprises a glycosaminoglycan. In some embodiments, the glycosaminoglycan is chondroitin sulfate. In some embodiments, the glycosaminoglycan is not chondroitin sulfate.

In various embodiments, the composition is a gel, particle, powder, paste, sheet, pad, patch, or sponge. In some embodiments, the composition is flowable.

In some embodiments, the biocompatible matrix is COLLATAPE®. In some embodiments, the biocompatible matrix is BIOBLANKET®. In some embodiments, the biocompatible matrix is not BIOBLANKET®. In some embodiments, the biocompatible matrix does not oxidize PDGF.

In some embodiments, the PDGF is present as a solution comprising PDGF, wherein the concentration of PDGF in the solution is about 0.1 to about 10.0 mg/ml, about 5 mg/ml to about 20 mg/ml, about 0.1 mg/ml to about 2.0 mg/ml, about 0.1 mg/ml to about 0.4 mg/ml, or about 0.9 mg/ml to about 1.5 mg/ml. In some embodiments, the PDGF solution is about 0.15 mg/ml, about 0.3 mg/ml, about 1.0 mg/ml, about 1.5 mg/ml, about 2.0 mg/ml, or about 10.0 mg/ml.

In some embodiments of the present invention, PDGF is a PDGF homodimer, in other embodiments, PDGF is a heterodimer, including for example, PDGF-AA, PDGF-BB, PDGF-AB, PDGF-CC, PDGF-DD, and mixtures and derivatives thereof. In some embodiments, PDGF comprises PDGF-BB. In other embodiments, PDGF comprises a recombinant human (rh) PDGF such as recombinant human PDGF-BB (rhPDGF-BB).

In some embodiments of the present invention, PDGF is a PDGF fragment. In some embodiments, rhPDGF-B comprises the following fragments: amino acid sequences 1-31, 1-32, 33-108, 33-109, and/or 1-108 of the entire B chain.

In some embodiments, cells infiltrate the composition of the present invention within about 3 weeks, about 2 weeks, about 1 week, about 7 days, about 6 days, about 5, about 4, about 3, about 2, or about 1 day(s) after exposure to the composition. In some embodiments, the cells are tenocytes. In some embodiments, the cells are osteoblasts. In some embodiments, the cells are ligament cells.

In some embodiments, compositions and methods of the present invention are useful in the attachment of tendons to bone or ligaments to bone, and may be applied to any tendon or ligament attachment. In some embodiments, compositions and methods of the present invention enhance tendon attachment to bone or ligament attachment to bone by strengthening the tendon and/or bone and ligament and/or bone at the site of tendon/ligament attachment to the bone. Other types of damaged or injured tendons and/or ligaments, such as a tendon/ligament exhibiting tearing, delamination, and/or any other strain or deformation, may also be treated by the methods of the invention. A single type of injury may be treated, or more than one type of injury may be treated simultaneously. In some embodiments, the treatment involves treating a tendon. In some embodiments, the treatment involves treating a ligament. In some embodiments, a tendon graft is used for the specific treatment of tendon and/or ligament tissues. In other embodiments, a ligament graft is used for the specific treatment of tendon and/or ligament tissues.

In some embodiments, compositions and methods of the present invention are useful both in the attachment or reattachment of tendons to bone and any tendon injuries not involving a bone. In some embodiments, compositions and methods of the present invention are useful both in enhancing attachment or reattachment of tendons to bone and any tendon injuries not involving a bone. In other embodiments, compositions and methods of the present invention are useful both in the attachment or reattachment of ligaments to bone and any ligament injuries not involving a bone. In other embodiments, compositions and methods of the present invention are useful both in enhancing attachment or reattachment of ligaments to bone and any ligament injuries not involving a bone.

In some embodiments, the tendon which may be treated by compositions and methods of the present invention include, but are not limited to, tendons of the subscapularis, supraspinatus, infraspinatus, teres minor, rectus femoris, tibialis posterior, quadriceps femoris, biceps brachii, as well as the Achilles Tendon, patellar tendon, abductor and adductor tendons, or other tendons of the hip, the common extensor tendon, common flexor tendon, flexor digitorum superficialis tendons, extensor digitorum and extensor minimi tendons, or other tendons of the arm and hand. In some embodiments, the tendon which may be treated by composition and methods of the present invention is selected from the group consisting of: patellar tendon, anterior tibialis tendon, Achilles tendon, Hamstring tendon, semitendinosus tendon, gracilis tendon, abductor tendon, and adductor tendon. In some embodiments, the tendon which may be treated by compositions and methods of the present invention is selected from the group consisting of supraspinatus tendon, infraspinatus tendon, subscapularis tendon, teres minor tendon (rotator cuff complex), flexor tendon, rectus femoris tendon, tibialis posterior tendon, and quadriceps femoris tendon. In some embodiments, tendon which may be treated by compositions and methods of the present invention is selected from the group consisting of patellar tendon, anterior tibialis tendon, Achilles tendon, Hamstring tendon, semitendinosus tendon, gracilis tendon, abductor tendon, adductor tendon, supraspinatus tendon, infraspinatus tendon, subscapularis tendon, teres minor tendon (rotator cuff complex), flexor tendon, rectus femoris tendon, tibialis posterior tendon, and quadriceps femoris tendon. In some embodiments, tendon which may be treated by compositions and methods of the present invention is not selected from the group consisting of supraspinatus tendon, infraspinatus tendon, subscapularis tendon, teres minor tendon (rotator cuff complex), flexor tendon, rectus femoris tendon, tibialis posterior tendon, and quadriceps femoris tendon.

In some embodiments, the ligament which may be treated by compositions and methods of the present invention is selected from the group consisting of anterior cruciate ligament, lateral collateral ligament, posterior cruciate ligament, medial collateral ligament, cranial cruciate ligament, caudal cruciate ligament, cricothyroid ligament, periodontal ligament, suspensory ligament of the lens, anterior sacroiliac ligament, posterior sacroiliac ligament, sacrotuberous ligament, sacrospinous ligament, inferior pubic ligament, superior pubic ligament, suspensory ligament, palmar radiocarpal ligament, dorsal radiocarpal ligament, ulnar collateral ligament, and radial collateral ligament.

In some embodiments, bones which may be treated by compositions and methods of the present invention include, but are not limited to, for example, tibia, femur, and humerus.

In some embodiments, the tendon or ligament injury not involving a bone is a tendon or ligament rupture, severance, tearing, delamination, strain, or deformation.

In some embodiments, the attachment of the tendon to the bone is for rotator cuff injury treatment. In some embodiments, the attachment of the tendon to the bone or ligament to the bone is for anterior cruciate ligament reconstruction.

In some embodiments, provided is a method for treatment of a tendon or a ligament injury in an individual comprising administering to said individual an effective amount of a composition comprising a biocompatible matrix and platelet-derived growth factor (PDGF), wherein the PDGF is at a concentration in the range of about 0.1 mg/ml to about 1.0 mg/ml; and wherein the biocompatible matrix forms a porous structure comprising pores with a pore area size ranging from about 4500 $\mu m^2$ to about 20000 $\mu m^2$ and a pore perimeter size ranging from about 200 μm to about 500 μm.

In some embodiments, provided is a method for treatment of a tendon or a ligament injury in an individual comprising administering to an affected site of the injury of said individual an effective amount of a composition comprising a biocompatible matrix and platelet-derived growth factor (PDGF), wherein the PDGF is at a concentration in the range of about 0.1 mg/ml to about 1.0 mg/ml; and wherein the composition is flowable.

In some embodiments, provided is a method for attaching a tendon into a bone or a ligament into a bone in an individual comprising administering to said individual an effective amount of a composition comprising a biocompatible matrix and platelet-derived growth factor (PDGF) at an interface between the tendon and the bone or the ligament and the bone, wherein the biocompatible matrix forms a porous structure comprising pores with a porosity greater than about 85%.

In some embodiments, provided is a method for attaching a tendon into a bone in an individual for anterior cruciate ligament reconstruction comprising administering to said individual an effective amount of a composition comprising a biocompatible matrix and platelet-derived growth factor (PDGF) at an interface between the tendon and the bone, wherein the biocompatible matrix forms a porous structure comprising pores with a porosity greater than about 85%.

In some embodiments of the present invention, the method may be performed using arthroscopic techniques, endoscopic techniques, laparoscopic techniques, or any other suitable minimally-invasive techniques.

BRIEF DESCRIPTION OF THE FIGURES

FIG. 16A: The 0.15 mg/ml rhPDGF-BB and 0.30 mg/ml rhPDGF-BB groups underwent significantly greater conditioning elongation than the Suture Only and Suture+Collagen Matrix groups. FIG. 16B: There were no significant differences in peak-to-peak elongation between any groups.

FIG. 17A: Repair augmentation with 0.15 mg/ml and 0.30 mg/ml rhPDGF-BB resulted in a 63.7% and 63.3% increase in load to failure relative to the Suture Only group, respectively. FIG. 17B: lower rhPDGF-BB doses of 0.15 mg/ml and 0.30 mg/ml outperformed the higher 1.0 mg/ml PDGF dose, manifested as a 120% and 119.3% increase, respectively, in load at failure.

DETAILED DESCRIPTION OF THE INVENTION

Figure 1:
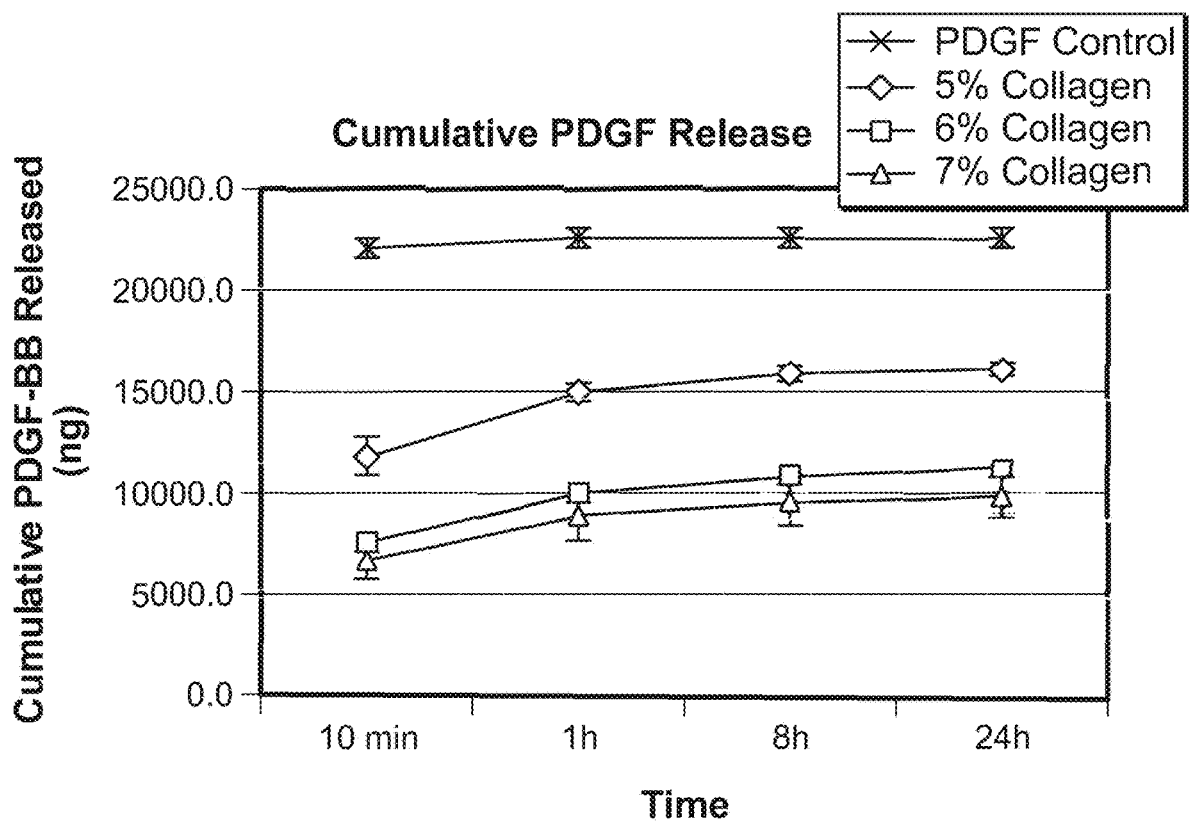
FIG. 1 depicts the cumulative rhPDGF-BB released from different collagen matrices over 24 hours.

The present invention is based, in part, on the observation that biocompatible matrices comprising platelet-derived growth factor (PDGF) may be used in treatment of tendon or ligament injuries not involving bone and for tendon-bone and ligament-bone tissue repair.

The present invention will use, unless otherwise indicated, conventional techniques of molecular biology (including recombinant techniques), cell biology, biochemistry, nucleic acid chemistry, and immunology, which are well known to those skilled in the art. The present invention will also use, unless otherwise indicated, conventional techniques and apparatus of surgery and other medical methods, which are well known to those skilled in the art. Unless defined otherwise, technical and scientific terms used herein have the same meaning as commonly understood by one of ordinary skill in the art to which this invention belongs.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein, unless otherwise specified, the term "treatment" or "treating" refers to administrating to an individual an effective amount of a composition comprising a biocompatible matrix and platelet-derived growth factor which alleviates, slows progression of, speeds healing of, improves the healing response of, or repairs a pathology for which the individual is being treated, and/or which results in one or more desirable clinical or therapeutic effects which include, but are not limited to, alleviation of pain associated with an injured tendon or ligament, increase in range of motion of the affected joint, and increased strength and attachment of tendon or ligament to tendon or ligament or tendon/ligament to bone at the repair site.

An "effective amount" refers to at least an amount effective, at dosages and for periods of time necessary, to achieve the desired therapeutic or clinical result. An effective amount can be provided in one or more administrations.

As used herein, treatment of "a tendon injury or a ligament injury not involving a bone" refers to the treatment of an injured or damaged tendon or ligament that does not involve injured bone or tendon/ligament detachment from the bone. Examples of such tendon or ligament injury include, but are not limited to severed tendons/ligaments, ruptured tendons/ligaments, tendons/ligaments exhibiting tearing, delamination, or any other strain or deformation. The individual being treated may have injury to a bone or tendon-bone/ligament-bone detachment in addition to the tendon or ligament injury, however, treatment of "a tendon or a ligament injury not involving a bone" refers to the specific treatment of tendon and/or ligament tissues. It is to be understood that in some embodiments, an individual may be treated for a tendon injury or a ligament injury not involving a bone as well as an injury involving a bone, for example, a tendon-bone or ligament-bone attachment. In some embodiments, only a tendon injury or a ligament injury not involving a bone is treated.

An "individual" refers a mammal, including humans, domestic and farm animals, and zoo, sport, or pet animals, such as chimpanzees and other apes and monkey species, dogs, horses, rabbits, cattle, pigs, goats, sheep, hamsters, guinea pigs, gerbils, mice, ferrets, rats, cats, and the like. Preferably, the individual is human. The term does not denote a particular age or gender.

"Bioresorbable" refers to the ability of a biocompatible matrix to be resorbed or remodeled m vivo. The resorption process involves degradation and elimination of the original material through the action of body fluids, enzymes or cells. The resorbed material may be used by the host in the formation of new tissue, or it may be otherwise re-utilized by the host, or it may be excreted.

Collagen matrices, as referred to herein, include materials in the form of, for example, gels, pastes, particles, powders, sheets, patches, pads, paste, or sponges. Collagen matrices as obtained commercially are usually manufactured from collagen extracts of bovine dermis and/or bovine tendon. In some embodiments, the bovine tendon source is bovine deep flexor (Achilles) tendon. In some embodiments, the matrices are made from collagen slurries where the concentration of the collagen in the slurry is different for each type of matrix. For example, one type of collagen matrix is made from a slurry with a collagen concentration of 4.5%, this collagen matrix is referred to herein as "collagen (4.5%)" or "collagen matrix (4.5%)"; a second type of collagen matrix is made from a slurry with a collagen concentration of 5%, this collagen matrix is referred to herein as "collagen (5%)" or "collagen matrix (5%)"; a third type of collagen matrix is made from a slurry with a collagen concentration of 6%, this collagen matrix is referred to herein as "collagen (6%)" or "collagen matrix (6%); and a fourth type of collagen matrix is made from a slurry with a collagen concentration of 7%, this collagen matrix is referred to herein as "collagen (7%)" or "collagen matrix (7%). For any collagen matrix the percent of collagen used in the starting slurry does not necessarily reflect the percentage of collagen in the final collagen matrix.

As used herein, the term, "attaching" or "attachment", as used herein, is meant to include reattaching or reattachment of a tendon to or into a bone, or a ligament to or into a bone, and also includes attaching a graft (e.g. a tendon or ligament graft) to or into a bone. For example, using a non-limiting example, when performing anterior cruciate ligament reconstruction, the injured ligament may be removed from the bone, and a graft, such as a tendon or ligament graft, may be attached to or into the bone in place of the original ligament.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X".

It is understood that aspects and embodiments of the invention described herein include "comprising," "consisting," and "consisting essentially of" aspects and embodiments.

Compositions and Methods of the Invention

Described herein are compositions and methods for treatment of tendon or ligament injuries not involving a bone in an individual. In general, the methods of treatment comprise administering a composition comprising a biocompatible matrix and PDGF to an individual who has a tendon or a ligament injury. Specifically, the methods of treatment comprise administering a composition comprising a collagen matrix and PDGF to the site of the tendon or the ligament injury.

Described also herein are compositions and methods for attaching or reattaching a tendon or a ligament to/into a bone in an individual. In general, the methods of attachment comprise administering a composition comprising a biocompatible collagen matrix and PDGF at an interface between the tendon/ligament and the bone.

Biocompatible Matrix

A biocompatible matrix, according to some embodiments of the present invention, comprises a scaffolding matrix. The scaffolding matrix, according to some embodiments of the present invention, provides a framework or scaffold for new tissue growth to occur, including tendon/ligament and/or bone tissue.

The biocompatible matrix, in some embodiments, comprises a collagen matrix. The term "collagen matrix" can refer to, for example, a collagen gel, paste, powder, particle, patch, pad, sheet or sponge. In some embodiments, the collagen matrix comprises any type of collagen, including Type I, Type II, and Type III collagens. In some embodiments, the collagen comprises a mixture of collagens, such as a mixture of Type I and Type II collagen. In other embodiments, the collagen is soluble under physiological conditions. In some embodiments, the collagen is insoluble under physiological conditions. In some embodiments, the collagen comprises soluble and insoluble components. In some embodiments, the collagen matrix comprises a fibrous collagen such as soluble type I bovine collagen. In some embodiments, the collagen matrix comprises fibrous and acid-soluble collagen derived from bovine dermal tissue. Other types of collagen present in bone or musculoskeletal tissues may be employed. Recombinant, synthetic and naturally occurring forms of collagen may be used in the present invention. Collagen may be cross-linked or not cross-linked.

Fibrous collagen suitable for use in the collagen matrix may demonstrate sufficient mechanical properties, including wet tensile strength, to withstand suturing and hold a suture without tearing. A fibrous collagen matrix, for example, can have a wet tear strength ranging from, for example, about 0.75 pounds to about 5 pounds.

In some embodiments, the biocompatible matrix comprises a glycosaminoglycan (GAG). In some embodiments, the biocompatible matrix comprises collagen and glycosaminoglycan (GAG), for example cross-linked collagen and GAG. In some embodiments, the GAG is chondroitin sulfate. In some embodiments, the GAG is not chondroitin sulfate. Other GAGs include, but are not limited to, dermatan sulfate, keratan sulfate, heparin, heparan sulfate, hyaluronan, and combinations thereof. In some embodiments, the weight/weight ratio of collagen to GAG is about 90:10. In some embodiments, the weight/weight ratio of collagen to GAG is about 92:8. In some embodiments, the weight/weight ratio of collagen to GAG is about 95:5. In some embodiments, the biocompatible matrix comprises cross-linked collagen with chondroitin sulfate. In other embodiments, the biocompatible matrix comprises cross-linked collagen with GAG, wherein the GAG is not chondroitin sulfate.

In some embodiments, a collagen matrix is obtained from a commercial source, including, but not limited to, COLLATAPE® (Integra LifeSciences Corporation, Plainsboro, N.J.); INTEGRA Flowable Wound Matrix (Integra LifeSciences Corporation, Plainsboro, N.J.); Cellerate RX, HyCure Hydrolyzed Collagen and Hydrolyzed Collagen/Ag Wound Gel (Hymed Group Corporation, Bethlehem, Pa.); and BIOBLANKET™ and P1076 flowable collagen (Kensey Nash Corporation, Exton, Pa.). In some embodiments, the collagen matrix is not BIOBLANKET™. In some embodiments, the collagen matrix is not COLLATAPE®.

In some embodiments, the biocompatible matrix of the present invention is flowable. Flowable biocompatible matrix, in some embodiments, can be applied to the desired site through a syringe and needle or cannula. In some embodiments, the flowable biocompatible matrix can be applied to the desired site percutaneously. In other embodiments, flowable biocompatible matrix can be applied to a surgically exposed site. In some embodiments, flowable biocompatible matrix can be applied to a tendon or ligament graft for insertion into a bone tunnel. In some embodiments, such as in a kit, the biocompatible matrix is provided as a dehydrated powder or particles, which can be made flowable upon preparation for administration. For example, a dehydrated form of the biocompatible matrix may be prepared for administration by addition to or mixing with a suitable amount of a hydrating buffer. The hydrating buffer may include a suitable amount of PDGF to be administered as part of the biocompatible matrix. The suitable amount of buffer to be added is determined by, for example, the desired concentration of PDGF, the desired concentration of collagen, the desired concentration of GAG, the desired flowability characteristic, or any suitable combination thereof.

"Flowable" refers to a physical characteristic of a substance in which the substance flows upon application of a force required to administer such substance through a cannula or like passage, yet the substance will remain substantially immobile after administration to a site in the individual to be treated, thereby providing continued treatment to the site. An exemplary device for administering a flowable substance is a syringe, in which the plunger can provide the required force that urges the flowable substance to be administered. A suitable exemplary device may further comprise a needle or other suitable cannula that allow more precise delivery and application of the flowable substance. The bore diameter, the composition, the conformation, the length, and any other suitable characteristic of the device for administration may be selected and used. A person skilled in the art understands that the selection of particular parameters of a suitable delivery device are based on the flowability characteristics of the composition. For example, relatively less flowable composition may be more suited for delivery by a device having a relatively wider cannular bore diameter and/or shorter cannula. In some embodiments, the flowable composition is delivered through a 21 G, 25 G, or 27 G needle. In some embodiments, delivery by syringe and/or needle allows delivery of the flowable composition via percutaneous injection. In some embodiments, the flowable composition can be delivered by a non-cannular device, such as a scoop, spatula, brush, or other like device, which allows the composition to be delivered to the desired location.

In some embodiments, the biocompatible matrix does not oxidize PDGF.

Biocompatible matrix, according to some embodiments, can be provided in a shape suitable for implantation (e.g., a sphere, a cylinder, or a block). In other embodiments, biocompatible matrix is moldable or extrudable. In such embodiments, the biocompatible matrix can be in the form of a paste or putty. In some embodiments, the biocompatible matrix can be provided in a predetermined shape including a block, sphere, or cylinder, or any desired shape, for example a shape defined by a mold or a site of application. Moldable biocompatible matrix can facilitate efficient placement of compositions of the present invention in and around tendons, ligaments, and/or bone, including sites of tendon or ligament attachment into or to bone, such as insertion of a tendon or ligament graft into a bone tunnel. In some embodiments, moldable biocompatible matrix can be applied to bone and/or tendons and/or ligaments with a spatula or equivalent device. In some embodiments, biocompatible matrix can be applied to tendons or ligaments by wrapping around the tendons or ligaments, such as tendon or ligament grafts.

Collagen matrices of the present invention can be made from purified collagen extracts from bovine dermis, bovine tendon (e.g., deep flexor (Achilles) tendon), or other suitable collagen sources. In some embodiments, the collagen matrix is primarily Type I collagen. In some embodiments the collagen matrix is made from a collagen slurry with any one of the following concentrations of collagen (w/v): about 4.5%, about 5%, about 6% or about 7%. In some embodiments, the collagen is soluble. A soluble collagen can dissolve shortly after its implantation, thereby introducing macroporosity into the biocompatible matrix. Macroporosity can increase the conductivity of cells (e.g. osteoblast, tenocyte) into the implant material by enhancing the access and, consequently, the remodeling activity of the cells at the implant site.

In some embodiments, the collagen comprises a soluble collagen monomer component and an insoluble collagen polymer component. In some embodies, the ratio of soluble collagen monomers to insoluble collagen polymers is about 1:10, about 1:9, about 1:8, about 1:7, about 1:6, about 1:5, about 1:4, about 1:3, about 1:2 or about 1:1.

In some preferred embodiments, the biocompatible matrix forms a porous structure comprising pores. In some embodiments, the pores have an average area ranging from about 800 µm$^2$ to about 3,000 µm$^2$, about 13,000 µm$^2$ to about 50,000 µm$^2$, about 2500 µm$^2$ to about 20,000 µm$^2$, about 3500 µm$^2$ to about 20,000 µm$^2$, 4500 µm$^2$ to about 20,000 µm$^2$, about 5000 µm$^2$ to about 19,000 µm$^2$, about 6000 µm$^2$ to about 18,000 µm$^2$, about 6000 µm$^2$ to about 15,000 µm$^2$, or about 5000 µm$^2$ to about 16000 µm$^2$. In some embodiments, the pores have an average perimeter ranging from about 100 µm to about 200 µm, about 400 µm to about 800 µm, about 200 µm to about 500 µm, about 200 µm to about 600 µm, about 300 µm to about 600 µm, or about 300 µm to about 500 µm. In some embodiments, the biocompatible matrix has an average pore area size ranging from about 4500 µm$^2$ to about 20000 µm$^2$ and an average pore perimeter size ranging from about 200 µm to about 600 µm. In some embodiments, the collagen matrix comprises pores with an average pore area size ranging from about 4500 µm$^2$ to about 20000 µm$^2$ and an average pore perimeter size ranging from about 200 µm to about 500 µm.

In some embodiments, the biocompatible matrix comprises a porous structure having multidirectional and/or interconnected pores. Porous structure, according to some embodiments, can comprise pores having diameters ranging from about 1 µm to about 1 mm, for example, at least about 5 µm, at least about 10 µm, at least about 20 µm, at least about 30 um, at least about 40 µm, or at least about 50 µm.

In some embodiments, the biocompatible matrix comprises macropores having diameters ranging from about 100 µm to about 1 mm. In another embodiment, the biocompatible matrix comprises mesopores having diameters ranging from about 10 µm to about 100 µm. In a further embodiment, the biocompatible matrix comprises micropores having diameters less than about 10 µm. Embodiments of the present invention contemplate biocompatible matrix comprising macropores, mesopores, and micropores or any combination thereof.

In other embodiments, the biocompatible matrix comprises a porous structure having pores that are not interconnected. In some embodiments, the biocompatible matrix comprises a porous structure having a mixture of interconnected pores and pores that are not interconnected.

In some embodiments, the biocompatible matrix is porous and able to absorb water in an amount ranging from about 1× to about 15× the mass of the biocompatible matrix. In some embodiments, the collagen matrix is porous and able to absorb water in an amount ranging from about 1× to about 15× the mass of the collagen matrix.

In some embodiments, the porous structure of the biocompatible matrix allows for PDGF to be released from the matrix in increased amounts. In some embodiments, the porous structure of collagen matrix (5%) releases a higher percentage of PDGF than collagen matrix (6%) or collagen matrix (7%) within a particular time, as measured in vivo or in vitro. In some embodiments, the porous structure of the biocompatible matrix allows for PDGF to be released from the matrix within about 24 hours of in vivo or in vitro administration. In some embodiments, at least about 50%, at least about 55%, at least about 60%, at least about 65%, at least about 70%, at least about 75%, at least about 80%, at least about 85%, at least about 90%, at least about 95%, about 50% to about 95%, about 60% to about 95%, about 70% to about 95%, about 80% to about 95%, about 90% to about 95%, about 50% to about 85%, about 60% to about 85%, about 70% to about 85%, or about 50% to about 80% of the PDGF is released from the matrix within about 24 hours. In some embodiments, the porous structure of the biocompatible matrix allows for PDGF to be released from the matrix within about 1 hour, about 6 hours, about 8 hours, about 12 hours, or about 48 hours of in vivo or in vitro administration. In some embodiments, at least about 50%, at least about 55%, at least about 60%, at least about 65%, at least about 70%, at least about 75%, at least about 80%, at least about 85%, at least about 90%, at least about 95%, about 50% to about 95%, about 60% to about 95%, about 70% to about 95%, about 80% to about 95%, about 90% to about 95%, about 50% to about 85%, about 60% to about 85%, about 70% to about 85%, or about 50% to about 80% of the PDGF is released within about 1 hour, about 6 hours, about 8 hours, about 12 hours, or about 48 hours. In some embodiments, the collagen matrix is COLLATAPE®. In some embodiments, the collagen matrix is a porous bovine collagen sponge similar to COLLATAPE®. In some embodiments, the biocompatible matrix comprises COLLATAPE® which allows for a higher percentage of PDGF to be released in comparison to collagen matrix (5%), collagen matrix (6%), or collagen matrix (7%).

In some embodiments, the PDGF is released into the surrounding region. In some embodiments, the PDGF is released onto an injured tendon or ligament. In some embodiments, the PDGF is released onto the surface of the bone near the point of bone-tendon or bone-ligament attachment. In some embodiments, the PDGF is released into the surrounding media.

In some embodiments, the porous structure of the biocompatible matrix allows for infiltration of cells into pores of the matrix. In some embodiments, the cells infiltrate the composition within about 3 weeks, about 2 weeks, about 1 week, about 7 days, about 6 days, about 5 days, about 4, about 3, about 2, or about 1 day(s) after exposure to the composition. In some embodiments, the cells are tenocytes. In some embodiments the cells are osteoblasts. In some embodiments, the cells are ligament cells. In preferred embodiments, the biocompatible matrix comprises COLLATAPE® with a porous structure that allows for infiltration of cells into the pores of the matrix. In some embodiments, the biocompatible matrix comprises COLLATAPE® with a porous structure that allows for a larger number of cells to infiltrate into the pores of the matrix as compared to collagen matrix (5%), collagen matrix (6%), or collagen matrix (7%). In some embodiments, the biocompatible matrix comprises collagen matrix (5%) with a porous structure that allows for a larger number of cells to infiltrate into the pores of the matrix as compared to collagen matrix (6%), or collagen matrix (7%).

In some embodiments, the biocompatible matrix has a porosity of at least about 85%, about 90%, about 92%, about 95%, about 96%, about 97%, about 98%, or about 99%.

In some embodiments, a biocompatible matrix is bioresorbable. A biocompatible matrix, in some embodiments, can be resorbed within one year of in vivo administration. In other embodiments, a biocompatible matrix can be resorbed within 1, 3, 6, or 9 months of in vivo administration. In some embodiments, the biocompatible matrix is resorbed within about 30 days, about 25 days, about 21 days, about 18 days, about 15 days, about 10-14 days, or about 10 days of in vivo administration. Bioresorbability is dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

In some embodiments, the biocompatible matrix comprises at least one calcium phosphate. In other embodiments, the biocompatible matrix comprises a plurality of calcium phosphates. In some embodiments, calcium phosphates suitable for use as a biocompatible matrix material, have a calcium to phosphorus atomic ratio ranging from 0.5 to 2.0. In some embodiments, the biocompatible matrix comprises an allograft. In some embodiments, the biocompatible matrix is for use in treating a tendon or ligament injury not involving a bone, and the matrix does not comprise a calcium phosphate or an allograft.

Calcium phosphates suitable for use as bone scaffolding materials include, but are not limited to amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxyapatite, tetracalcium phosphate (TTCP), heptacalcium decaphosphate, calcium metaphosphate, calcium pyrophosphate dehydrate, carbonated calcium phosphate, and calcium pyrophosphate.

Scaffolding Material and Biocompatible Binder

In some embodiments, the biocompatible matrix comprises a scaffolding matrix and a biocompatible binder. Biocompatible binders can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material and a binder if such material acts to promote cohesion between the combined substances and provides a framework for new tissue growth to occur, including tendon, ligament, and bone growth. See WO2008/005427 and U.S. Ser. No. 11/772,646 (U.S. Publication 2008/00274470).

Biocompatible binders, in some embodiments, can comprise, for example, collagen, elastin, polysaccharides, nucleic acids, carbohydrates, proteins, polypeptides, poly(α-hydroxy acids), poly(lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and/or copolymers and/or mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, lecithin, phosphatidylcholine derivatives, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, a pluronic acids, sodium glycerophosphate, glycogen, a keratin, silk, and/or derivatives and/or mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity can increase the osteoconductivity of the implant material by enhancing the access and, consequently, the remodeling activity of the cells (e.g. osteoclasts and osteoblasts, tenocytes) at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix.

Platelet-Derived Growth Factor

The invention provides for compositions and methods for the treatment of tendon or ligament injuries in an individual. In general, the methods of treatment comprise administering a composition comprising a biocompatible matrix and PDGF to an individual who has a tendon or ligament injury. Specifically, the methods of treatment comprise administering a composition comprising a collagen matrix and PDGF to the site of the tendon or ligament injury.

A biocompatible matrix, according to embodiments of the present invention, comprises a scaffolding matrix and PDGF. PDGF is a growth factor released from platelets at sites of injury. PDGF synergizes with VEGF to promote neovascularization, and stimulates chemotaxis and proliferation of mesenchymally-derived cells including tenocytes, osteoblasts, chondrocytes and vascular smooth muscle cells.

Compositions and methods provided by the present invention comprise a biocompatible matrix and a solution of PDGF wherein the solution is dispersed in the biocompatible matrix. In some embodiments, PDGF is present in the solution in a concentration ranging from about 0.01 mg/ml to about 10.0 mg/ml, from about 0.05 mg/ml to about 5.0 mg/ml, from about 0.1 mg/ml to about 1.0 mg/ml, or from about 0.1 mg/ml to about 2.0 mg/ml, about 0.1 mg/ml to about 0.4 mg/ml, about 0.9 mg/ml to about 1.5 mg/ml. In some embodiments, the PDGF is present in the solution at a concentration of 0.15 mg/ml. In some embodiments, the PDGF is present in the solution at a concentration of 0.3 mg/ml. In some embodiments, the PDGF is present in the solution at a concentration of 1.0 mg/ml. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml; about 0.6 mg/ml; about 0.65 mg/ml; about 0.7 mg/ml; about 0.75 mg/ml; about 0.8 mg/ml; about 0.85 mg/ml; about 0.9 mg/ml; about 0.95 mg/ml; about 1.0 mg/ml; about 1.5 mg/ml; or about 2.0 mg/ml. It is to be understood that these concentrations are simply examples of particular embodiments, and that the concentration of PDGF may be within any of the concentration ranges stated above.

Various amounts of PDGF may be used in the compositions of the present invention. Amounts of PDGF that can be used include, but are not limited to, amounts in the following ranges: about 1 µg to about 50 mg, about 10 µg to about 25 mg, about 100 µg to about 10 mg, and about 250 µg to about 5 mg.

The concentration of PDGF (or other growth factors) in embodiments of the present invention can be determined by using an enzyme-linked immunoassay as described in U.S. Pat. Nos. 6,221,625; 5,747,273; and 5,290,708, or any other assay known in the art for determining PDGF concentration. When provided herein, the molar concentration of PDGF is determined based on the molecular weight of PDGF dimer (e.g., PDGF-BB, MW about 25 kDa).

In some embodiments of the present invention, PDGF comprises PDGF homodimers and heterodimers, including PDGF-AA, PDGF-BB, PDGF-AB, PDGF-CC, PDGF-DD, and mixtures and derivatives thereof. In some embodiments, PDGF comprises PDGF-BB. In other embodiments, PDGF comprises a recombinant human PDGF, such as rhPDGF-BB.

In some embodiments, PDGF can be obtained from natural sources. In other embodiments, PDGF can be produced by recombinant DNA techniques. In some embodiments, PDGF or fragments thereof may be produced using peptide synthesis techniques known to one of skill in the art, such as solid phase peptide synthesis.

When obtained from natural sources, PDGF can be derived from biological fluids. Biological fluids, according to some embodiments, can comprise any treated or untreated fluid associated with living organisms including blood. Biological fluids can also comprise blood components including platelet concentrate, apheresed platelets, platelet-rich plasma, plasma, serum, fresh frozen plasma, and buffy coat. Biological fluids can comprise platelets separated from plasma and resuspended in a physiological fluid.

When produced by recombinant DNA techniques, a DNA sequence encoding a single monomer (e.g., PDGF B-chain or A-chain) can be inserted into cultured prokaryotic or eukaryotic cells for expression to subsequently produce the homodimer (e.g., PDGF-BB or PDGF-AA). The homodimer PDGF produced by recombinant techniques may be used in some embodiments. In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g., PDGF-AB). Commercially available recombinant human PDGF-BB may be obtained from a variety of sources.

In some embodiments of the present invention, PDGF comprises PDGF fragments. In one embodiment, rhPDGF-B comprises the following fragments: amino acid sequences 1-31, 1-32, 33-108, 33-109, and/or 1-108 of the entire B chain. The complete amino acid sequence (aa 1-109) of the B chain of PDGF is provided in FIG. 15 of U.S. Pat. No. 5,516,896. It is to be understood that the rhPDGF compositions of the present invention may comprise a combination of intact rhPDGF-B (aa 1-109) and fragments thereof. Other fragments of PDGF may be employed such as those disclosed in U.S. Pat. No. 5,516,896. In accordance with some embodiments, the rhPDGF-BB comprises at least 65% of intact rhPDGF-B (aa 1-109). In accordance with other embodiments, the rhPDGF-BB comprises at least 75%, 80%, 85%, 90%, 95%, or 99% of intact rhPDGF-B (aa 1-109).

In some embodiments of the present invention, PDGF can be in a highly purified form. Purified PDGF, as used herein, comprises compositions having greater than about 95% by weight PDGF prior to incorporation in solutions of the present invention. The solution may be prepared using any pharmaceutically acceptable buffer or diluent. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into the scaffolding matrix.

In a further embodiment, PDGF can be partially purified. Partially purified PDGF, as used herein, comprises compositions having PDGF in the context of platelet-rich plasma, fresh frozen plasma, or any other blood product that requires collection and separation to produce PDGF. Embodiments of the present invention contemplate that any of the PDGF isoforms provided herein, including homodimers and heterodimers, can be purified or partially purified. Compositions of the present invention comprising PDGF mixtures may comprise PDGF isoforms or PDGF fragments in partially purified and purified proportions. Partially purified and purified PDGF, in some embodiments, can be prepared as described in U.S. Ser. No. 11/159,533 (U.S. Publication 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate-buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In one embodiment, sodium acetate buffer is used. The buffers may be employed at different molarities, for example about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

In another embodiment, solutions comprising PDGF may be formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, more preferably about 5.5 to about 7.0, most preferably about 5.5 to about 6.5, or any value within these ranges. The pH of solutions comprising PDGF, in some embodiments, can be compatible with the prolonged stability and efficacy of PDGF or any other desired biologically active agent. PDGF is generally more stable in an acidic environment. Therefore, in accordance with some embodiments, the present invention comprises an acidic storage formulation of a PDGF solution. In accordance with some embodiments, the PDGF solution preferably has a pH from about 3.0 to about 7.0, and more preferably from about 4.0 to about 6.5. The biological activity of PDGF, however, can be optimized in a solution having a neutral pH range. Therefore, in other embodiments, the present invention comprises a neutral pH formulation of a PDGF solution. In accordance with this embodiment, the PDGF solution preferably has a pH from about 5.0 to about 8.0, more preferably about 5.5 to about 7.0, most preferably about 5.5 to about 6.5.

In some embodiments, the pH of the PDGF-containing solution may be altered to optimize the binding kinetics of PDGF to a matrix substrate. If desired, as the pH of the material equilibrates to adjacent material, the bound PDGF may become labile. The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of theprotein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors (e.g., ethylenediaminetetraacetic acid (EDTA), ethylene glycol-bis(beta-aminoethylether)-N, N,N',N'-tetraacetic acid (EGTA), aprotinin, E-aminocaproic acid (EACA), etc.) and/or other growth factors such as fibroblast growth factors (FGFs), epidermal growth factors (EGFs), transforming growth factors (TGFs), keratinocyte growth factors (KGFs), insulin-like growth factors (IGEs), bone morphogenetic proteins (BMPs), or other PDGFs including compositions of PDGF-AA, PDGF-BB, PDGF-AB, PDGF-CC and/or PDGF-DD.

Compositions Further Comprising Biologically Active Agents

Compositions and methods of the present invention, according to some embodiments, can further comprise one or more biologically active agents in addition to PDGF. Biologically active agents that can be incorporated into compositions of the present invention, in addition to PDGF, can comprise organic molecules, inorganic materials, proteins, peptides, nucleic acids (e.g., genes, gene fragments, small-interfering ribonucleic acids (siRNAs), gene regulatory sequences, nuclear transcriptional factors and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. Ser. No. 11/159,533 (U.S. Publication 20060084602). Biologically active compounds that can be incorporated into compositions of the present invention, in some embodiments, include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, calcitonin mimetics, statins, statin derivatives, fibroblast growth factors, insulin-like growth factors, growth differentiating factors, and/or parathyroid hormone. Additional factors for incorporation into compositions of the present invention, in some embodiments, include protease inhibitors, as well as osteoporotic treatments that decrease bone resorption including bisphosphonates, and antibodies to the NF-kB (RANK) ligand.

Standard protocols and regimens for delivery of additional biologically active agents are known in the art. Additional biologically active agents can be introduced into compositions of the present invention in amounts that allow delivery of an appropriate dosage of the agent to the damaged tendon and/or the site of tendon attachment. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition for attaching tendon or ligament to or into bone according to some embodiments, further comprises one or more bone grafting materials including, for example, autologous bone marrow, autologous platelet extracts, allografts, synthetic bone matrix materials, xenografts, and derivatives thereof.

Tendons, Ligaments, and Bones Treated

Tendons which may be treated by the methods of the invention include any tendon. Non-limiting examples of tendons include patellar tendon, anterior tibialis tendon, Achilles tendon, Hamstring tendon, semitendinosus tendon, gracilis tendon, abductor tendon, adductor tendon, supraspinatus tendon, infraspinatus tendon, subscapularis tendon, teres minor tendon (rotator cuff complex), flexor tendon, rectus femoris tendon, tibialis posterior tendon, and quadriceps femoris tendon. In some embodiments, the tendon is selected from the group consisting of patellar tendon, anterior tibialis tendon, Achilles tendon, Hamstring tendon, semitendinosus tendon, gracilis tendon, abductor tendon, and adductor tendon. In some embodiments, the tendon is selected from the group consisting of supraspinatus tendon, infraspinatus tendon, subscapularis tendon, teres minor tendon (rotator cuff complex), flexor tendon, rectus femoris tendon, tibialis posterior tendon, and quadriceps femoris tendon. In some embodiments, the tendon is not selected from the group consisting of supraspinatus tendon, infraspinatus tendon, subscapularis tendon, teres minor tendon (rotator cuff complex), flexor tendon, rectus femoris tendon, tibialis posterior tendon, and quadriceps femoris tendon.

Ligaments which may be treated by the methods of the invention include any ligaments. Non-limiting examples of ligaments include anterior cruciate ligament, lateral collateral ligament, posterior cruciate ligament, medial collateral ligament, cranial cruciate ligament, caudal cruciate ligament, cricothyroid ligament, periodontal ligament, suspensory ligament of the lens, anterior sacroiliac ligament, posterior sacroiliac ligament, sacrotuberous ligament, sacrospinous ligament, inferior pubic ligament, superior pubic ligament, suspensory ligament (e.g., penis or breast), palmar radiocarpal ligament, dorsal radiocarpal ligament, ulnar collateral ligament, or radial collateral ligament.

Bones which may be treated by compositions and methods of the present invention include any bones which are attachment sites for tendons or ligaments, and include, but are not limited to, the tibia, femur, and humerus.

Methods for Treatment of Tendon or Ligament Injuries not Involving a Bone

The present invention provides compositions and methods for the treatment of tendon or ligament injuries. The methods for treatment may comprise treatment of injured tendons or ligaments not involving a bone, such as severed tendons/ligaments, ruptured tendons/ligaments, tendons/ligaments exhibiting tearing, delamination, or any other strain or deformation.

In some embodiments, a method for treatment of tendon or ligament injuries is directed to administering a composition of the present invention to an injured tendon or ligament. In some embodiments, the injured tendon or ligament may be physically stabilized for the treatment. For example, the injured tendon or ligament may be sutured by a modified Mason Allen suture design, or any other suitable suture. Such stabilizing methods may be preferred in some embodiments, as the damaged ends of the tendon or ligament may not permit direct surgical repair or reconnection of the ends. As a result, the stabilizing suture may be positioned distal to one or more of the injured ends.

As a result of this stabilizing suture, the injured tendon or ligament is positioned such that the injured ends of the tendon or ligament are substantially re-approximated. In some embodiments, a suitably-sized gap may remain between the re-approximated ends, thereby allowing introduction of a flowable composition into the gap volume, thereby bridging or filling-in the gap. In some embodiments, the administered composition can be substantially immobile in the gap. In some embodiments, this substantial immobility may be aided or provided by a wrap, or other suitable device, to surround or bind the re-approximated ends with the composition, thereby enclosing the injury and the composition therein.

The composition of the present invention can be flowable. In this manner, the flowable composition can be more precisely delivered to the injured tendon or ligament site. A syringe, or other suitable device, can be used to administer the composition of the present invention. The syringe may further include a needle or other suitable cannula that allows more precise delivery of the composition. The configuration of the syringe and/or cannula, such as its bore, size, length, etc. can be configured depending on the desired volume of composition to be delivered, or the flowability characteristics of the composition. Another advantageous characteristic of the composition of the present invention is that the composition, once delivered, can remain substantially immobile at its delivery site. In some embodiments, the flowable composition is delivered through a 21 G, 25 G, or 27 G needle. In some embodiments, delivery by syringe and/or needle allows delivery of the flowable composition via percutaneous injection. In some embodiments, the flowable composition can be delivered by a non-cannular device, such as a scoop, spatula, brush, or other like device, which allows the composition to be delivered to the desired location.

Still another advantageous feature of the composition in one embodiment of the present invention is that its flowable characteristics allow the composition to access and fill-in regions of the injury that may be normally difficult to access. For example, a ruptured tendon or ligament may be significantly frayed at the injured ends, thereby making direct surgical repair difficult. Furthermore, such damaged ends may contain many small, relatively inaccessible regions, such as crevices and other interstitial regions. The flowable composition of the present invention can be administered so that it will flow into, and thus substantially fill-in, such regions, thus allowing and promoting a more effective repair and revascularization of the injury.

In some embodiments of the present invention, the method may be performed using arthroscopic techniques, endoscopic techniques, laparoscopic techniques, or any other suitable minimally-invasive techniques.

In some embodiments, the method for treatment of a tendon or ligament injury not involving a bone in an individual comprises administering to an affected site of the injury of the individual an effective amount of a composition comprising: a biocompatible matrix and PDGF, wherein the biocompatible matrix comprises pores, wherein the biocompatible matrix has a porosity of at least about 80%, and wherein at least about 50% of the PDGF is released within about 24 hours. In some embodiments, the method for treatment of a tendon or ligament injury not involving a bone in an individual comprises administering to the individual an effective amount of a composition comprising: a biocompatible matrix and PDGF, wherein the biocompatible matrix comprises pores, wherein the biocompatible matrix has a porosity of at least about 80%, and wherein at least about 50% of the PDGF is released within about 24 hours, wherein the PDGF is present as a solution comprising PDGF, wherein the concentration of PDGF in the solution is about 0.1 mg/ml to about 2.0 mg/ml. In some embodiments, the concentration of PDGF in the solution is about 1.0 mg/ml. In some embodiments, the biocompatible matrix comprises a cross-linked collagen and glycosaminoglycan matrix. In some embodiments, at least about 60% of the PDGF is released within about 24 hours. In some embodiments, at least about 70% of the PDGF is released within about 24 hours. In some embodiments, at least about 80% of the PDGF is released within about 24 hours. In some embodiments, the biocompatible matrix has a porosity of at least about 85%. In some embodiments, the biocompatible matrix has a porosity of at least about 90%. In some embodiments, the biocompatible matrix has a porosity of at least about 92%. In some embodiments, the composition is flowable. In some embodiments, the biocompatible matrix is Integra Flowable Wound Matrix. In some embodiment, the treatment is of a tendon. In some embodiments, the treatment is of a ligament.

The present invention also provides methods of treating Achilles tendon injuries. In one embodiment, a method for treating Achilles tendon injuries comprises providing a biocompatible matrix and PDGF, wherein the biocompatible matrix is flowable.

The present invention also provides compositions and methods for treating any other suitable tendon injury, including, but are not limited to, tendons of the subscapularis, supraspinatus, infraspinatus, teres minor, rectus femoris, tibialis posterior, quadriceps femoris, biceps brachii, as well as the Achilles Tendon, patellar tendon, abductor and adductor tendons, or other tendons of the hip, the common extensor tendon, common flexor tendon, flexor digitorum superficialis tendons, extensor digitorum and extensor minimi tendons, or other tendons of the arm and hand.

The present invention also provides compositions and methods for treating any other suitable ligament injury, including, but are not limited to anterior cruciate ligament, lateral collateral ligament, posterior cruciate ligament, medial collateral ligament, cranial cruciate ligament, caudal cruciate ligament, cricothyroid ligament, periodontal ligament, suspensory ligament of the lens, anterior sacroiliac ligament, posterior sacroiliac ligament, sacrotuberous ligament, sacrospinous ligament, inferior pubic ligament, superior pubic ligament, suspensory ligament (e.g., penis or breast), palmar radiocarpal ligament, dorsal radiocarpal ligament, ulnar collateral ligament, or radial collateral ligament.

Methods for Tendon to Bone or Ligament to Bone Attachment

The present invention provides methods for attaching or reattaching a tendon or a ligament into/to a bone and for strengthening of tendon or ligament attachment to bone. The methods for attachment may comprise tendon or ligament integration or reintegration with bone at an interface between a tendon and a bone and a ligament and a bone. In some embodiments, the methods for attaching a tendon or a ligament to or into a bone comprises providing a composition comprising a PDGF solution disposed in a biocompatible matrix and applying the composition at an interface between a tendon/ligament and a bone.

In some embodiments, a method for attachment comprises providing a composition comprising a PDGF solution disposed in a biocompatible matrix, wrapping around a detached tendon, inserting the composition and the tendon into a tunnel that is drilled in the bone, and attaching the tendon to the bone with sutures.

In some embodiments, a method for attachment comprises providing a composition comprising a PDGF solution disposed in a biocompatible matrix, wrapping around a detached ligament, inserting the composition and the ligament into a tunnel that is drilled in the bone, and attaching the ligament to the bone with sutures.

In some embodiments, a method for attachment comprises providing a composition comprising a biocompatible matrix, wrapping around a detached tendon, inserting the composition and the tendon into the bone, injecting a PDGF solution into a tunnel that is drilled in the bone, and attaching the tendon to the bone with sutures.

In some embodiments, a method for attachment comprises providing a composition comprising a biocompatible matrix, wrapping around a detached ligament, inserting the composition and the ligament into the bone, injecting a PDGF solution into a tunnel that is drilled in the bone, and attaching the ligament to the bone with sutures.

In some embodiments, the PDGF solution can be injected into the tunnel adjacent to the implant site of the tendon wrapped with collagen matrix. In some embodiments, the PDGF solution can be injected into the medial side of the bone tunnel. In some embodiments, the PDGF solution can be injected into the lateral side of the bone tunnel. In some embodiments, the PDGF solution can be injected at single point of the bone tunnel perimeter. In other embodiments, the PDGF solution can be injected at multiple points of the bone tunnel perimeter. For example, the injection can be made at the ¼, ½, ¾, and full circumference of the tunnel opening.

In some embodiments, the concentration of the PDGF solution is about 0.1 mg/ml to about 2.0 mg/ml. In some embodiments, the concentration of the PDGF solution is about 0.1 mg/ml to about 0.5 mg/ml. In some embodiments, the concentration of PDGF solution is about 0.15 mg/ml. In other embodiments, the concentration of the PDGF solution is about 0.3 mg/ml.

The present invention also provides methods for attaching a tendon into a bone in an individual for anterior cruciate ligament reconstruction comprising administering to said individual an effective amount of a composition comprising a biocompatible matrix and PDGF at the interface between the tendon and the bone. In some embodiments, a method for anterior cruciate ligament reconstruction comprises providing a composition comprising a PDGF solution disposed in a biocompatible matrix, wrapping around a long flexor tendon detached from its femoral insertion on the lateral side, inserting the composition and the tendon into a tunnel that is drilled obliquely though the tibia metaphysic, and attaching the long flexor tendon to the medial cortex of the tibia with sutures.

In some embodiments, a method for anterior cruciate ligament reconstruction comprises providing a composition comprising a biocompatible matrix, wrapping around a long flexor tendon detached from its femoral insertion on the lateral side, inserting the composition and the tendon into a tunnel that is drilled obliquely though the tibia metaphysic, injecting a PDGF solution into the bone tunnel, and attaching the long flexor tendon to the medial cortex of the tibia with sutures.

In some embodiments, the present invention also provides methods for the attachment or reattachment of a tendon to bone in rotator cuff injuries. Rotator cuff injuries and rotator cuff injuries treatment with an open repair method, a mini-open repair method, and an all-arthroscopic repair method are discussed in WO2008/005427 and U.S. Ser. No. 11/772,646 (U.S. Publication 2008/0027470). These references are hereby incorporated by reference in their entireties. In some embodiment, a method for treating rotator cuff injuries comprises providing a composition comprising a PDGF solution disposed in a biocompatible matrix and applying the composition to at least one site of tendon reattachment on the humeral head. In some embodiments, applying the composition to at least one site of tendon reattachment can comprise molding the composition to the contours of the reattachment site on the humeral head. A composition, for example, can be molded into a channel formed on a surface of the humeral head for receiving the detached tendon. The composition may be applied to the vicinity of the insertion site of the tendon into bone to further strengthen the attachment.

In some embodiments, a method for treating rotator cuff tears further comprises disposing at least one anchoring means, such as a bone anchor in the humeral head, wherein the bone anchor further comprises a PDGF composition, and coupling at least one detached tendon to the bone anchor. In embodiments of the present invention, tendons can be secured to bone anchors through sutures.

In some embodiments of the present invention, the method may be performed using arthroscopic techniques, endoscopic techniques, laparoscopic techniques, or any other suitable minimally-invasive techniques.

PDGF solutions and biocompatible matrices suitable for use in compositions, according to embodiments of methods of the present invention, are consistent with those provided hereinabove.

In some embodiments, the method for attachment of a tendon or ligament to or into a bone in an individual comprises administering to an affected site of the individual an effective amount of a composition comprising: a biocompatible matrix and PDGF, wherein the biocompatible matrix comprises pores, wherein the biocompatible matrix has a porosity of at least about 80%, and wherein at least about 50% of the PDGF is released within about 24 hours. In some embodiments, the PDGF is present as a solution comprising PDGF, wherein the concentration of PDGF in the solution is about 0.1 mg/ml to about 2.0 mg/ml. In some embodiments, the concentration of PDGF in the solution is about 0.1 to about 0.4 mg/ml. In some embodiments, the concentration of PDGF in the solution is about 0.15 mg/ml. In some embodiments, the concentration of PDGF in the solution is about 0.3 mg/ml. In some embodiments, the biocompatible matrix comprises a cross-linked collagen matrix. In some embodiments, the biocompatible matrix comprises a cross-linked collagen and glycosaminoglycan matrix. In some embodiments, at least about 60% of the PDGF is released within about 24 hours. In some embodiments, at least about 70% of the PDGF is released within about 24 hours. In some embodiments, at least about 80% of the PDGF is released within about 24 hours. In some embodiments, the biocompatible matrix has a porosity of at least about 85%. In some embodiments, the biocompatible matrix has a porosity of at least about 90%. In some embodiments, the biocompatible matrix has a porosity of at least about 92%. In some embodiments, the biocompatible matrix is COLLATAPE®. In some embodiments, the treatment is of a tendon to bone attachment. In some embodiments, the treatment is of a ligament to bone attachment.

Sutures

The sutures used in the methods of the invention herein, or included in the kits herein, may comprise PDGF. PDGF may be soaked into or coated onto sutures by a solution comprising PDGF. In some embodiments, the PDGF is present in the solution at any concentration of about 5.0 to about 20.0 mg/ml, for example about 7.5 to about 15 mg/ml, for example, about 10 mg/ml.

The sutures used in the methods of the invention herein, or included in the kits herein, can be resorbable or non-resorbable in vivo. The resorption process involves degradation and elimination of the original material through the action of body fluids, enzymes, or cells. The resorbed sutures may be used by the host in the formation of the new tissue, or it may be other-wise re-utilized by an individual, or it may be excreted. The sutures can be made of synthetic or natural fibers, or combination of both.

Kits of the Invention

In another aspect, the present invention provides a kit comprising a first container comprising a PDGF solution and a second container comprising a biocompatible matrix.

In some embodiments, provided is a kit for treatment of a tendon or ligament injury not involving a bone in an individual comprising administering a first container comprising a biocompatible matrix and a second container comprising a PDGF solution, wherein the biocompatible matrix comprises pores, wherein the biocompatible matrix has a porosity of at least about 80%, and wherein at least about 50% of the PDGF is released within about 24 hours.

In other embodiments, provided is a kit for attaching a tendon or a ligament to a bone in an individual comprising administering a first container comprising a biocompatible matrix and a second container comprising a platelet-derived growth factor (PDGF) solution, wherein the biocompatible matrix comprises pores, wherein the biocompatible matrix has a porosity of at least about 80%, and wherein at least about 50% of the PDGF is released within about 24 hours.

In some embodiments, the biocompatible matrix is dehydrated. In some embodiments, the solution comprises a predetermined concentration of PDGF. The concentration of PDGF, in some embodiments, can be predetermined according to the nature of the tendon or ligament injury being treated. In some embodiments, the biocompatible matrix comprises a predetermined amount according to the nature of the tendon or ligament injury being treated. In some embodiments, the biocompatible matrix comprises a predetermined amount according to the nature of the tendon/ligament and the bone being treated.

In some embodiments, the biocompatible matrix comprises a cross-linked collagen. In some embodiments, the biocompatible matrix comprises a soluble collagen. In some embodiments, the biocompatible matrix comprises a cross-linked collagen and a glycosaminoglycan. In some embodiments, the biocompatible matrix comprises a cross-linked collagen and chondroitin sulfate.

In some embodiments, the present invention provides a kit comprising a first container comprising a PDGF solution, a second container comprising a biocompatible matrix, and a syringe. A syringe, in some embodiments, can facilitate dispersion of the PDGF solution in the biocompatible matrix for application at a surgical site, such as a site of tendon or ligament attachment to bone. The kit may also contain instructions for use.

The following examples are provided for illustrative purposes only and are not intended to limit the scope of the invention in any manner.

EXAMPLES

Example 1: Structural Characterization of Various Collagen Matrices

Four collagen matrices were studied to determine differences in the fine structure and porosity. The collagen matrices were obtained from Kensey Nash Coporation. The matrices were made from purified collagen extracts from bovine dermis, which is a source primarily of Type I collagen. The matrices are made from collagen slurries with different concentrations of collagen, 4.5%, 5%, 6% and 7% (w/v). The dry collagen matrices (4.5%, 5%, 6%, and 7%) were punched into 5 mm disks after flushing with liquid nitrogen. Disks were mounted on a stub in three different orientations (top up, bottom up, and side up), coated with gold-palladium, and examined by scanning electron microscopy (SEM).

The SEM images revealed that there were open pores on the surface of collagen matrix (4.5%) and collagen matrix (5%). The SEM images revealed a dense lamina with smaller pores on the surface of collagen matrix (6%) and collagen matrix (7%). Although each of the collagen matrices appeared to be porous, based upon SEM images of cross-sectional longitudinal slices, collagen matrix (5%) appeared to have the greatest overall porosity as assessed by SEM. The pores in the collagen matrices appeared to not be homogeneously distributed and in some areas there are no pores at all.

The SEM images were analyzed using ImageJ software for determination of both pore area size and perimeter size.

ImageJ is an image analysis program created by Wayne Rasband at the National Institutes of Health (world wide web at rsb.info.nih.gov/ij). To use the program for image analysis, the appropriate parameters needed to be chosen and set. From the "analyze" menu, the scale from each SEM image was inputted into program to set the "scale" parameter. Next, "area" and "perimeter" were chosen for the measurement parameters. Ten pores from each image were randomly selected, measurements taken and averaged for both area size and perimeter size. Results for each image were recorded. Table 1 shows the results from one analysis.

TABLE 1

|  | Side A | Cross-section | Side B |
|---|---|---|---|
|  | Area ($\mu m^2$) | | |
| Collagen (4.5%) | 6813 ± 2854 | 8005 ± 2135 | 10505 ± 4689 |
| Collagen (5%) | 11286 ± 4149 | 10591 ± 4016 | 11555 ± 6667 |
| Collagen (6%) | 6206 ± 2159 | 13643 ± 6642 | 4779 ± 1706 |
| Collagen (7%) | 4369 ± 3183 | 7993 ± 3113 | 2342 ± 998 |
|  | Perimeter ($\mu m$) | | |
| Collagen (4.5%) | 308 ± 65 | 338 ± 38 | 393 ± 94 |
| Collagen (5%) | 445 ± 99 | 417 ± 109 | 406 ± 110 |
| Collagen (6%) | 255 ± 48 | 428 ± 111 | 258 ± 50 |
| Collagen (7%) | 445 ± 77 | 344 ± 70 | 180 ± 36 |

Collagen matrix (5%) appeared to have the most porous structure and the pore area size was the largest from both Side A and Side B views as analyzed by the ImageJ software.

Example 2: Cumulative PDGF Release Analysis of Various Collagen Matrices

Cumulative PDGF release from the different collagen matrices was analyzed. Collagen matrices were obtained from Kensey Nash Corporation and are the same as described above in Example 1. Collagen matrices (8 mm disks) of each type, 5%, 6%, and 7%, were impaled on a 27½ G needle, hydrated with 80 µl of 0.3 mg/ml rhPDGF-BB and the samples were incubated for 10 min at room temperature. The collagen disks were then placed in a 2 ml microtube and 2 ml elution buffer (MEM containing 2% fetal bovine serum) was added to release the rhPDGF-BB. Triplicate samples were used for each measurement. Control samples consisted of adding 80 µl of rhPDGF-BB to 2 ml of elution buffer. The microtubes were shaken on an orbital shaker in a 37° C. incubator. At 10 min, 1 hr, 8 hr, and 24 hr, the elutant was removed from each tube and stored at 2-8° C. An equal volume of fresh elution buffer was added to each tube. The stored elutants of each collagen matrix were assayed for rhPDGF-BB using the DuoSet ELISA (R & D System) kit according to the manufacturer's instructions.

Collagen matrix (5%) released rhPDGF-BB with similar kinetics compared to collagen matrix (6%) and collagen matrix (7%) (FIG. 1). The release kinetics were characterized by an initial rapid, bolus release of rhPDGF-BB in the first 10 minutes followed by a slower, steady release over the remaining 23 hour study period. Although the release kinetics were similar, the initial bolus and total amount of PDGF released from collagen matrix (5%) was greater than either of collagen matrix (6%) or collagen matrix (7%).

Figure 2:
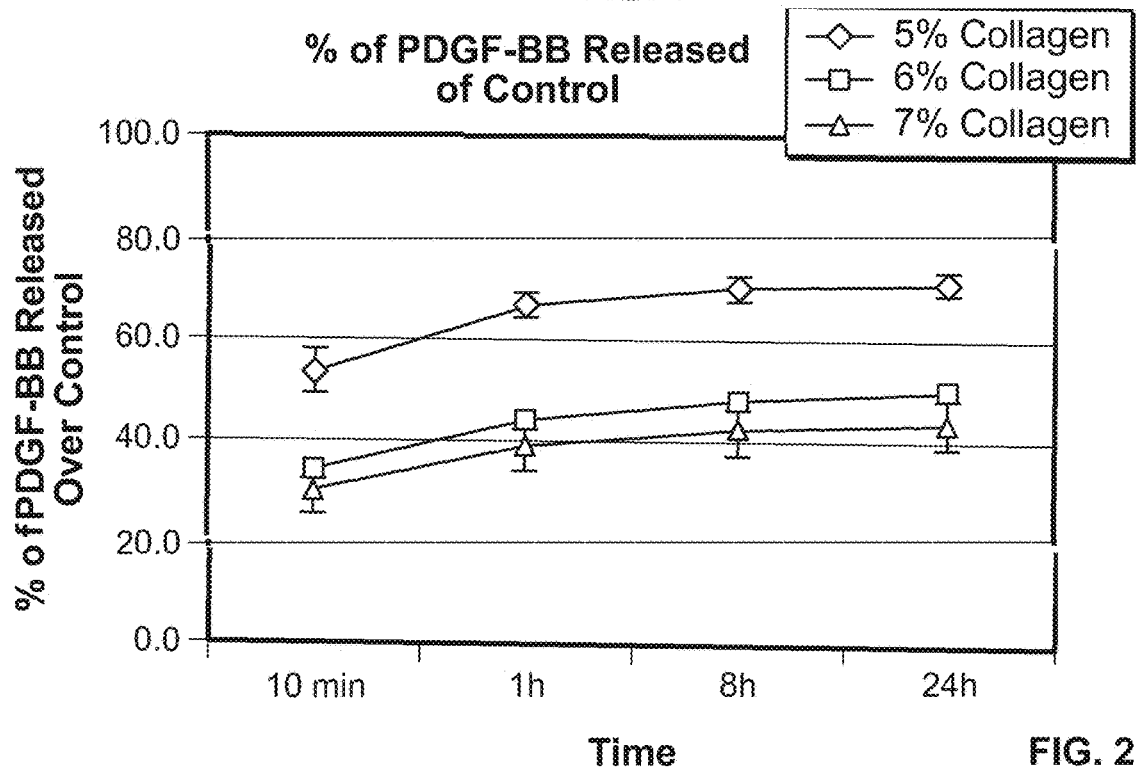
FIG. 2 depicts the percentage of rhPDGF-BB released from different collagen matrices over 24 hours.

The percent release of rhPDGF-BB from the collagen matrices was compared to control (rhPDGF-BB in elution buffer alone). The results showed that, as above, collagen matrix (5%) had a faster and larger release of PDGF than collagen matrix (6%) or collagen matrix (7%). (FIG. 2) The results of this study are also shown in Table 2.

TABLE 2

|  | Percent PDGF Release Over Control | | | |
|---|---|---|---|---|
|  | 10 min | 1 hr | 8 hr | 24 hr |
| Collagen (5%) | 53.5 ± 4.3 | 66.5 ± 4.3 | 70.2 ± 1.6 | 71.5 ± 1.5 |
| Collagen (6%) | 34.1 ± 1.1 | 44.1 ± 0.9 | 48.0 ± 1.4 | 50.0 ± 1.3 |
| Collagen (7%) | 30.3 ± 4.6 | 39.2 ± 5.1 | 42.4 ± 4.9 | 43.5 ± 4.8 |

Example 3: Biopotency Study of PDGF Release from Various Collagen Matrices

Figure 3:
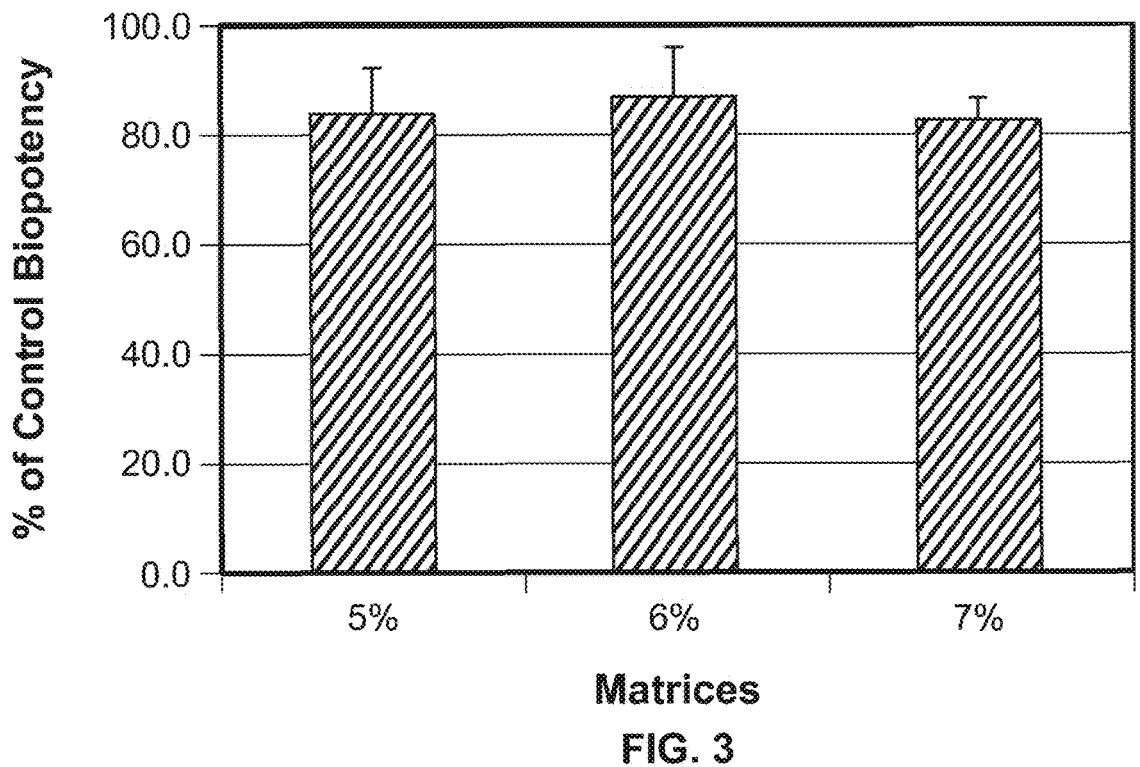
FIG. 3 depicts the biopotency of rhPDGF-BB after release from the different collagen matrices.

The biopotency of PDGF released from the different collagen matrices was assessed in cell proliferation assays. Samples were prepared following a modification of the protocol described above in Example 2. The elution buffer was changed to D-MEM containing 2% calf serum. Duplicate samples for each material taken at the one hour time point were used. The concentration of rhPDGF-BB was determined by DuoSet ELISA assay, and the results were used as a reference for diluting the samples to a concentration of 1 µg/ml. rhPDGF-BB at 0.3 mg/ml was used as a reference standard and applied to all plates. Each sample was loaded into a 96-well microtiter plate (black wall and clear bottom) using a starting concentration of 1 µg/ml and then were serially diluted 1.667-fold across the same row. Approximately $10^4$ NIH 3T3 cells were added to each well except for the last column on each plate, which was used as a blank control. After 48 hours culture, bromodeoxyuridine (BrdU) label was added to each plate. After another 24 hours culture, a BrdU cell proliferation assay was conducted according to the manufacturer's instructions.

rhPDGF-BB released from each matrix measured in a NIH 3T3 cell proliferation assay demonstrated that the biological activity of the released PDGF was conserved for the three matrices analyzed. (FIG. 3).

Example 4: Study of Stability of PDGF Released from Collagen Matrices

The stability of rhPDGF released from collagen matrices was studied. Collagen matrices (8 mm disks) of each type, (5%, 6%, and 7%), were impaled on a 27½ G needle and hydrated with 50 µl of 1.0 mg/ml rhPDGF-BB. Each sample was incubated in a microtube filled with 0.4 ml elution buffer (20 mM sodium acetate+0.25 N sodium chloride) for 1 hr. The released PDGF was then analyzed by size exclusion HPLC. Triplicate measurements were taken. No significant profile shift was found for the rhPDGF-BB released from collagen matrices, demonstrating the stability of the PDGF released from the collagen matrices.

Example 5: Study of Tenocytes Infiltration of Various Collagen Matrices

The ability of tenocytes to infiltrate into different collagen matrices was evaluated. Collagen matrices were obtained from Kensey Nash Corporation and were made from collagen slurries with collagen concentrations of 5%, 6% and 7% (w/v) as described herein. The collagen sheets (1.5-2.0 mm thick) were punched into 8 mm diameter disks for the in vitro cell migration studies.

Primary ovine tenocytes (<4 cell passages) were isolated from ovine flexor tendon. The cells were cultured in growth medium (D-MEM/P-12 containing 10% fetal bovine serum (PBS)) and switched to basic medium (D-MEM/P-12 containing 2% PBS) 12 hours prior to starting the study.

50 µl (50,000 cells) of the tenocyte cell suspension in basic medium was added to each collagen disk sample. After 1 hr incubation at 37° C. and 5% $CO_2$ atmosphere without medium emersion, the cell-seeded disks were transferred to a 24-well plate pre-filled with 2 ml of basic medium alone or in combination with rhPDGF-BB (30 ng/ml). After 12 h of static culture, the plates with cell-seeded disks were placed on an orbital shaker (60 rpm) in the incubator. Medium changes were provided every 48 h. On day 6, quadruplicate samples from each collagen matrix and treatment were taken for histological assessment.

Generally, the histological assessment was similar to the following description. After six days' culture, the cell culture media was removed from each well and replaced with 4% phosphate buffered formalin (PBF). The samples were fixed in PBF for approximately 30 minutes at room temperature (RT). The samples were placed under vacuum at RT for a period of no less than 1 hour to complete cellular fixation. Using a shaker platform and a vacuum chamber, the specimens were then dehydrated over a period of approximately 5.5 hours through an increasing series of ethanol concentrations (70%-80%-95%-100%) at RT, cleared in 100% xylene over a period of 2 hours at RT, and infiltrated in paraffin wax for a period of no less than 2 hours. Samples from each treatment group and matrix were then embedded. The embedded specimens were removed from their embedding moulds, "trimmed" and "faced" with a rotary microtome to expose outermost surface of all specimens, and then placed in the freezer overnight. Using a rotary microtome, a warmed water bath, and pre-labeled glass microscope slides, sections (2 sections per slide) were taken at 4-6 microns at 3-4 levels approximately 100-150 microns apart. Slides were dried overnight in an oven at 60° C. Finally slides were stained with Hoescht fluorescence stain and viewed.

The results showed that tenocytes infiltrated into collagen matrix (5%) with PDGF, while tenocytes did not appeared to infiltrate into collagen matrix (6%) and collagen matrix (7%). For collagen matrix (6%) and collagen matrix (7%) samples most of the tenocytes accumulated at the edge of the disks. Therefore it appeared that the greater porosity of collagen matrix (5%) allowed for a higher number of infiltrating cells into the collagen matrix.

Example 6: Treatment of Achilles Tendon Injury With Collagen/PDGF Compositions An exemplary study, as described below, was used to evaluate the efficacy of a composition and methods in accordance with the present invention. The present invention includes compositions, and methods of use thereof, that comprise an rhPDGF-BB solution mixed with a collagen matrix. For example, the collagen matrix is a flowable collagen matrix and comprises a cross-linked bovine tendon collagen and glycosaminoglycan (GAG) matrix. Flowable-compositions are readily provided to the injury site by a syringe or other suitable means.

Sheep, or other suitable test subjects, were used in this exemplary study as a model for human Achilles tendon repair. Sheep are particularly suitable due to the similarity of the sheep Achilles tendon size to the human Achilles tendon. Additionally, sheep are of sufficient size to allow for standard orthopedic techniques and placement of the composition. The sheep used in this study were skeletally mature (as determined by age [3.5 years and older] and dental wear) with normal ambulation, and weighed at least 120 lbs and acclimated at the time of surgery. Sheep were fed and watered in accordance with a standard small ruminant diet. Food and water were withheld for appropriate study related events such as anesthesia.

The study used three treatment groups (n=8/group) in which the following test compositions were provided and applied to the injury site of acute Achilles tendon transection: (1) flowable collagen matrix in buffer, (2) flowable collagen matrix in buffer with 0.3 mg/mL (150 µg) rhPDGF-BB, and (3) flowable collagen matrix in buffer with 1.0 mg/mL (500 µg) rhPDGF-BB. Other suitable treatment groups are used such as, for example, those that use compositions with other suitable concentrations of rhPDGF-BB.

An exemplary flowable collagen matrix is the Integra™ Flowable Wound Matrix (IFWM) of Integra LifeSciences Corporation, Plainsboro, N.J. Other suitable matrices known in the art can also be used.

Experimental Overview

The Achilles tendons of sheep enrolled into this study were transected, followed by immediate repair. The sheep were divided into three exemplary test groups (n=8/group) in which the following compositions were used: 1) flowable collagen matrix in 20 mM sodium acetate buffer (pH 6.0+/−0.5), placed at the re-approximated tendon ends (stabilized with a modified Mason Allen suture design) (control), 2) flowable collagen matrix, in 20 mM sodium acetate buffer containing 0.3 mg/ml rhPDGF-BB, placed at the re-approximated tendon ends (stabilized with a modified Mason Allen suture) and 3) flowable collagen matrix in 20 mM sodium acetate buffer containing 1.0 mg/ml rhPDGF-BB, placed at the re-approximated tendon ends (stabilized with a modified Mason Allen suture). Suturing material was used, such as #1 Ethilon nylon suture (Ethicon Endo-Surgery, Inc, Cincinnati, Ohio). Biomechanical performance and histological response of asimulated Achilles rupture and reattachment were determined. The treatment allocations and number of animals for both the biomechanical performance and the histological response tests are outlined in Table 3.

TABLE 3

Treatment allocations

| Treatment Group | | Animals (n) | rhPDGF-BB | Endpoint |
|---|---|---|---|---|
| 1 | Collagen Flowable Wound Matrix(IFWM) + Buffer | 8 | 0 | Biomechanics (N = 6)/ Histology (N = 2) |
| 2 | IFWM + 0.3 mg/ml rhPDGF-BB | 8 | 0.3 mg/ml | Biomechanics (N = 6)/ Histology (N = 2) |
| 3 | IFWM + 1.0 mg/ml rhPDGF-BB | 8 | 1.0 mg/mL | Biomechanics (N = 6)/ Histology (N = 2) |

Contralateral Achilles tendons from treatment group 1 will also be collected for biomechanics (n = 6) and histology (n = 2)

Following placement of the test materials, the incision was closed using standard surgical techniques and a splint placed on the lower foot to prevent knuckling during ambulation. During the week post-surgery, the surgical site was monitored for abnormal healing or wound dehiscence. The animal was allowed to ambulate normally for 8 weeks and had ultrasound evaluations performed at 2, 4 and 8 weeks post-operative. Eight weeks post-surgical, all animals were euthanized and the Achilles tendon was collected, including the proximal and distal musculotendinous junctions, for histological and biomechanical assessment. Normal, unoperated tendons, and their musculotendinous junctions, were collected from the contralateral hind limb of control animals (i.e., flowable collagen wound matrix alone) so that histologic and biomechanical testing may be performed for normal, untreated tendons. The skin from the initial surgical site and contralateral controls are also taken for histological evaluation.

Surgical Protocol

On the day of surgery, an IV injection consisting of Diazepam (0.22 mg/kg) and Ketamine (10 mg/kg) was given for induction of general anesthesia. A cuffed endotracheal tube was placed and general anesthesia was maintained with isofluorane (1.5% to 3.0%) in 100% oxygen (2 L/min) through a rebreathing system. The animal was placed on a ventilator to assist respiration. A stomach tube could be placed.

With the animal in left lateral recumbency, the wool was removed from the right leg to provide adequate access to prepare the site for surgery. The skin over the right ankle joint was prepared for aseptic surgery using alternating scrubs of povidone-iodine (Betadine) and alcohol. The surgical site was then draped for aseptic surgery. An incision was made over the lateral aspect of the leg and then deepened through the subcutaneous tissues to expose the tendon at its insertion site on the calcaneus. The larger branch of the gastrocnemius tendon was then isolated. The Achilles tendon insertion to the calcaneus was palpated and marks were placed at 2, 4, and 6 cm from the insertion site with a sterile marker.

Prior to surgery, the matrix and appropriate buffer solution (20 mM sodium acetate buffer, pH 6.0+/−0.5)+/− rhPDGF-BB, were combined by adding 6.0 cc of the buffer+/−rhPDGF-BB, to 3.0 cc of the flowable collagen material (IFWM) (2:1 v/v), using the supplied, labeled sterile syringes containing the dry collagen and buffer+/− rhPDGF-BB. The materials were combined by removing the tip cap from the syringe containing the rhPDGF-BB and replacing it with the supplied, sterile luer lock connector to which the syringe containing the dry collagen was then connected. Hydration of the collagen matrix was accomplished by dispensing all buffer+/− rhPDGF-BB into the collagen syringe and mixing by depressing the plungers back and forth at least 15 times until the mixture appears homogeneous and all the material can be moved back and forth easily between syringes. The hydrated flowable collagen matrix was aliquoted into 0.5 cc volumes in sterile containers and stored at 4° C. until use.

Figure 4:
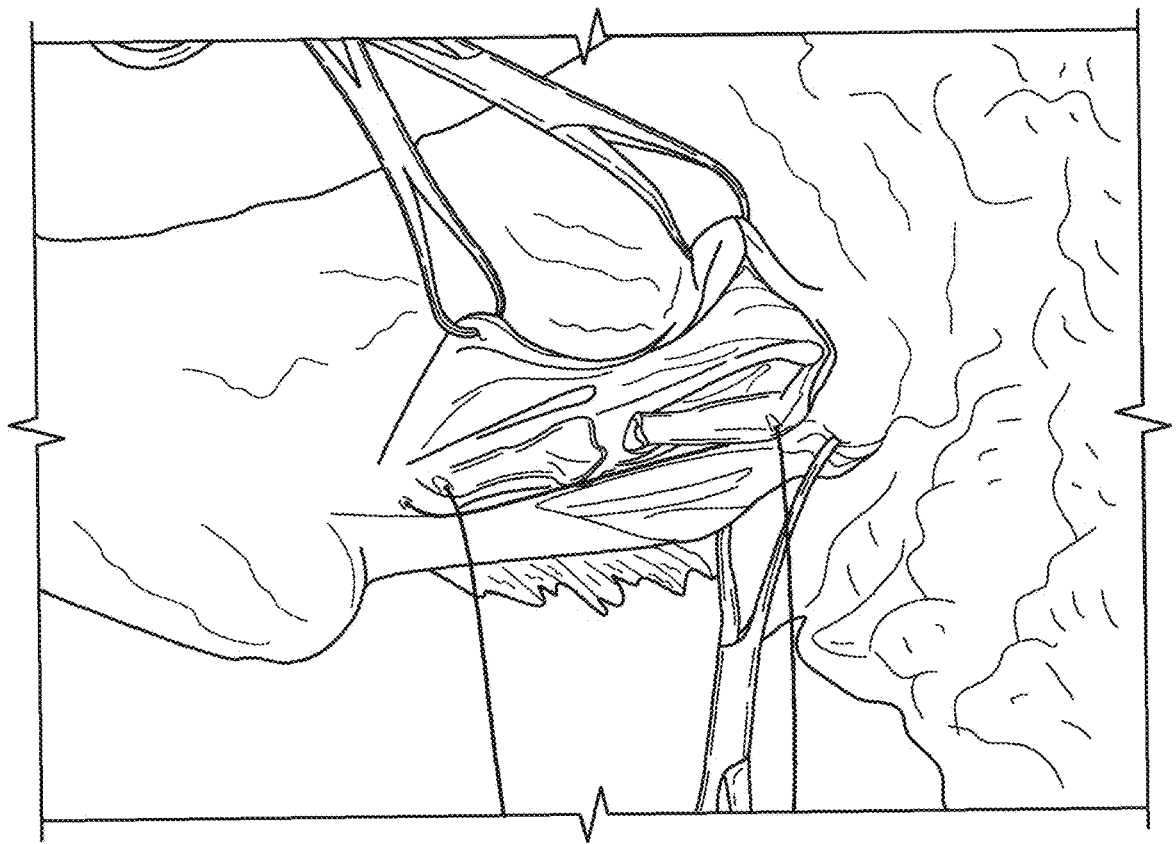
FIG. 4 depicts an exemplary suture-stabilized transected Achilles tendon.
Figure 5:
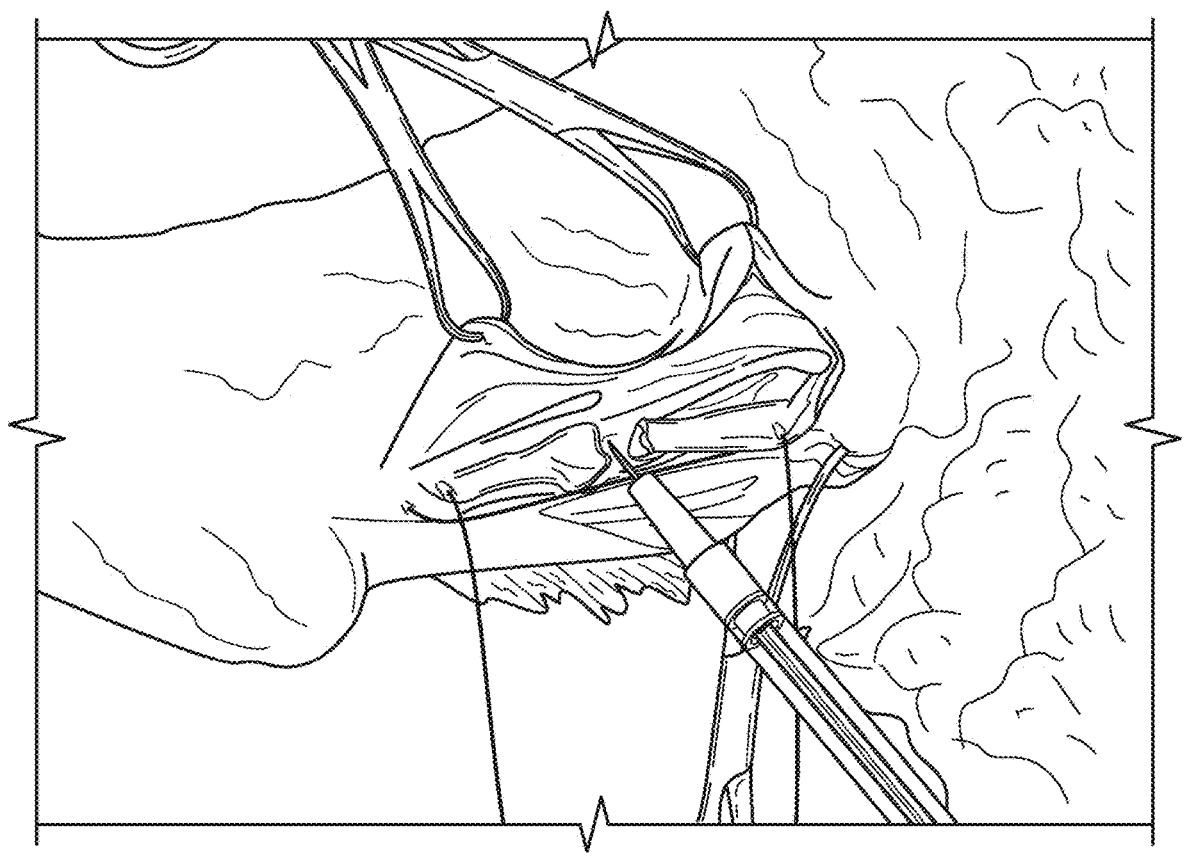
FIG. 5 depicts an exemplary administration of a composition to a stabilized injured Achilles tendon in accordance with an embodiment of the present invention.

After exposure of the tendon, a stabilizing suture (#1 Ethilon) was placed using a modified Mason Allen design with one end at the 2 cm mark and one end at the 6 cm mark. The Mason Allen suture was kept taut to maintain the tendon length, but one end was left untied for the manipulation of the tendon ends. The tendon was then transected at or about the 4 cm mark, after which the tendon ends were re-approximated and the free end of the Mason Allen suture was tied at the distal end of the tendon. A photograph was taken of the transected tendon with a ruler to document the distance from the calcaneal insertion. See, e.g., the exemplary sutured, transected tendon as depicted in FIG. 4. A small tail in the suture was left at the distal end and a small identifying suture (3-0) is placed at the proximal end for identification after necropsy. The overlying soft tissue was closed, leaving a space around the tendon transection for insertion of the flowable matrix. The hydrated flowable collagen matrix material was then placed at the tendon ends in the following manner: The 0.5 cc sterile aliquot was expressed from the syringe through a 20 gauge needle, with the beveled side facing towards the transected tendon ends. Half (0.25 cc) of the sterile aliquot was expressed along the surface of each of the transected tendon ends. Care was taken to ensure that the material was evenly distributed in the gap space. See, e.g., an exemplary flowable composition of the present invention being delivered the exemplary sutured, transected tendon as depicted in FIG. 5.

The overlying subcutaneous tissue and skin were closed according to standard surgical procedure. A splint made of OrthoGlass was formed on the lower foot to prevent knuckling during ambulation. Immediately after surgery, the sheep were transferred from the operating table and observed until the swallowing reflex returns, at which point they were extubated. Upon completion of surgery, the sheep were propped in sternal recumbency, and then housed for the duration of the study. Splinting and/or casting of the sheep were used to reduce knuckling and/or overstretching of the repaired tendon. Postoperative analgesia were provided, and the animals were managed according to standard postoperative care procedures.

Clinical Observations

Animals were observed twice daily until sacrifice. During the first week, the surgical site was observed, and photos obtained, for abnormal healing and wound dehiscence. During the entire post-surgical study period, the animals were observed for general attitude, appetite, operated limb use (e.g., lameness), and appearance of the surgical site. Antibiotics were administered to an animal when infection developed at the surgical site, and noted in the observations. Ultrasound images, for both the operated and the contralateral, unoperated, Achilles tendon were obtained for all treatment sites 2-, 4-, and 8-weeks post-surgical using methods known in the art. Eight (8) weeks following the index surgery, all animals were sacrificed for tissue harvest.

Biomechanical Testing

Mechanical performance of a stimulated Achilles tendon rupture and reattachment using three different treatment groups as discussed above under the Experiment Overview Section was determined.

Materials and Methods

Following harvest, specimens were wrapped in saline soaked gauze and stored at −20° C. until testing. The metatarsus was potted in 2″ PVC pipe using high strength polymethylmethacrylate (PMMA). Specimens were kept moist during the potting preparation and biomechanical testing with a saline spray at 15 minute intervals. The potted metatarsus was mounted in a custom-designed testing fixture that was rigidly attached to the materials testing system loading frame (MTS MiniBionix II, Edan Prairie, Minn.). A custom-designed cryoclamp was implemented to preserve the natural cross section of the Achilles tendon and minimize soft tissue slippage and applied a uniaxial traction force to the construct at an angle of approximately 135° to the potted metatarsus. This was done to mimic the physiological force vector of the tendon. Testing commenced when a thermocouple attached to the cryoclamp registered −22° C., a temperature previously reported to be sufficient to ensure secure coupling between the tendon and clamps. No tissue-embedded suture material was cut prior to testing. Thus, the biomechanical results represent the combined mechanical contribution of the embedded suture and the reparative tissue.

Four retroreflective markers were sutured or glued on to the potted construct: one on the calcaneus immediately adjacent to the repair site, two on the tendon—one proximal and one distal to the Achilles tendon-repair tissue interface. The fourth was glued on the cryoclamp. Three cameras (Motion Analysis, Santa Rosa, Calif.) recorded the spatial movement of the markers at 60 Hz. Marker displacement measurements using the camera system allowed for real-time monitoring of local tissue displacement/strain within the reparative tissue.

Phase 1: 30 Cycle Dynamic Preconditioning

A cyclic loading test was initially employed to pre-condition the repaired tendon. Using a force control protocol, a 10 Newton (N) preload was applied to the construct for two minutes. This was designated the initial configuration for all constructs. The repaired constructs were then cyclically preconditioned in a force-control protocol from 10 to 50 N at 0.25 Hz for 60 cycles to reach a steady-state. Sixty (n=60) cycles was chosen based on previous experiments in our laboratory that have demonstrated that the slope of the displacement versus time curve converges between 50 and 60 cycles. Parameters of interest included conditioning elongation, defined as the difference in peak-to-peak displacement between the first and sixtieth cycles, and peak-to-peak elongation, defined as the average of the difference between the local minimum and maximum of the 58th, 59th, and $60^{th}$ cycles.

Quasi-Static Failure Loading

Following preconditioning, the repaired constructs were loaded to failure under displacement control at a rate of 1 mm/s. Biomechanical parameters of interest included ultimate load-to-failure, quasi-static global construct stiffness (defined as the slope of the load-displacement curve), local repair tissue stiffness, elongation at failure, and energy absorbed at failure. Finally, the failure mechanism was documented for each specimen. Digital images and/or video were taken prior to testing, during the ramp to failure procedure, and following construct failure.

Statistical Analysis

A One-Way ANOVA followed by a Tukey's post hoc multiple comparison test was used to identify significant differences in continuous biomechanical parameters between the IFWM control and the 0.3 mg/mL PDGF and 1.0 mg/mL PDGF treatment groups. Significance was set at p≤0.05 and all analyses were performed with SigmaStat 3.1 (Systat Software, Inc., San Jose, Calif.).

Results

Figure 6A:
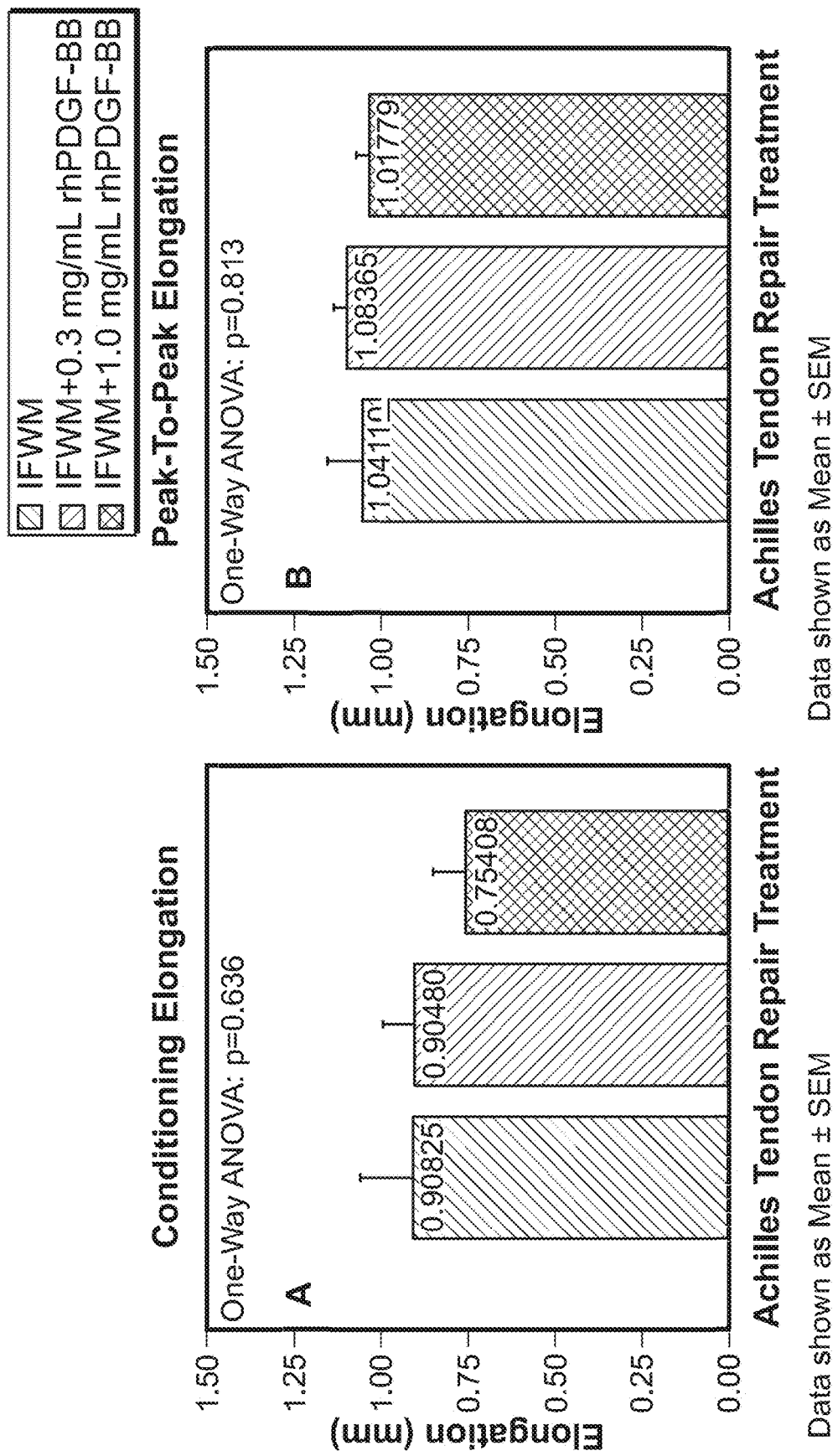
FIGS. 6A-6B show the cyclic preconditioning results (conditioning elongation and peak-to-peak elongation) of the Achilles Tendon Repair Treatment A) including two hematoma affected specimens and B) excluding two hematoma affected specimens.

No gross visual differences were identified between the three treatment groups. Two of the six (33%) constructs in the IFWM+0.3 mg/ml rhPDGF-BB group displayed an evident hematoma on the lateral aspect of the repair tissue. The presence of this hematoma affected the biomechanical properties of the repair, evidenced by failure initiating at the exact location of the hematoma at unusually low loads. Data analysis was performed with (n=6) and without (n=4) these two hematoma affected specimens. Raw data from the cyclic preconditioning component of testing including the two hematoma affected specimens in the 0.3 mg/mlrhPDGF-BB group are presented in Table 4. No significant differences in conditioning elongation (p=0.636) or peak-to-peak elongation (p=0.813) were identified between the IFWM, IFWM+ 0.3 mg/ml rhPDGF-BB, or IFWM+1.0 mg/ml rhPDGF-BB treatment groups (FIG. 6A).

TABLE 4A

Summary Data from Cyclic Preconditioning Analysis. Data Reported as Mean ± S.E.M.

| Treatment | n | Conditioning Elongation (mm) | Peak-to-Peak Elongation (mm) |
|---|---|---|---|
| IFWM | 6 | 0.908 ± 0.153 | 1.041 ± 0.103 |
| IFWM + 0.3 mg/mL rhPDGF-BB | 6 | 0.905 ± 0.110 | 1.084 ± 0.054 |
| IFWM + 1.0 mg/mL rhPDGF-BB | 6 | 0.754 ± 0.119 | 1.018 ± 0.051 |
| iCTL | 6 | 0.188 ± 0.045 | 0.553 ± 0.016 |

Figure 6B:
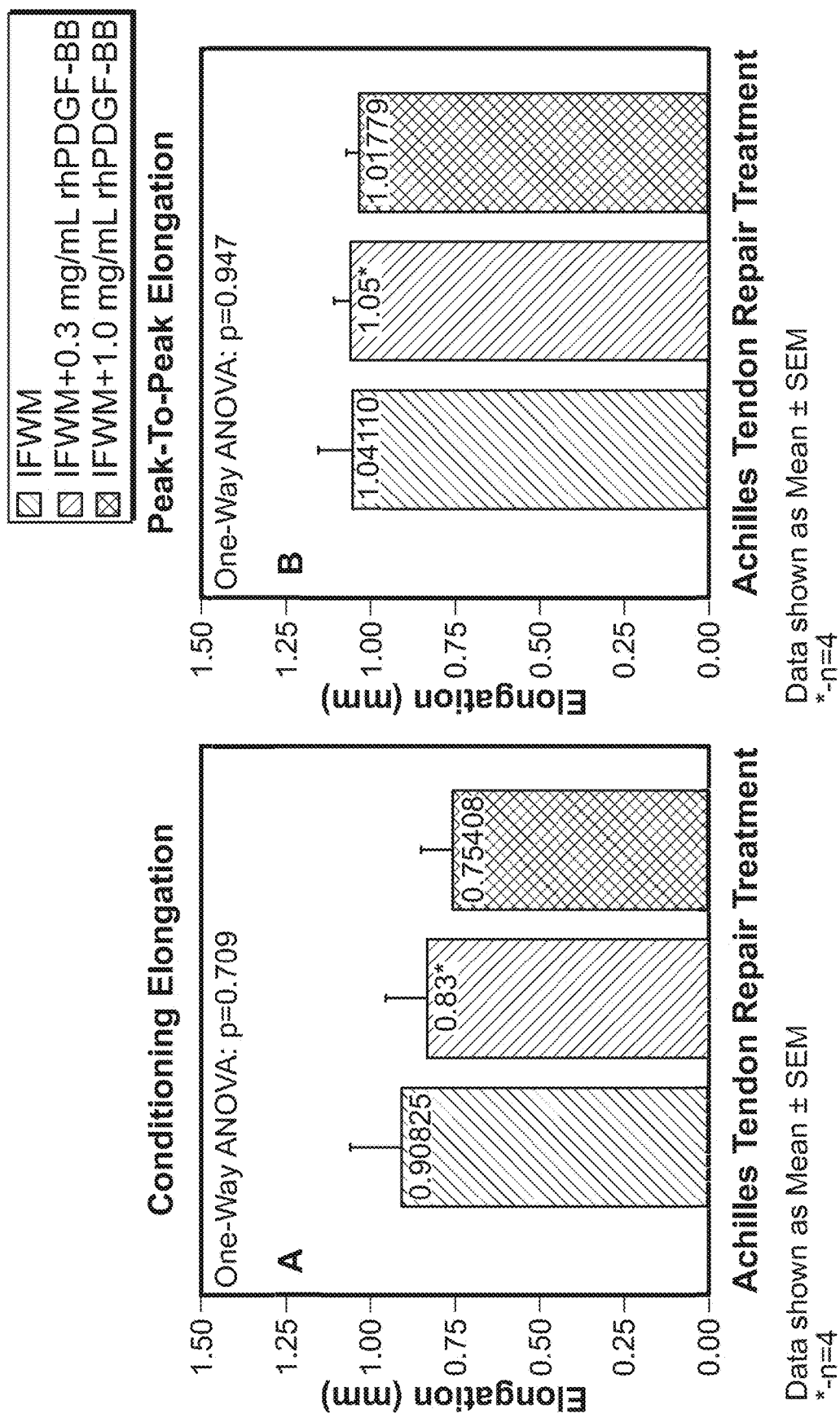

Similarly, no significant differences in conditioning elongation (p=0.709) or peak-to-peak elongation (p=0.947) were identified between the IFWM, IFWM+0.3 mg/ml rhPDGF-BB, or IFWM+1.0 mg/ml rhPDGF-BB treatment groups. FIG. 6B. Raw data from the cyclic preconditioning component of testing with hematoma affected specimens excluded from the analysis are presented in Table 4B.

TABLE 4B

Summary Data from Cyclic Preconditioning Analysis. Data Reported as Mean ± S.E.M.

| Treatment | n | Conditioning Elongation (mm) | Peak-to-Peak Elongation (mm) |
|---|---|---|---|
| IFWM | 6 | 0.908 ± 0.153 | 1.041 ± 0.103 |
| IFWM + 0.3 mg/mL rhPDGF-BB | 4 | 0.829 ± 0.123 | 1.084 ± 0.049 |
| IFWM + 1.0 mg/mL rhPDGF-BB | 6 | 0.754 ± 0.119 | 1.018 ± 0.051 |
| iCTL | 6 | 0.188 ± 0.045 | 0.553 ± 0.016 |

** two of the six specimens in this group displayed an evident hematoma on the lateral aspect of the repair tissue at which tissue rupture clearly initiated during RTF testing. These have been removed from statistical comparison.

Figure 7A:
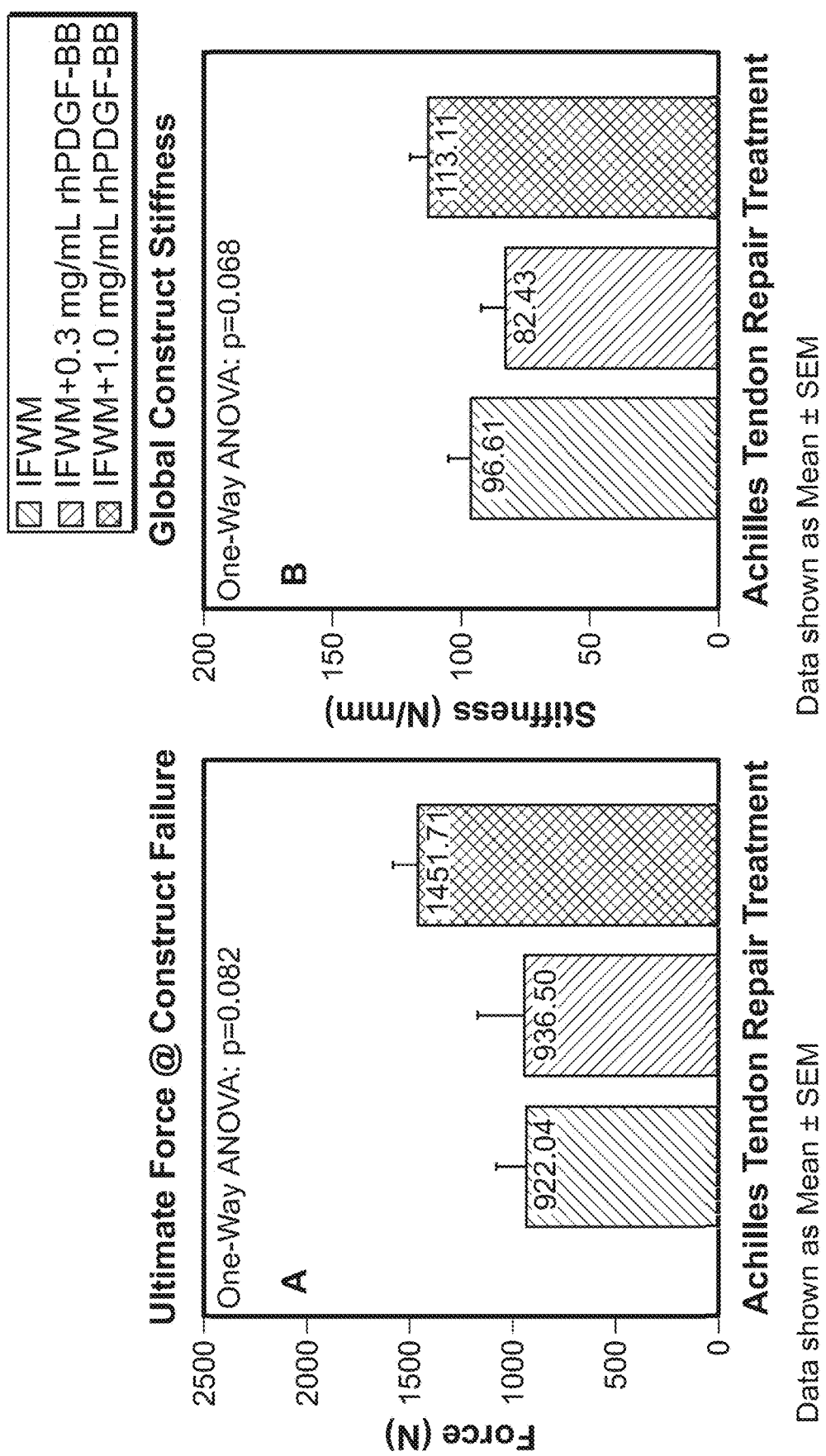
FIG. 7A-7B shows the ramp to failure testing results (ultimate force at construct failure and global construct stiffness) of the Achilles Tendon Repair Treatment.

Raw data from the ramp to failure component of the biomechanical testing with the two hematoma affected specimens included in the analysis are presented in Table 5A. No significant differences in the surgically repaired Achilles tendons were identified for any quasi-static parameter between the IFWM, IFWM+0.3 mg/ml rhPDGF-BB, or IFWM+1.0 mg/ml rhPDGF-BB treatment groups (p>0.05, Table 5, FIG. 7A). Though not significant, the 1.0 mg/mL rhPDGF-BB dose resulted, on average, in a 57.4% and 55.0% increase in ultimate force to failure relative to the IFWM control and 0.3 mg/mL rhPDGF-BB groups, respectively. No significant difference in energy absorbed at failure was identified between the three treatment groups (p=0.209: IFWM, 6423.33±1811.26 N*mm; 0.3 mg/mL rhPDGF-BB, 7346.00±2989.94 N*mm; 1.0 mg/mL PDGF, 12173.33±2049.62 N*mm), though the energy absorbed at failure in the 1.0 mg/mL rhPDGF-BB treatment group was, on average, 89.5% and 65.7% greater than the IFWM control and 0.3 mg/mL rhPDGF-BB treatment groups, respectively.

TABLE 5A

Summary Data from Ramp to Failure Analysis. Data Reported as Mean ± S.E.M.

| Treatment | n | Ultimate Load (N) | Global Construct Stiffness (N/mm) | Global Displacement at Failure (mm) |
|---|---|---|---|---|
| IFWM | 6 | 922.04 ± 149.91 | 96.61 ± 8.56 | 14.55 ± 2.42 |
| IFWM + 0.3 mg/mL rhPDGF-BB | 6 | 936.50 ± 231.74 | 82.43 ± 9.75 | 14.66 ± 2.04 |
| IFWM + 1.0 mg/mL rhPDGF-BB | 6 | 1451.71 ± 125.08 | 113.11 ± 7.14 | 18.02 ± 1.24 |
| iCTL | 6 | 3767.54 ± 224.43 | 176.97 ± 10.75 | 27.04 ± 1.95 |

Figure 7B:
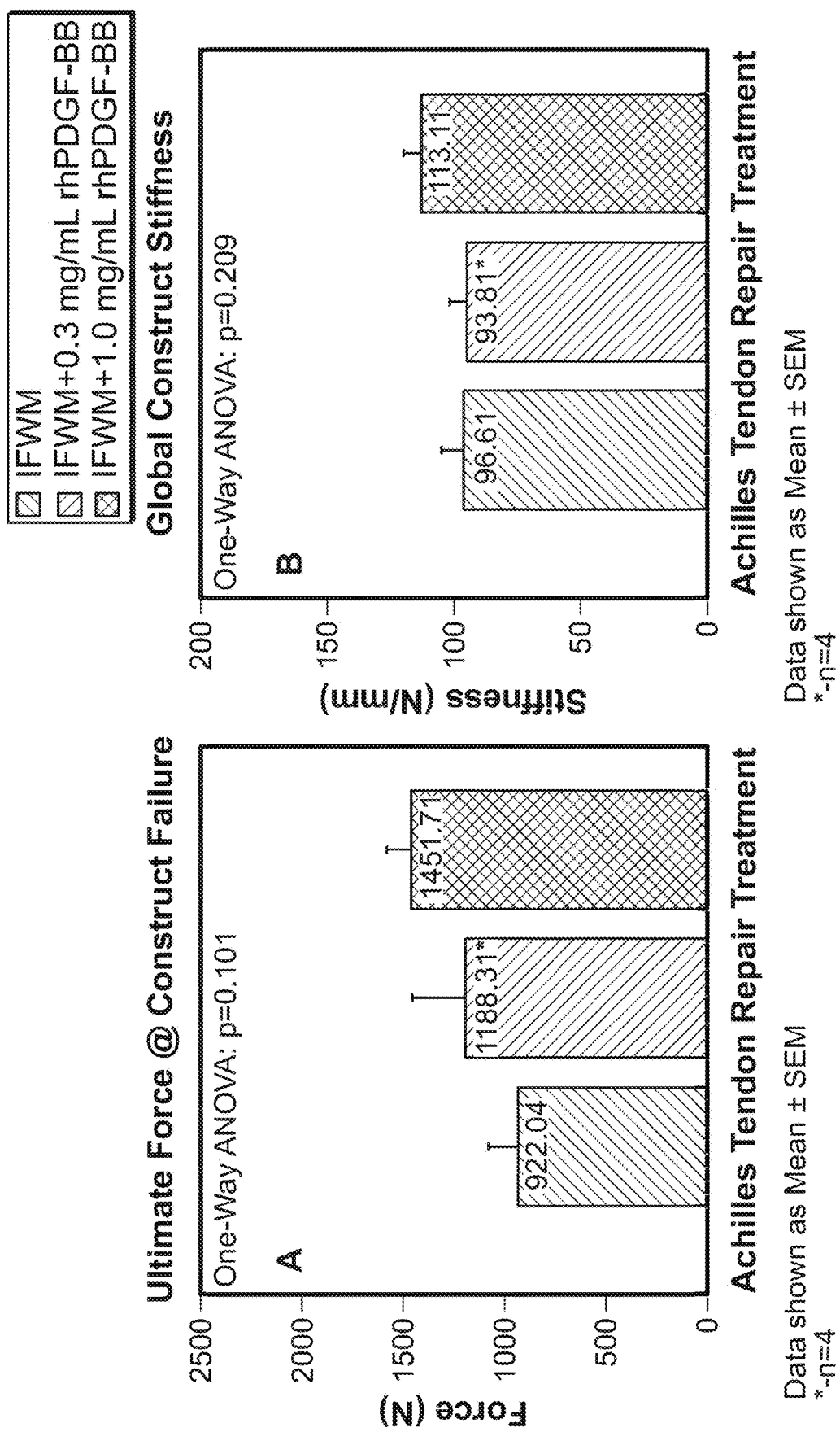

Raw data from the ramp to failure component of the biomechanical testing with the two hematoma affected specimens excluded from the analysis are presented in Table 5B. No significant differences in the surgically repaired Achilles tendons were identified for any global quasi-static parameter between the IFWM, IFWM+0.3 mg/ml rhPDGF-BB, or IFWM+1.0 mg/ml rhPDGF-BB groups (p>0.05, Table 5B, FIG. 7B). Though not significant, the 1.0 mg/ml PDGF dose resulted, on average, in a 57.4% and 22.2% increase in ultimate force to failure relative to the IFWM control and 0.3 mg/ml PDGF groups, respectively. No significant difference in energy absorbed at failure was identified between the three groups (p=0.247: IFWM, 6423.33±1811.26 N*mm; 0.3 mg/ml PDGF, 9850.75±4006.36 N*mm; 1.0 mg/ml PDGF, 12173.33±2049.62 N*mm), though the energy absorbed at failure in the 1.0 mg/ml PDGF treatment group was, on average, 89.5% and 23.6% greater than the IFWM control and 0.3 mg/ml PDGF treatment groups, respectively.

TABLE 5B

Summary Data from Ramp to Failure Analysis. Data Reported as Mean ± S.E.M.

| Treatment | n | Ultimate Load (N) | Global Construct Stiffness (N/mm) | Global Displacement at Failure (mm) |
|---|---|---|---|---|
| IFWM | 6 | 922.04 ± 149.91 | 96.61 ± 8.56 | 14.55 ± 2.42 |
| IFWM + 0.3 mg/mL rhPDGF-BB | 4** | 1188.31 ± 266.12 | 93.81 ± 7.17 | 16.16 ± 2.61 |
| IFWM + 1.0 mg/mL rhPDGF-BB | 6 | 1451.71 ± 125.08 | 113.11 ± 7.14 | 18.02 ± 1.24 |
| iCTL | 6 | 3767.54 ± 224.43 | 176.97 ± 10.75 | 27.04 ± 1.95 |

Figure 8:
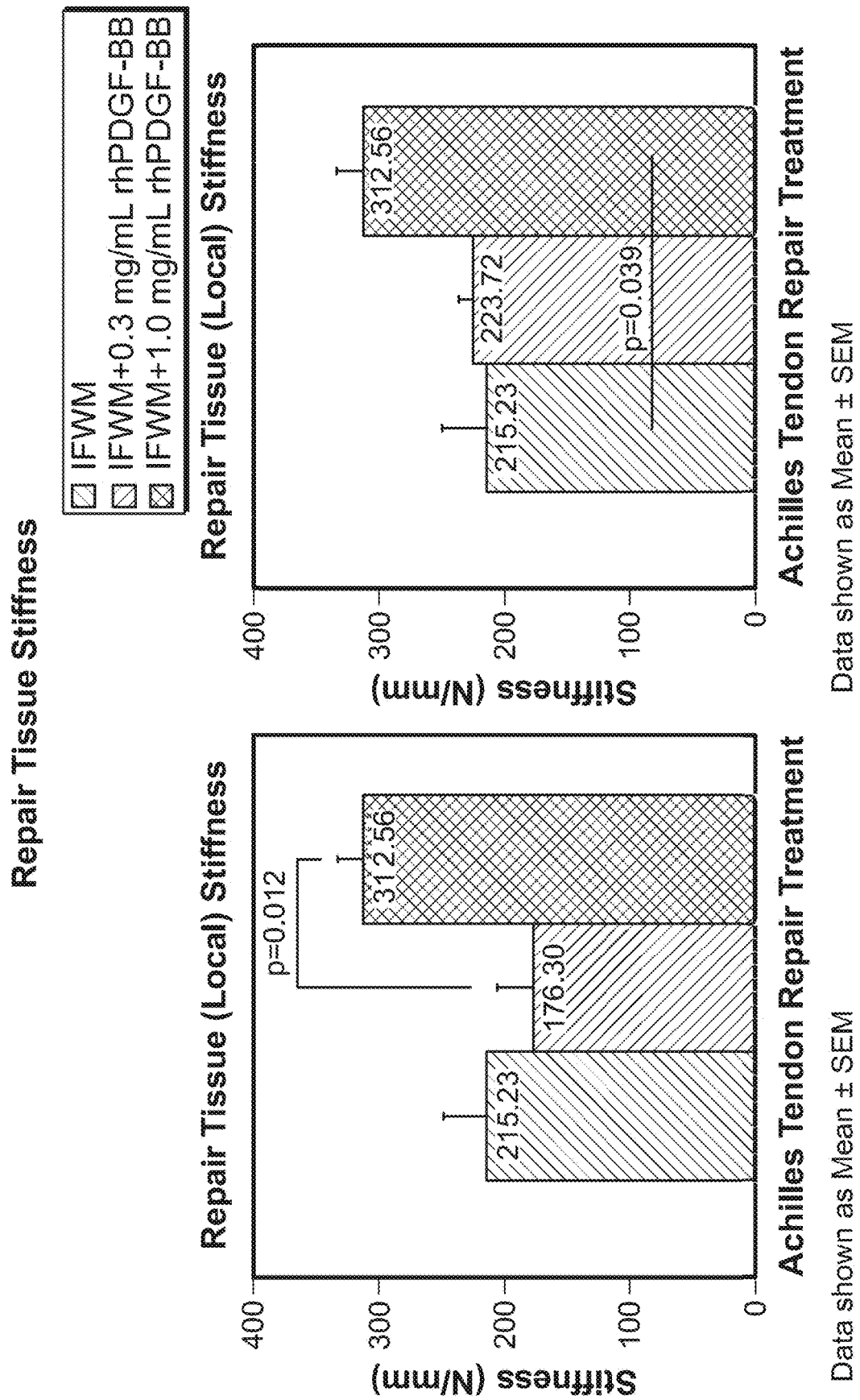
FIG. 8 shows the repair tissue stiffness results of the Achilles Tendon Repair Treatment including or excluding the two hematoma affected specimens (left panel and right panel, respectively).

Including the two hematoma affected specimens in the analysis (Table 6, FIG. 8 (left)), local repair tissue stiffness in the 1.0 mg/mL rhPDGF-BB treatment group (n=6, 312.56±20.86 N/mm) was, on average, 77.3% greater than the local stiffness quantified in the 0.3 mg/mL treatment group (n=6, 176.30±31.17 N/mm). This difference was statistically significant (p=0.012). No significant difference in local repair tissue stiffness was identified between the 1.0 mg/mL PDGF treatment group and the IFWM control (n=6, 215.23±33.23 N/mm, p=0.075). With the two hematoma affected specimens excluded from the analysis (FIG. 8(right)), local repair tissue stiffness in the 1.0 mg/ml rhPDGF-BB treatment group was, on average, 39.7% greater than the local stiffness quantified in the 0.3 mg/ml treatment group (n=4, 223.72±11.46 N/mm). This difference was not statistically significant (p=0.096). However, local repair tissue stiffness in the 1.0 mg/ml group was significantly greater (45.2%, p=0.039) than that of the IFWM control (215.23±33.23 N/mm).

TABLE 6

Summary Data from Ramp to Failure Analysis. Data Reported as Mean ± S.E.M.

| Treatment | n | Local Construct Stiffness (N/mm) | n | Local Construct Stiffness (N/mm) |
|---|---|---|---|---|
| IFWM | 6 | 215.23 ± 33.23 | 6 | 215.23 ± 33.23 |
| IFWM + 0.3 mg/mL rhPDGF-BB | 6 | 176.30 ± 31.17 | 4** | 223.72 ± 11.46 |
| IFWM + 1.0 mg/mL rhPDGF-BB | 6 | 312.56 ± 20.86 | 6 | 312.56 ± 20.86 |
| iCTL | 6 | 882.87 ± 124.03 | 6 | 882.87 ± 124.03 |

Of the eighteen (n=8) treatment constructs tested, n=16 (88.9%) failed at the proximal interface between the preparative tissue and intact Achilles. Of note, two of the sic constructs in the IFWM+0.3 mg/mL rhPDGF-BB treatment group displayed a hematoma on the lateral aspect of the repair tissue that was grossly visible during dissection and subsequent biomechanical testing. In both constructs, failure initiated at these regions. The remaining n=2 (11.1%) treatment constructs failed at the distal interface between the reparative tissue and the intact Achilles. Mode of failure for the n=6 intact contralateral Achilles tendon constructs varied. Two (n=2, 33.3%) intact constructs failed via metatarsal fracture within the PMMA potting material. Three (n=3, 50%) intact constructs failed via mid-substance tearing of the Achilles tendon, and one (n=1, 16.7%) failed via calcaneal avulsion.

Conclusion

After eight weeks in vivo, the biomechanical data observed for the group treated with IFWM+1.0 mg/mL rhPDGF-BB were consistently increased and on average exhibited a greater healing response compared to the IFWM controls and IFWM+0.3 mg/mL rhPDGF-BB treatment groups. This dosing effect was manifested as a 55%/22.2% (n=6/n=4) and 57.4% increase in ultimate load-to-failure relative to the 0.3 mg/mL and IFWM alone treatment groups, respectively. Repair (i.e., local) tissue stiffness was increased on average by 77.3%/39.7% (n=6/n=4) and 45.2% relative to the 0.3 mg/mL rhPDGF-BB and IFWM alone treatment groups, respectively. Additionally, the ultimate force observed in this study for the IFWM+1.0 mg/mL rhPDGF-BB group was increased compared to other studies which utilized a matrix (34.9-fold higher than a 24 week repair using a collagen patch combined with a platelet rich plasma fibrin matrix (Sarrafian et al., *Trans ORS*, 33:322 (2008)) or a protein (1.9-fold higher than 3 week repair treated with CDMP-2 (Virchenko, *Arch Orthop Trauma Surg*, 128:1001-1006 (2008)).

Histological Testing
Tissue Harvest and Trimming

Following euthanasia, operated Achilles tendons were harvested, splinted to prevent curling of the tissue, and placed in 10% neutral buffered formalin for histological processing. In addition to the operated Achilles, two unoperated contralateral Achilles tendons were harvested for histological analysis. After fixation for 24 hours, each Achilles tendon was bisected into medial and lateral halves using a scalpel. The proximal end of the Achilles was notched to preserve orientation throughout the histological processing. One animal in the 1.0 mg/ml rhPDGF-BB group was euthanized after 40 days (5.8 weeks) of healing due to reasons unrelated to the study (pneumonia).

Histological Processing

All specimens (n=8) were further fixed, dehydrated, cleared, infiltrated, and embedded using standard paraffin histology techniques and equipment (Shandon Citadel 2000 Processor and Shandon Histocentre 2, Thermo Shandon, Inc, Pittsburgh, Pa.). The paraffin blocks were faced and approximately 10 micron sections cut on Shandon Finesse rotary microtome (Thermo Shandon, Inc, Pittsburgh, Pa.). Five sections were cut per specimen, for a total of 40 sections. Each histological section was stained with Hematoxylin-Eosin (H&E). High-resolution digital images were acquired field by field for the entire stained slide including regions of interest using an Image Pro Imaging system (Media Cybernetics, Silver Spring, Md.) and a Nikon E800 microscope (AG Heinze, Lake Forest, Calif.).

Qualitative Histopathology

All tissue sections were evaluated to assess the quality of the reparative/healing tissue, the native tendon/reparative tissue interface, vascularization, inflammation, and collagen density/fiber orientation. Sections were assessed blinded to treatment. Tendon retraction was also measured via calibrated gross digital images using Image Pro Plus imaging system.

Results
Tendon Retraction

All operated specimens displayed some degree of tendon retraction after 8 weeks of healing. On average, the Achilles tendon retracted 55.7±16.1 mm for the No Dose group, 39.8±4.5 mm for the 0.3 mg/ml rhPDGF-BB dose group, and 44.4±1.5 mm for the 1.0 mg/ml rhPDGF-BB dose group.

Histopathology

After 8 weeks of healing, the flowable collagen was visible in all of the specimens regardless of the rhPDGF-BB dose. The flowable collagen was generally located more towards the distal end of the repair site. In a few cases the flowable collagen had migrated out of the center of the repair site towards the dorsal surface of the reparative tissue. In one specimen the flowable collagen was observed dispersed over the entire length of the repair site. Only mild inflammation was observed in and around the flowable collagen. Inflammation was judged to be slightly increased in the flowable collagen+rhPDGF-BB groups (0.3 mg/ml and 1.0 mg/ml doses) compared to No Dose specimens. Inflammation generally consisted of multinucleated foreign body giant cells and/or mononuclear inflammation (lymphocytes, monocytes and plasma cells). Neutrophils were generally not observed. Fibroplasia with new collagen production by activated fibroblasts was observed within the flowable collagen regardless of the rhPDGF-BB dose. Although some fibroplasias was observed within the flowable collagen, there was a discontinuity within the reparative collagen fibers. The proximal and distal ends of the native Achilles tendon were generally well integrated with the new collagen fibers of the reparative tissue. In a few cases, the distal interface demonstrated slightly better integration as compared to the proximal interface. The proximal interface contained many young fibroblasts producing immature collagen with a distorted native Achilles tendon end combined with mild inflammation.

There was relatively high fibroplasia and collagen production by activated fibroblasts with a high density of collagen fibers regardless of treatment or rhPDGF-BB dose. Primary collagen fiber alignment was coincident with the native Achilles collagen fiber direction, as observed using polarized light. Fibroblast density was similar between treatments. In one specimen, the density of fibroblasts was relatively lower and the collagen fibers were more immature, less dense, and less oriented. The collagen fibers were generally aligned parallel to the native Achilles fiber direction although no differences were observed between groups for collagen or fibroblast density.

Inflammation was observed within the repair sites for all treatments and was generally mild. Inflammation consisted of multinucleated foreign body giant cells with mononuclear inflammation (lymphocytes, monocytes and plasma cells). Neutrophils were generally not observed. Inflammation was associated with the presence of suture material and flowable collagen, and most probably due to localized damage of the host tissue. Abundant vascularization was also observed within the repair sites for all treatments. Increased inflammation was associated with more abundant vascularization. Vascular hypertrophy, reactive vessels with plump endothelial cells and thickening of vessel walls, was observed for all rhPDGF-BB doses. There were more hypertrophic vessels noted in the specimens treated with the 0.3 mg/ml and 1.0 mg/ml doses as compared to the No Dose specimens. These vessels were usually located within the reparative tissue in superficial regions of the dorsal surface. In one specimen (40 days post operation), there was abundant vascularization, but these vessels were smaller and hypertrophic vessels were not observed. Hemorrhage, found in conjunction with a hematomatomatous space and fibrin, was observed in 2 specimens.

Conclusion

In summary, based on the limited number of samples tested, there were no qualitative differences in Achilles tendon repair between the 0.3 mg/ml dose, 1.0 mg/ml dose, and control (No Dose) groups. The presence of rhPDGF-BB did not prevent healing nor did it illicit anegative response histologically. There was similar healing between the 0.3 mg/ml dose and 1.0 mg/ml dose treatment groups. All operated specimens displayed some degree of tendon retraction. The flowable collagen was visible in all specimens regardless of rhPDGF-BB treatment or dose, and was generally located towards the distal end of the repair site. Inflammation was generally mild and considered of multinucleated foreign body giant cells with mononuclear inflammation (lymphocytes, monocytes and plasma cells). Inflammation was judged to be slightly increased within the flowable collagen treated with rhPDGF-BB (0.3 mg/ml and 1.0 mg/ml dose) as compared to the No Dose group. In the reparative tissue there was substantial, ongoing fibroplasias with a high density of collagen fibers that was irregardless of rhPDGF-BB treatment or dose. Reparative collagen fiber alignment was generally paralleled to the native Achilles collagen fiber direction. Collagen and fibroblast density was similar between treatments. Abundant vascularity was observed in all specimens. There were judged to be more hypertrophic vessels noted in the specimens with the 0.3 mg/ml and 1.0 mg/ml doses as compared to the No Dose group. In a few cases, the distal interface displayed slightly better integration as compared to the proximal interface, where there was less mature collagen and a distorted native Achilles tendon end combined with mild inflammation. This may be the result of continuous tendon retraction and concomitant local tissue damage caused by the suture slippage.

Example 7: Normal and Diseased Primary Human Tenocytes Proliferate in Response to rhPDGF-BB This study determined whether rhPDGF-BB directly activated proliferation and/or chemotaxis of primary tenocytes derived from patients with tendinopathies. Such findings can support the notion of therapeutic potential of rhPDGF-BB in tendinopathies.

Patients and Methods
Patients

Ten patients with tendinopathies were involved in this study, including five patients with Achilles tendinopathy and five patients with tendinopathy of the posterior tibial tendon (PTT). Additional five patients were involved who underwent full joint replacement of the knee.

Primary Cultures of Tenocytes

Tendon tissue which would otherwise be discarded was obtained from normal and injured tendons during reconstructive surgery procedures performed for clinical indications. These tissues included the tendinopathic portion of the Achilles or PTT tendons, as well as the healthy (non-tendinopathic) portion flexor digitorum longus (FDL) tendon tissue, Achilles tendon tissue, and Patellar tendon tissue. Primary tenocyte explant cultures were obtained from these tissues and tested at passages 3 to 5. Tenocyte identity was confirmed by assessing the expression of a tenocyte-specific gene scleraxis and genes for collagens a1(I), a2(I), and a1(III) in real-time PCR assays with specific primers.

Cell Proliferation

Tenocyte monolayers were trypsinized, resuspended in DMEM/F12 medium containing 0.5% dialyzed fetal bovine serum, allowed to attach overnight, and then incubated with titrated concentrations rhPDGF-BB for 24 h. Changes in cell proliferation rates were assessed based on BrdU incorporation during DNA synthesis in cells using a commercially available assay (Roche Applied Science, Indianapolis, Ind.). Each culture was tested in triplicates for each dose of rhPDGF-BB.

Cell Migration

Tenocyte monolayers were trypsinized, resuspended in DMEM/F12 medium containing 0.5% dialyzed fetal bovine serum and placed in the upper chamber of the 96-well ChemoTx® disposable cell migration system (Neuro Probe, Gaithersburg, Md.). The lower chambers contained titrated concentrations of rhPDGF-BB. Tenocytes were allowed to migrate across the membrane separating the chambers for 48 h. 96-well plates were then spun down and freeze thawed three times to lyse the migrated cells. The amount of viable migrated cells was measured based on cytoplasmic lactate dehydrogenase (LDH) using a commercially available kit from Promega (Madison, Wis.).

Statistical Analysis

One-way ANOVA was used to determine whether stimulation with rhPDGF-BB affects tenocyte proliferation in a dose-dependent fashion.

Results

Only tenocyte cultures but not control pulmonary fibroblast cultures or control primary T lymphocyte cultures expressed scleraxis mRNA, whereas tenocytes and fibroblasts but not lymphocytes expressed the collagen gene mRNAs.

In all cases, tenocytes from tendon tissues involved or not involved in the disease process responded to rhPDGF-BB stimulation by accelerating BrdU incorporation ($p<0.05$, one-way ANOVA). The responses were dose-dependent and were observed at 10, 50 and 150 ng/mL of rhPDGF-BB. Even though all cell cultures responded to rhPDGF-BB stimulation, there was significant variability among patients in the magnitude of BrdU incorporation after rhPDGF-BB stimulation. Incorporation of BrdU increased from a minimum of 2.1±0.2 fold to a maximum of 10.7±0.5 fold compared to control non-stimulated cultures. Tenocytes from five patients responded paradoxically, with a greater increase in BrdU incorporation at a lower (10 ng/mL) than higher (50 and 150 ng/mL) concentrations of rhPDGF-BB. Such paradoxic response was observed in tenocytes derived from both tendinopathic and normal tissues of these patients. Tenocytes derived from healthy tendons of four patients incorporated twice more BrdU in response to rhPDGF-BB stimulation than did tenocytes derived from the diseased tissues. In one patient, tenocytes from the diseased tissue incorporated four fold more BrdU in response to rhPDGF stimulation than did tenocytes from the uninvolved tissue.

In all cases, tenocytes were chemotactically responsive to rhPDGF-BB at 50 ng/mL and 150 ng/mL. Tenocytes were not exposed to 10 ng/mL rhPDGF-BB for chemotaxis experiments because of low response in pilot experiments. Again, responses were dose-dependent, with greater chemotaxis to 150 ng/mL than to 50 ng/mL of rhPDGF-BB. However, tenocytes from 5 patients responded with greater chemotaxis to 50 ng/mL than to 150 ng/mL of rhPDGF-BB, with significant decline in the number of migrated cell ($p<0.05$, two-sided Student's t-test). There was variability among patients in the maximal chemotactic response to rhPDGF-BB, from 1.4±0.1 to 4.0±0.5 fold increase compared to non-stimulated control. There was no statistically significant difference ($p>0.05$) in tenocyte chemotaxis to rhPDGF-BB within matching tenocyte cultures derived from tendinopathic or from healthy tendon tissues.

Conclusion

The results of these experiments suggest that tenocytes derived from healthy and tendinopathic tissues respond to rhPDGF-BB by increasing proliferation and chemotaxis rates. Importantly, tenocytes from some patients showed paradoxical response to PDGF, in which higher doses caused less effect than lower doses. Equally important, tenocytes from diseased tendons were in some cases differentially responsive to PDGF versus tenocytes from healthy tendons, implying that proper dosing may be of paramount importance in the clinical setting.

Example 8: Evaluation of Four Collagen Matrices in Combination with Recombinant Human Platelet-Derived Growth Factor-BB (rhPDGF-BB) for Application in Treatment of Tendon to Bone Reattachment This study assessed the physical characteristics, biocompatibility (in vitro and in vivo) and stability (biodegradation) of four collagen matrices that could be used in conjunction with rhPDGF-BB at the tendon-bone interface for application in the treatment of tendon to bone attachment, such as anterior cruciate ligament reconstruction.

Methods (i) Materials and Preparations

Four Type I collagen matrices (pads) were evaluated in this study. Three fibrous collagen matrices (A, B and C) were bovine dermal derivatives of differing collagen densities (A=4.5% collagen; B=5% collagen, C=6% collagen; BIO-BLANKET™ collagen made from different percentage of collagen slurry provided by Kensey Nash Corporation) and the fourth fibrous matrix (D) was a bovine tendon derivative characterized as "highly porous" (90% porosity) (COL-LATAPE®, Integra LifeSciences). All collagen sheets (1.5-2.0 mm thick) were punched to 8 mm diameter discs for physical characterization and in vitro (cytocompatibility) evaluation. In vivo (biocompatibility and biodegradation) evaluations were performed utilizing 1×1 $cm^2$ pads. rhPDGF-BB: recombinant human platelet derived growth factor (rhPDGF-BB) at 0.3 mg/ml was also prepared.

Cell source is primary ovine tenocytes (<4 passages) isolated from ovine flexor tendon that were cultured in growth medium (DMEM/F-12 containing 10% fetal bovine serum (PBS)) and down regulated with basic medium (DMEM/F-12 containing 2% PBS) 12 hours prior to use.

(ii) In Vitro Cytocompatibility Study

50 µl (50,000 cells) of the tenocyte cell suspension in basic medium was added to each collagen disc. After 1 h incubation at 37° C. and 5% $CO_2$ atmosphere without medium emersion, the cell-seeded discs were transferred to a 24-well plate prefilled with 2 ml of basic medium alone or in combination with rhPDGF-BB (30 ng/ml). After 12 h static culture, the plates with cell-seeded discs were placed on an orbital shaker (60 rpm) in the incubator. Medium changes were provided every 48 h. On days 2, 4, and 6, triplicate samples from each material and treatment were utilized for ATP assay, to determine the live cell number in/on the collagen matrices. On day 4, one sample from each material and treatment was used for scanning electron microscopic (SEM) evaluation. On day 6, quadruplicate samples from each material and treatment were utilized for histological assessment.

(iii) In Vivo Biocompatibility and Biodegradation Study

A total of 12 New Zealand white rabbits were used for this study. Through an anterior-medial incision, the femur was exposed. After removing the periosteum, the midpoint of the ventral surface of the femur was located and two areas (1 cm×1 cm), approximately 0.5-0.8 cm proximal and distal to the midpoint, were decorticated using a round bur and copious irrigation to prevent overheating of the bone. Two holes (0.9 mm) were drilled at the midpoint of the decorticated site on the medial and lateral edges. Finally, a 5-0 silk suture was passed through the two holes and the collagen pad (pre-saturated with 100 µl of 0.3 mg/ml rhPDGF-BB) was then tied to secure the pad to the surface of the femur. Surgery was conducted bilaterally, so each femur received two pads and each animal received one each of the four different collagen pads. The order of pads on the femur was randomized. At 1, 2, and 3 weeks post surgery, 4 animals were euthanized and the femurs, together with the pads and surrounding tissue, were fixed in 10% neutral buffered formalin (NBF), embedded in methyl methacrylate (MMA), and stained with a Goldner's trichrome procedure.

Results (i) In Vitro Cytocompatibility Study

The ATP assay revealed that cell growth on/in the collagen discs significantly increased in the presence of rhPDGF-BB, and increased with time in culture, with no significant differences observed across the different matrices under the same treatment conditions. The SEM images for the matrices alone revealed qualitative differences in porosity with matrix D demonstrating the greatest porosity and matrices A, B and C showing decreasing levels of porosity. SEM results for each of the matrices following cell seeding showed that there were more cells observed on the surface of the three fibrous matrices of differing densities, with the fewest observed on the surface of the "highly porous" matrix (D). Histological images from cross sections of each of the matrices seeded with cells further supported the SEM observations, demonstrating cell distribution along the outside surface of the pads for matrices with increasing density, with matrix D demonstrating the greatest distribution of cells throughout the matrix.

(ii) In Vivo Biocompatibility and Biodegradation Study

Figure 9A:
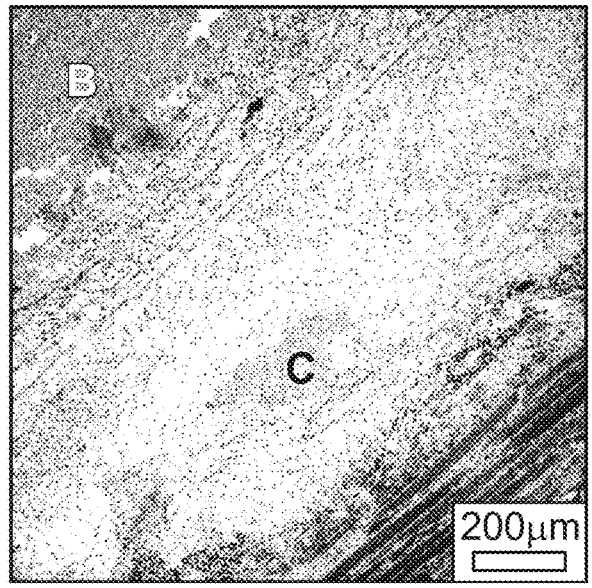
FIGS. 9A-9D depict histological sections of implanted Collagen A (panel a), B (panel b), C (panel c), and D (panel d) at 3 weeks post-implantation. Key: B=bone; C=collagen; arrow indicates undegraded collagen. Scale bar=200 μm
Figure 9B:
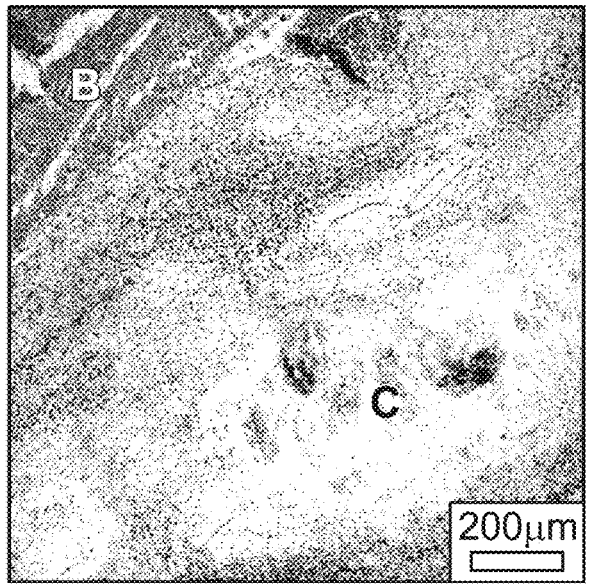
Figure 9C:
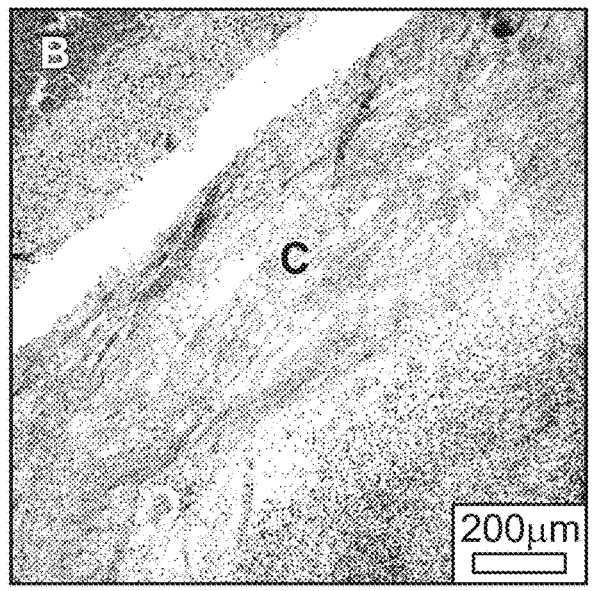
Figure 9D:
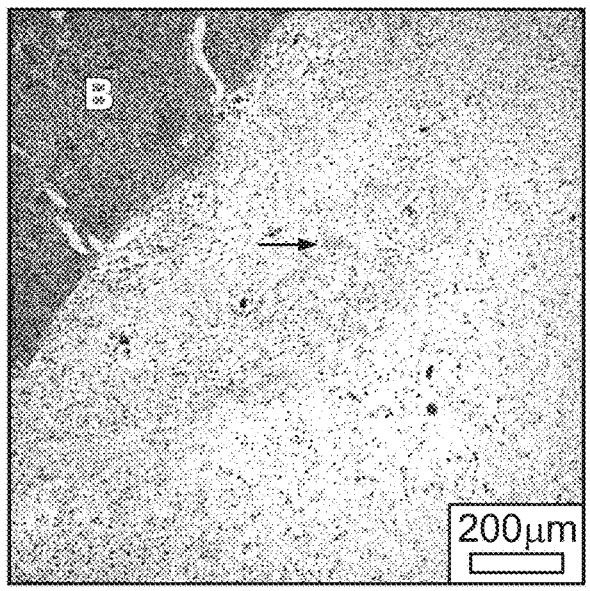

Histological assessment revealed that all four collagen pads remained intact 1 week post-implantation. In the tissue around the four different matrices, there was increased cell infiltration of granulocytes and mononuclear cells. Two (2) weeks post implantation, partial degradation was observed for matrices A, B, and D with obvious cell infiltration associated with matrix D. Three (3) weeks post implantation, matrix D was mostly degraded with only small collagen fragments observed among normal fibroblastic cells (FIG. 9D). Sites receiving collagen matrix derivatives of dermal origin (A, B, and C) exhibited degradation which was inversely proportional to the collagen density. Extensive inflammatory cell infiltration was observed for these matrices which became more localized over the three week observation period (FIGS. 9A-9C).

The results showed that collagen matrix D was the most porous, with a homogenous fine collagen fiber network, providing more accessible surface area for cell attachment and migration. In vivo evaluation of the individual matrices showed that collagen D exhibited the shortest residence period and appeared to be the most biocompatible material, demonstrating minimal inflammatory cell infiltration 3 weeks post-implantation, while the collagen matrices of differing densities demonstrated increasing inflammatory cell infiltration which localized into foci by 3 weeks post-implantation.

Example 9: Use of rhPDGF-BB and a Collagen Wrap to Augment Tunnel Fixation of Tendon in a Caprine Model of Tendon-Bone or Ligament-Bone Reattachment This study assesses the histological and biomechanical benefits of wrapping a collagen sponge soaked in a dose of rhPDGF-BB prior to insertion and fixation of the long flexor tendon in a transmetaphyseal tibial tunnel. The method of affixing grafts for anterior curciate ligament reconstruction is as described by Rodeo et al., *J. Bone Joint Surg. Am.*, 75(12):1795-1803 (1993). A collagen pad in combination with rhPDGF-BB is used to promote more rapid, complete integration of the tendon or ligament within a tibial insertion site.

(A) Materials and Methods (i) Species

The goat is a suitable model because, like humans, its bones undergo remodeling, which is a balanced combination of bone formation and resorption leading to normal bone structure. The bones of smaller animal models, such as rats or mice, do not undergo remodeling and thus do not represent the biological processes that would occur as the tendon reintegrates with bone. Furthermore, the tendons of larger animals, such as goat, can be more easily manipulated and reattached using techniques and instrumentation used in human surgery.

A total of 24 skeletally mature goats (female, mixed genetic background) are used in this study. These animals are divided among 3 treatment groups (Table 7). Group 1 undergoes sharp detachment of the long flexor tendon from its femoral insertion on the lateral side, followed by threading through a bone tunnel drilled obliquely through the tibial metaphysis. Once on the other side, the tendon is attached to the medial cortex of the tibia with stainless steel sutures (see FIGS. 10 and 11). The contralateral limb of Group 1 animals comprises those in Group 2. Group 2 undergoes the same surgical procedure, but prior to threading through the tunnel, the tendon is wrapped with a 25×15 mm collagen sponge (COLLATAPE®, Integra LifeScience Corporation, Plainsboro, N.J.). Once affixed to the medial cortex of the tibia, the collagen matrix is hydrated with 1.0 mL of sodium acetate buffer (20 mM, pH 6.0). Within each animal, the limbs receiving these treatments are randomized (Table 8). A total of 10 animals are used for Groups 1 and 2, resulting in an n=5 for each time point (2 and 4 weeks). Each time in life (the cohort of animals used for each time point and each treatment) produces 3 specimens for biomechanical testing and 2 specimens for histology.

Group 3 animals undergoes the same surgical procedure as those in Group 2 but the collagen sponge is hydrated with 1.0 mL of 1.0 mg/mL recombinant human platelet-derived growth factor BB (PDGF-BB). In this group, both limbs receive treatment with PDGF-BB. Group 3 consists of 10 animals; this results in an n=10 samples (two operated limbs/animal) for each time point (2 and 4 weeks). Each time in life produces 5 specimens for biomechanical testing and 5 specimens for histology.

Two more animals are used for a pilot surgical study to confirm feasibility of surgically implanting the material (one receives treatment as described for groups 1 and 2 above and the other receives treatment as described for group 3 above). These animals are observed for 2 weeks post-surgery to confirm a return to normal ambulation and an absence of complications. Following this period, animals from the pilot study are euthanized and the tissues collected. If the surgeries and post-operative evaluative period occur without incident, the remainder of the study (20 animals) is performed as planned.

(ii) Test and Control Articles

Test Article 1 is 1.0 mg/ml rhPDGF-BB in 20 mM sodium acetate buffer, pH 6.0+/−0.5, liquid form and stored at 2° C.-8° C. Test Article 2 is collagen from COLLATAPE®, Integra LifeSciences, solid form and stored at room temperature.

iii) Dose Preparation

Mixing of Collagen with rhDGF-BB

The test and control articles are mixed. Aseptic preparation is used for articles. All mixing is performed at room temperature. The formulated test and control articles are used for up to 1 hour after preparation.

The collagen pads are cut to 25×15 mm, wrapped over the tendon, and threaded through the bone tunnel. With a 27 G needle, 1.0 mL of 1.0 mg/mL rhPDGF-BB is injected into the tunnel adjacent to the final implant site of the collagen matrix. The medial and lateral openings of the tunnel receive approximately 0.5 mL total of 1.0 mg/mL rhPDGF-BB. The injections made at either the medial or lateral sides of the tunnel are made by injecting at multiple points of the tunnel perimeter, roughly the ¼, ½, ¾, and full circumference of the tunnel opening.

(iv) Test System (Animal and Animal Care)

Skeletally mature female domestic goat (mixed breed, n=24), 30-40 lbs, Q-fever tested with health certificate, are used. No animals have been used for prior experimentation. Animals are placed in runs with a minimum of 10 square feet of space per goat. Cages are constructed of stainless steel and cleaned routinely. Ambient temperature is maintained between 60-80° F. and humidity is maintained between 30-70%.

Goats are provided water ad libitum in a bucket as well as via an automatic watering system (LIX-IT). Hay is provided continuously and once per day goats are provided commercially purchased goat chow. The study animals are acclimatized to their designated housing for at least 14 days prior to the first day of dosing. This acclimation period allows the animals to become accustomed to the study room setting. All animals are given a physical examination, including heart rate, respiration, and fecal floatation. Only those animals judged to be in excellent health by the veterinarian are admitted to the facility and accepted for the study. Animals are treated prophylactically with Ivomec (1 cc/75 lbs) and Penicillin G and Benzocaine (1 cc/10 lbs).

(B) Experimental Design (i) General Description and Surgical Method

Anesthesia is induced within 30 minutes of premedication using goat cocktail [10 cc ketamine (100 mg/ml)+1 ee xylazine (20 mg/ml)] at 1 ml/10 kg IM. Following induction, a cephalic IV catheter is put in place. Ophthalmic ointment is gently placed on the cornea to minimize drying of the eye. Goats are intubated using an endotracheal tube (5-8 ETT) as well as a rumentube. Anesthesia is maintained by use of 1.5-2% isoflurane delivered in 100% oxygen using a rebreathing circuit. If needed, the goat is placed on a ventilator according to the tidal volume (15 mL/kg of BW). Each goat receives warmed Lactated Ringer's solution at 10 ml/kg/hr throughout anesthesia.

Penicillin G and benzocaine (1 cc/10 lbs BW) is administered one hour prior to surgery and EOD (end of day) after surgery for a total of 3 doses. Buprenorphine (Buprenex) is administered at 0.005 mg/kg BW IM BID×48 hrs post-op.

Figure 10:
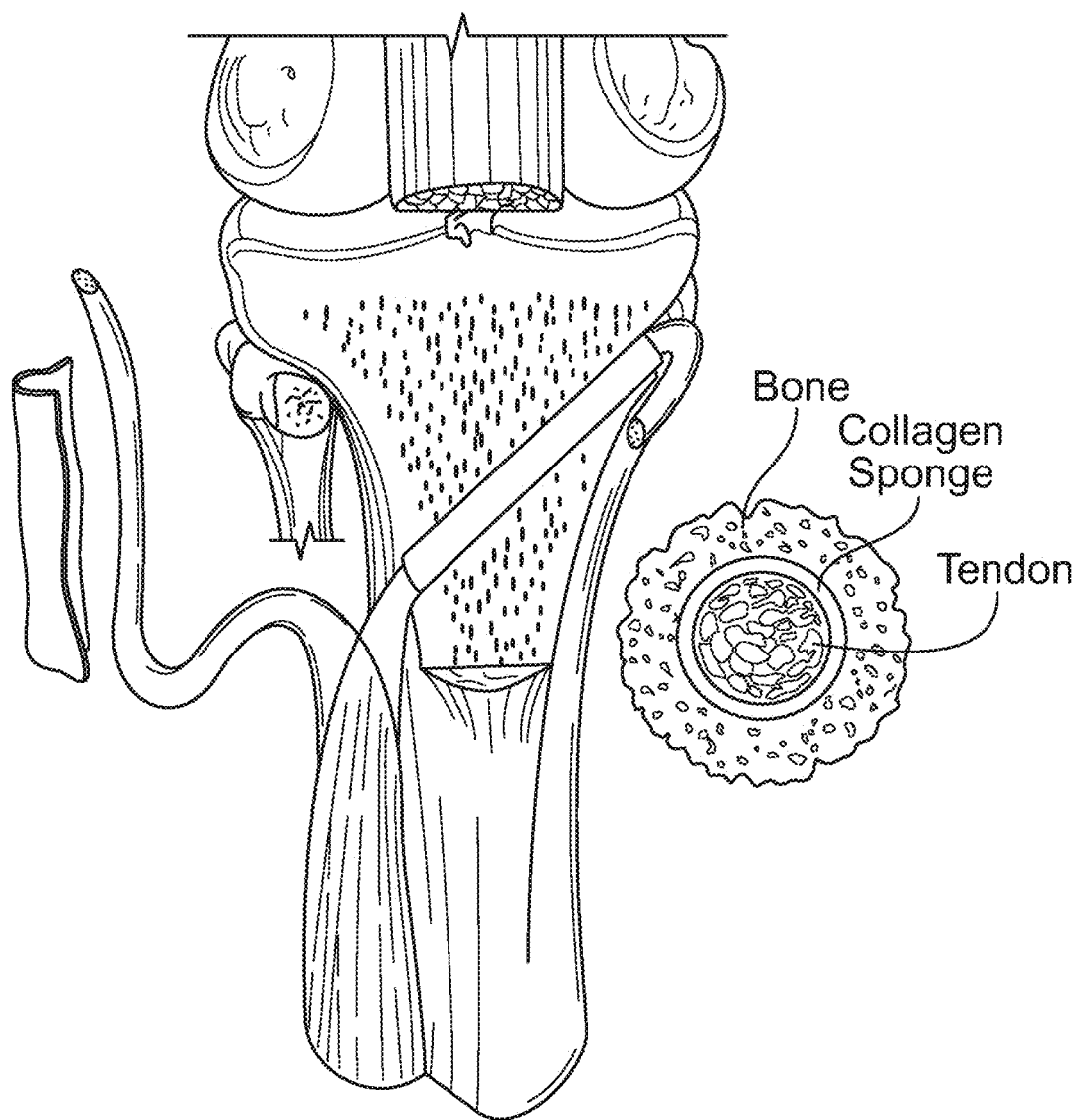
FIG. 10 depicts detachment of the long digital extensor tendon, wrapping of the long digital extensor tendon with a collagen sponge, threading through the tibial bone tunnel, and attachment to the medial cortex. Picture is taken from Rodeo S. A. et al., *Am. J. Sports Med.* 27:476-488 (1999).

The surgical sites is prepared for aseptic surgery (3-chlorhexidine [4%] scrubs alternating with sterile saline solution) and draped. Aseptically, each knee joint is exposed by a lateral parapatellar incision, and the long digital extensor tendon sharply detached from its insertion on the lateral femoral condyle (FIG. 10). The proximal tibial metaphysis is exposed by incision of the fascia of the anterior tibialis muscle and retraction of the muscle laterally.

Figure 11C:
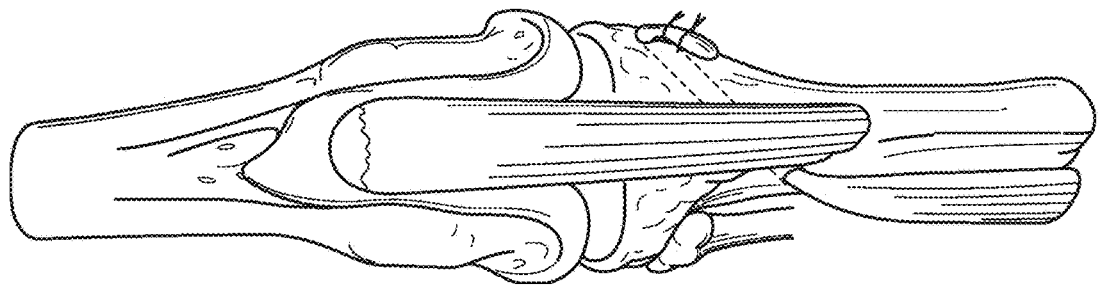
FIGS. 11A-11C depict side view of the surgical procedure including the formation of a tunnel through the tibial metaphysis. Picture is taken from Rodeo S. A. et al., *J. Bone Joint Surg. Am.*, 75(12): 1795-1803 (1993).
Figure 11B:
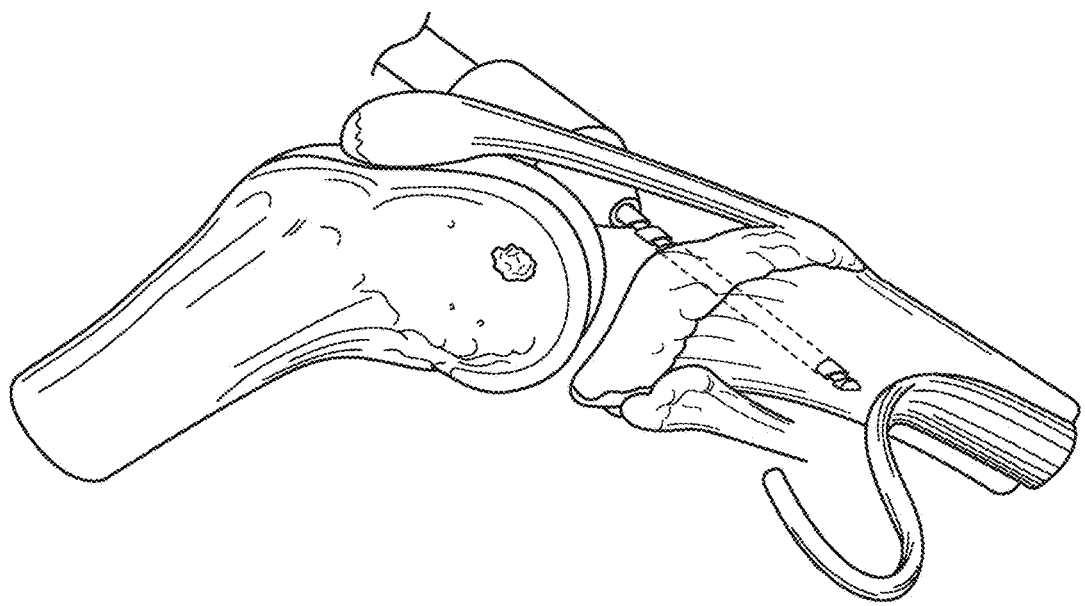
Figure 11A:
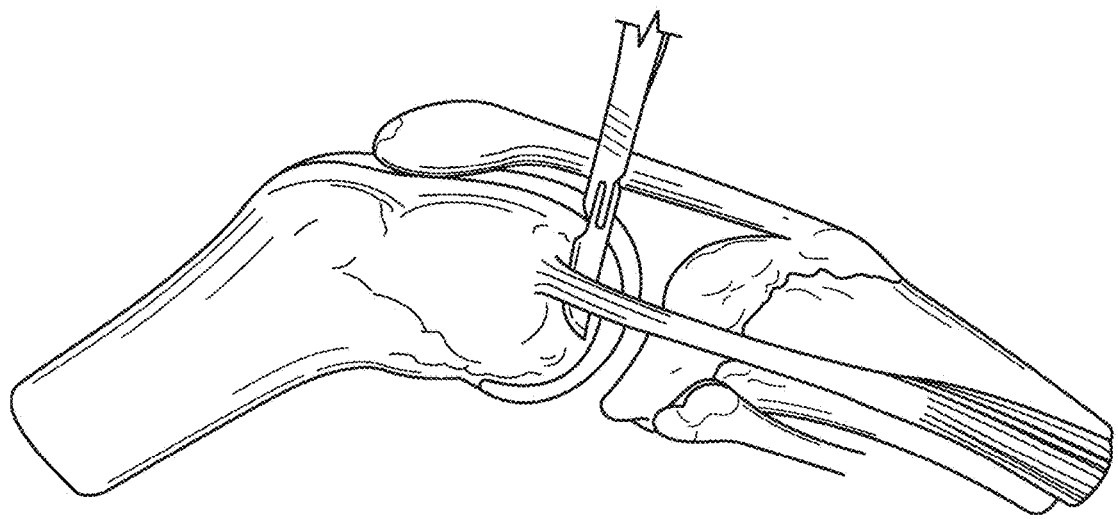

A 5.6 mm diameter drill hole is made in the proximal tibial metaphysis at an angle between 30 and 45 degrees to the long axis of the tibia (FIG. 11). All drilling is performed with copious irrigation and begins proximally at the medial tibial condyle (1 cm below the palpated joint line) and end distally on the lateral side of the tibia (2 cm below the palpated joint line). The depth of the drilled hole is measured with a thin metal depth gauge and recorded. A 25×15 mm collagen sponge is wrapped around the tendon without overlap, secured with 4-0 Vicryl suture, and then threaded through the bone tunnel with stainless steel wire. Once on the other side of the bone, the tendon is fixed to the medial cortex by use of two small holes and interrupted sutures of 4-0 stainless steel. After securing the collagen-wrapped tendon to the bone, 1 mL of sodium acetate buffer pH 6.0 in divided doses is injected into both sides of the tunnel using a 27 G syringe needle to hydrate the collagen sponge. The tendons of control animals, receiving no collagen wrap, is simply threaded through the bone tunnel and fixed on the medial cortex. The growth factor-treated tendons are wrapped with collagen sponge as above, threaded through the bone tunnel, fixed on the medial cortex and then hydrated with 1 mL sodium acetate (pH 6) buffer containing 1 mg/mL PDGF-BB.

Soft tissues are closed in layers with resorbable sutures (e.g. 4-0 Vicryl). After closure of the incision and skin, a radiograph of each limb is performed to document tunnel location and angle. Ideally, the radiograph is oriented so as to image the entire length of the tibial tunnel When goats are sternal and ambulatory, they are returned to their pens. Each goat is allowed to eat and drink ad libidum.

The addition of a dose of rhPDGF-BB to the portion of the long flexor tendon inserted into the metaphyseal bone tunnel is expected to exhibit, over time, a 25% increase in biomechanical load to failure, and improved integration and mineralization by histology and micro-CT.

The surgical procedure is first performed on 2 animals in the presence of the veterinarian to review all aspects of surgery and animal care. After 14 days, if all animals recover without incident, the experimental protocol is then implemented. In the event that difficulties arise, the investigators work diligently with the veterinary staff to resolve any issues necessary to provide optimal care to the animals and ensure the success of the study. During surgery, the animals will be anesthetized and animals are sedated for blood sampling procedures.

(ii) Group Assignments and Dose Levels

TABLE 7

Treatment Groups

| Group | Animals (u) | Operated Side | Matrix | Growth Factor | Sacrifice | Eudpoiuts |
|---|---|---|---|---|---|---|
| 1&2 | 10 | Randomized, Bilateral | Naked tendon or 25 mm × 15 mm collagen sponge | None | 2 weeks 4 weeks | Histomorphometry (n = 2) Biomechanics (n = 3) |
| 3 | 10 | Bilateral | 25 mm × 15 mm collagen sponge | 1.0 mg/mL PDGF-BB | 2 weeks 4 weeks | Histomorphometry (n = 5) Biomechanics (n = 5) |

TABLE 8

Assignment to Treatments

| Animal # | Group | Left Limb | Right Limb |
|---|---|---|---|
| 1 | 1 & 2 | N | SP |
| 2 | 1 & 2 | SP | N |
| 3 | 3 | PDGF | PDGF |
| 4 | 3 | PDGF | PDGF |
| 5 | 1 & 2 | N | SP |
| 6 | 1 & 2 | SP | N |
| 7 | 3 | PDGF | PDGF |
| 8 | 3 | PDGF | PDGF |
| 9 | 1 & 2 | N | SP |
| 10 | 3 | PDGF | PDGF |
| 11 | 1 & 2 | SP | N |
| 12 | 1 & 2 | N | SP |
| 13 | 1 & 2 | N | SP |
| 14 | 3 | PDGF | PDGF |
| 15 | 1 & 2 | N | SP |
| 16 | 3 | PDGF | PDGF |
| 17 | 3 | PDGF | PDGF |
| 18 | 3 | PDGF | PDGF |
| 19 | 1 & 2 | SP | N |
| 20 | 3 | PDGF | PDGF |

N: Naked tendon
SP: Tendon wrapped in collagen sponge (COLLATAPE ®)
PDGF: Tendon wrapped in collagen sponge containing rhPDGF-BB (C) In-Life Observations and Measurements Animals are observed at least daily throughout the study. Recording of observations commences once the pre-selection criteria are complete and continue until the end of study. Each animal is observed for changes in general appearance and behavior, including changes in ambulation. Body weights is measured prior to surgery and at sacrifice. Body weights are taken at additional timepoints as necessary to monitor the animals' health.

At the end of post-operative week 1, animals sacrificed at 2 weeks are injected with 10 mg/kg calcein (vendor TBD) IP (intraperitoneal). Similarly, at 3 weeks, animals sacrificed at 4 weeks are injected with 10 mg/kg calcein (vendor TBD) IP. These injections provide delineation of new bone formation and growth into the tunnel of histological specimens.

(D) Clinical Pathology Evaluation
(i) Serum Collection for Analysis

Approximately 5 mls of blood are collected into non-additive (i.e., "clot") tubes from all animals once pre-surgically, and prior to sacrifice. The blood is centrifuged to obtain serum and divided into two aliquots. The serum is stored at −70° C. or colder for further anaylsis.

(E) Anatomic Pathology

All animals are sacrificed at the appropriate study end points. A gross necropsy is conducted on each animal found dead or sacrificed in a moribund condition to determine the cause of death.

(i) Necropsy

Figure 12:
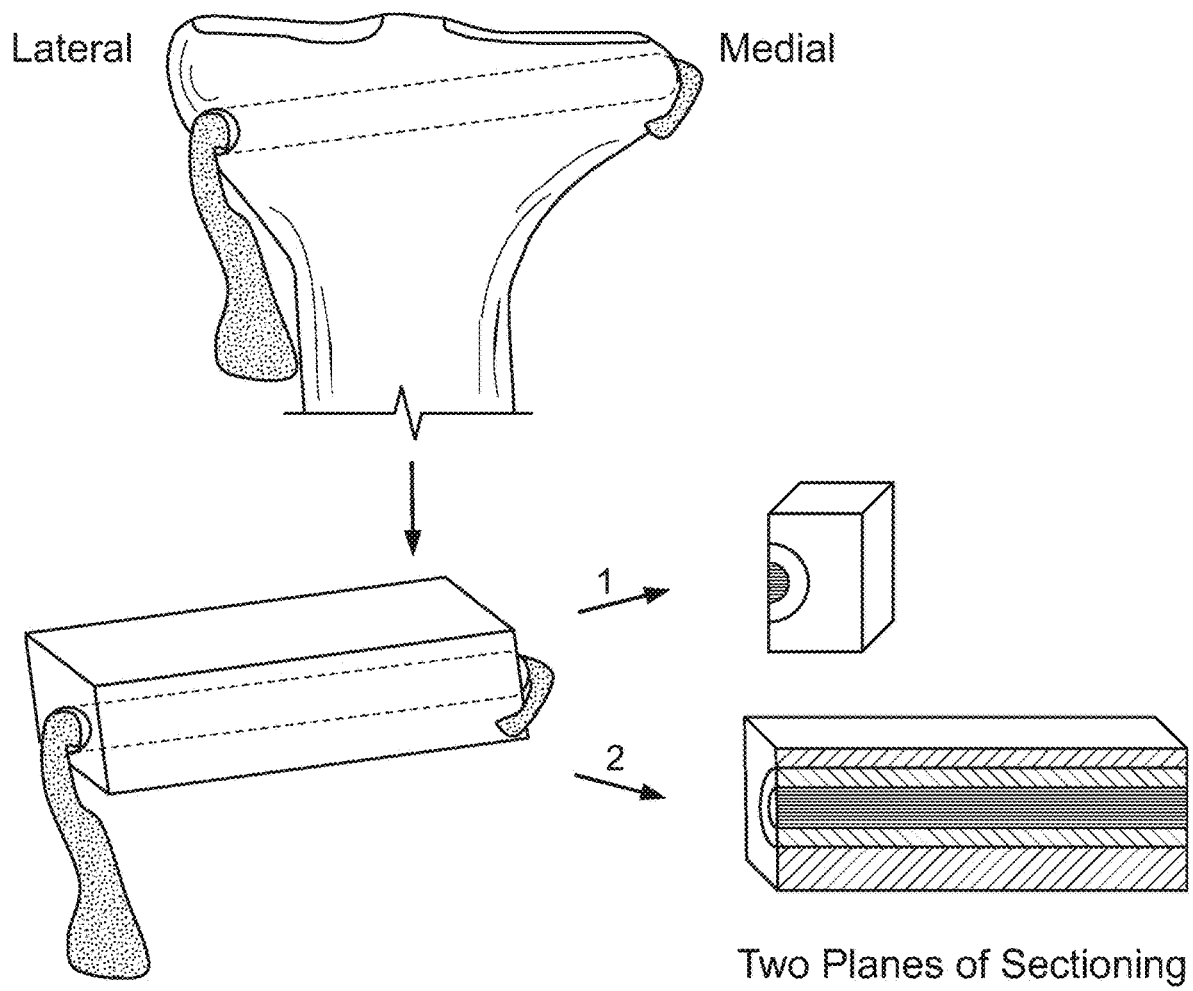
FIG. 12 depicts orientation of histological specimens. Each block will be divided equally longitudinally through the bone tunnel and used to cut cross sections and full length, longitudinal sections.

Goats are euthanized in accordance with the USDA Animal Welfare Act and The Guide for Care and Use of Laboratory Animals (ILAR publication, 1996, National Academy Press. Goats are first sedated using goat cocktail [10 cc ketamine (100 mg/ml)+1 ee xylazine (20 mg/ml)] at 1 ml/10 kg IM. Then, Euthasol (360 mg/ml sodium pentobarbital) at 1 cc/10 lbs BW IV is given. Death is confirmed by auscultation and lack of reflexes (blinking, withdrawal, etc).
(ii) Tissue Collection and Preservation
Gross Observations and Photography of Implant Sites At the time of euthanasia, the implant site is grossly examined and a description of the site recorded. Digital photography is used to document the observations.
(iii) Pathology The stifle joint is disarticulated and a Stryker saw used to cut across the tibia at the mid-shaft. The surrounding muscles and skin is trimmed as much as possible without exposing any more of the bone wound than necessary to perform the clinical evaluation. Each specimen is labeled with a goat number as well as an indication of whether it is the right or left limb. Tissues are placed into neutral buffered formalin (10 vol fixative: 1 vol tissue) and shipped to the sponsor.
(F) Endpoints
(i) Histology and Histopathology Histological processing is conducted. In brief, the tissues are embedded in methyl methacrylate (MMA), sectioned, and stained using hematoxylin/eosin, Safranin 0/Fast Green, Von Kossa/MacNeal's and/or Van Gieson's for light microscopic evaluation. The plane of section for evaluation is as cross-section and longitudinal to the tibial tunnel. A grading system is devised to assess the amount of material remaining at each implant site, extent of mineralization of the tendon and amount of new bone growth along the tunnel walls. Calcein visualization is performed on unstained sections adjacent to sections stained with hematoxylin/eosin
(ii) Biomechanics Specimens retained for biomechanical testing is frozen to −20° C. until use. Tibia/tendon complexes are secured to a multiaxial table in order to align the long axis of the tunnel with the direction of the pulled tendon. This orientation minimizes any effect of friction and allows for directly testing tendon integration/mineralization with the surrounding bone. Peak load to failure measurements is normalized to the length of the tunnel measured by hand and post-operative radiographs.
(a) Study Design The study determines the mechanical performance of a simulated digital extensor tendon reattachment in a tibial bone tunnel. 12 Boer goats are utilized for this study.
(b) Biomechanical Testing Specimens are wrapped in saline soaked gauze and stored at −20° C. until testing. The distal portion of the tibia is potted in 2" PVC pipe using high polymethylmethacrylate. Specimens are kept moist during the potting preparation and biomechanical testing with a saline spray at 15 minute intervals. The potted tibae are mounted in a custom-designed testing fixture that is rigidly attached to the materials testing system loading frame (MTS MiniBionix, Edan Prairie, Minn.; FIG. 12). A custom-designed cryo-clamp designed to grab the natural cross section of the tendon is used in this study to apply uniaxial traction forces to the construct. Any remaining lateral sutures are transected.

Analysis of the biomechanical and histological readings is carried out through analysis of covariance techniques. The effects of rhPDGF-BB and COLLATAPE® are investigated using animal body mass and tendon diameter as covariates.

Readings may be transformed prior to analysis through appropriate methods.
Phase I: 30 Cycle Dynamic Preconditioning A cyclic loading test is initially employed to precondition the tendon repair. A 10 Newton (N) preload is applied and the construct force is allowed to relax by approximately 40%. This is designated the initial configuration for all constructs. The repaired construct is then cyclically preconditioned in a force-control protocol from 10 to 30 N at 0.25 Hz for 30 cycles to reach a steady-state. Thirty (n=30) cycles is chosen because previous experiments in our laboratory demonstrate that the slope of the displacement versus time curve appears to become stable between 20 and 30 cycles.
Phase 2: Quasi-Static Failure Loading Following preconditioning, the repaired constructs are loaded to failure under displacement control at a rate of 1 mm/s. Biomechanical parameters of interest include ultimate load-to-failure and quasi-static stiffness (defined as the slope of the load-displacement curve). Finally, the failure mechanism is documented for each specimen. Digital images are taken of each specimen as loaded into the testing device and following failure to document mode and condition of the failure.
(iii) Microtomography (CT)

Figure 13:
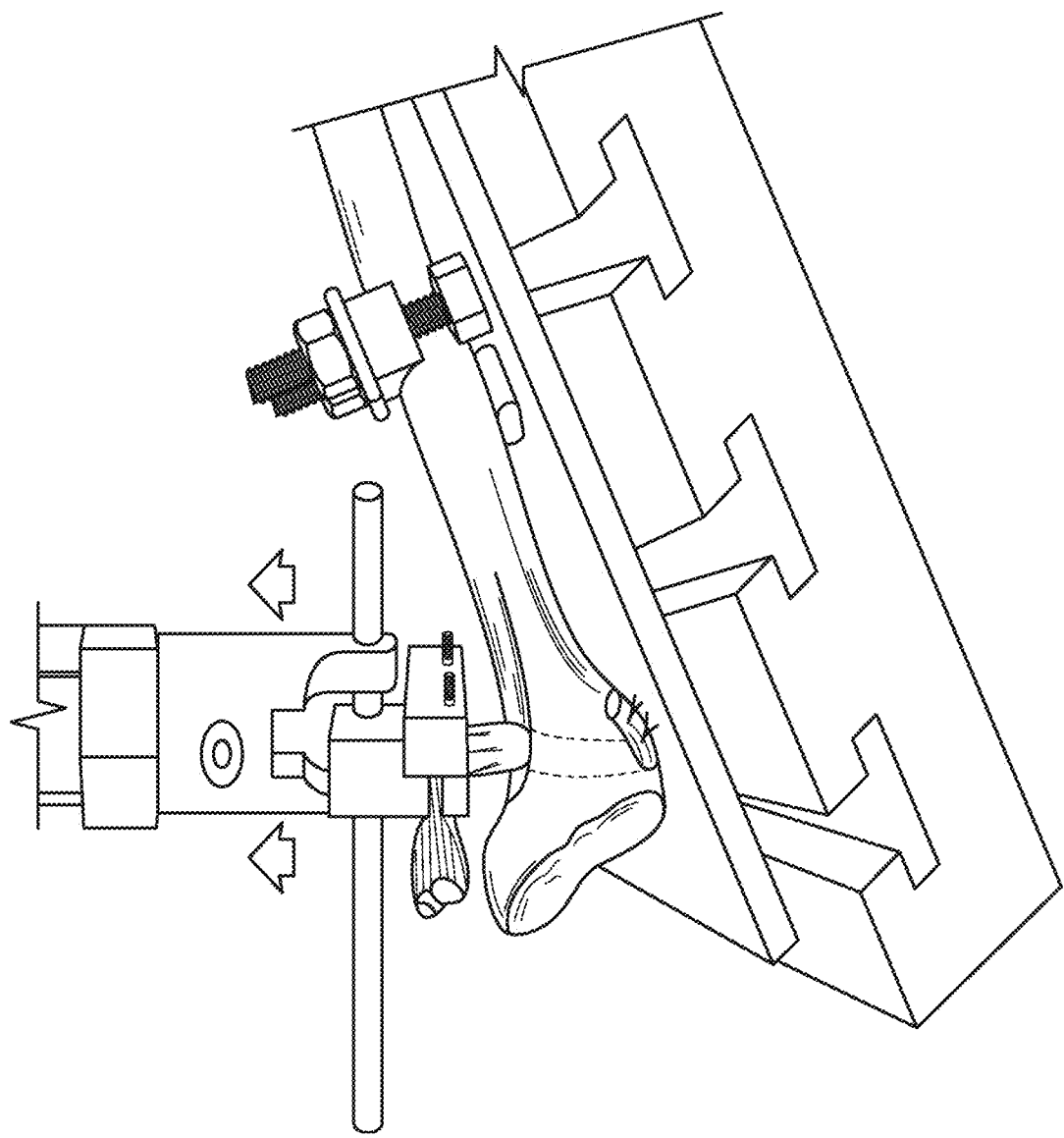
FIG. 13 depicts microtomography (micro CT) of a specimen. Picture is taken from Rodeo S. A. et al., *J. Bone Joint Surg. Am.*, 75(12): 1795-1803 (1993).

Each specimen is scanned at an optimal resolution determined by specimen size. See FIG. 13. Slices are acquired at approximate cross section to cylindrical defect. A semi-automated contouring method is used to select a volume of interest (VOi) limited to the perimeter of the original borders of the defect. An optimized density threshold and noise filter are selected and applied uniformly to all specimens to segment bone from soft tissue. The total mean density, mean density of bone, and bone volume/total volume within tunnel are calculated.

Example 10: Evaluation of the Release Characteristics of rhPDGF-BB (Recombinant Human Platelet-Derived Growth Factor-BB) from BIOBLANKET™ and COLLATAPE® Matrices by BenchTop Model The objective of this study is to measure rhPDGF-BB release from BIOBLANKET™ matrices having different densities and COLLATAPE® matrix using a BenchTop model at room temperature.
Test Materials

TABLE 9

| BIOBLANKET ™ and COLLATAPE ® Matrices | |
|---|---|
| Sample | Lot # |
| BIOBLANKET ™ Collagen (5%) | R436-1 |
| BIOBLANKET ™ Collagen (6%) | R436-2 |
| BIOBLANKET ™ Collagen (7%) | R436-3 |
| COLLATAPE ® Collagen | 1080464 |

Study Design

The study design is listed in Table 10, showing initial flushing time of 5 minutes for all the sample groups (BIOBLANKET™ matrices, COLLATAPE® matrix, and control group without the collagen matrix.

TABLE 10

| Study Design | | |
|---|---|---|
| Sample | Test Materials | Initial Flushing Time |
| 1-3 | BIOBLANKET ™ Collagen (5%) | 5 min |
| 4-6 | BIOBLANKET ™ Collagen (6%) | 5 min |
| 7-9 | BIOBLANKET ™ Collagen (7%) | 5 min |

TABLE 10-continued

Study Design

| Sample | Test Materials | Initial Flushing Time |
|---|---|---|
| 10-12 | COLLATAPE ® | 5 min |
| 13-15 | Control (rhPDGF-BB only) | 5 min |

Figure 14:
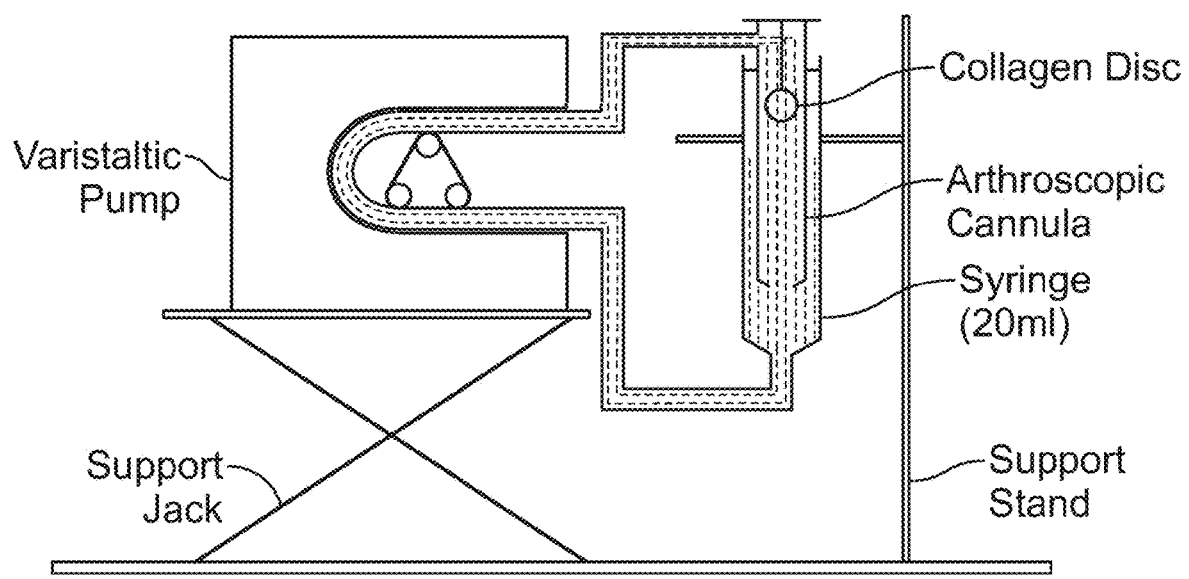
FIG. 14 depicts a Bench Top Arthroscopic model.
Figure 15A:
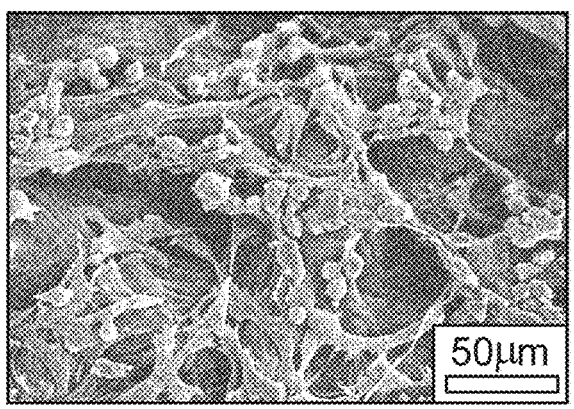
FIGS. 15A-15D show SEM images of ovine tenocytes seeded BIOBLANKET™ matrices 5% (panel a), 6% (panel b), 7% (panel c), and COLLATAPE® (panel d) with addition of rhPDGF-BB in the culture medium at final concentration of 30 ng/ml.
Figure 15B:
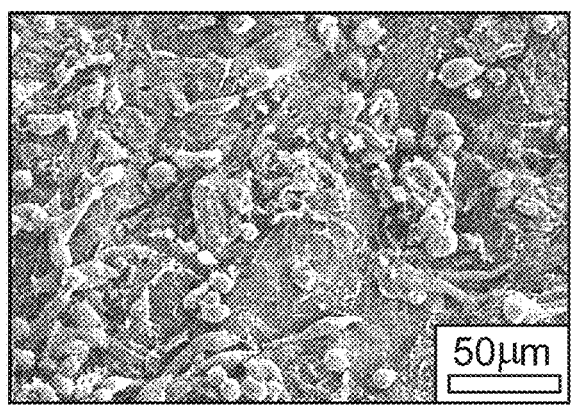
Figure 15C:
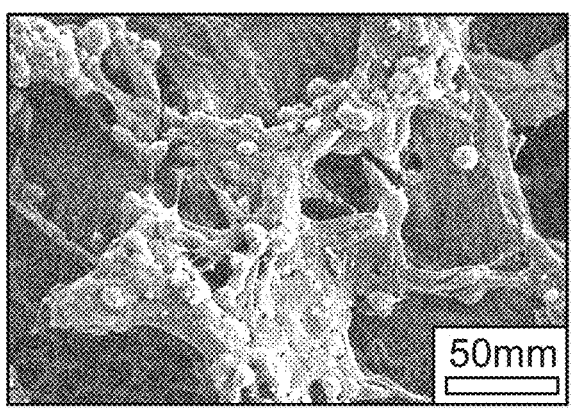
Figure 15D:
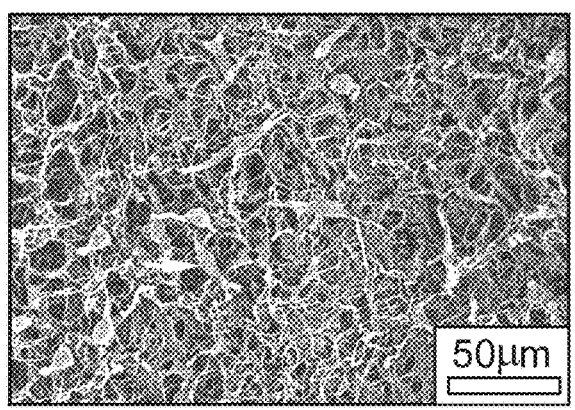

Using aseptic technique, 8-mm disks are punched from each of the BIOBLANKET™ and COLLATAPE® sheets with a biopsy punch. A syringe needle is used to gently impale one BIOBLANKET™ and COLLATAPE® disk on a 27 G1¼ needle and connect the needle with 1 mL syringe head which is installed in a specially designed chamber. 50 µl of PDGF-BB (1.0 mg/mL in 20 mM sodium acetate buffer) is applied to each disk. The disks are then incubated at room temperature for 10 minutes. One end of the silicon tubing to the arthroscopic cannular device and the other end of the tubing to 20 ml syringe are connected as shown in FIG. 14. 20 ml elution buffer (EME+2% PBS) is filled into the syringe, and the silicon tubing to the Varistaltic pump is assembled. The collagen pad saturated with rhPDGF-BB is loaded to the top the arthroscopic cannular device. The flow rate at 200 ml/min (precalibrated) is set up. Pump turns on and runs for 5 minutes. For the control, 50 µl of rhPDGF-BB is added at 1.0 mg/ml to the system from the top of arthroscopic cannular device. After 5 minutes of flushing, collect the elution buffer in a 50 ml conical tube by disconnect the silicon tubing from the 20 ml syringe while the pump still runs. The samples are stored at 2-4° C. for analysis. The amount of rhPDGF-BB eluted in each sample is measured using the DuoSet ELISA kit from R & D systems, as described in ELISA Assay Procedure below.

ELISA Assay Procedure

The capture reagent is diluted to the working concentration (0.4 µg/ml) in DPBS by adding 56 µl of capture reagent stock solution to 10 ml DPBS, 100 µl of diluted capture reagent is then added to each well of a 96-well plate. The plate is sealed with plate sealer, and incubated at room temperature overnight on a shaker. The bubbles from the Aspiration and dispensing manifold are drained and plates are washed three times with wash buffer. 200 µl of Elution Buffer are added to each well and plates are blocked for at 2 hours (maximum 4 hours) at room temperature with rocking. Plates are washed three times with wash buffer.

Steptavidin-HRP is diluted to the working concentration (200× dilution) in Reagent Diluent Buffer by adding 50 µl of Streptavidin-HRP stock solution to 10 ml Reagent Diluent Buffer. The Steptavidin-HRP is then added in 100 µl to each well and covered with aluminum foil, and incubated for 20 minutes at room temperature on orbital shaker. Immediately after adding Streptavidin-HRP to plate, needed volume of SureBlue TMB is then aliquoted into a 15 ml conical tube wrapped in foil and placed on bench to allow equilibration to room temperature. Separate tube for each plate is prepared. Plates are then washed three times with wash buffer.

Sure Blue is added in 100 µl to each well, covered with aluminum foil, and incubated 20 minutes at room temperature. 50 µl IN HCL are then added to each well to stop the reaction. The optical density at 450 nm are read with a correction set at 540 nm within 30 minutes after the reaction is topped.

Data Calculation

Standards using the 4-Parameter graph are plotted, and rhPDGF-BB concentration for each test sample at each dilution using the standard curve on each plate is calculated. Mean values and standard deviations (SD) for each of the triplicate samples from the two dilutions at each time point is also calculated.

The total rhPDGF-BB present in each sample is determined by multiplying rhPDGF-BB concentration with the total volume of each sample. The cumulative amount of rhPDGF-BB in each sample at each time point is calculated by summing the amount of rhPDGF-BB at that time point to the previous time point.

Mean+/−SD for cumulative amount of rhPDGF-BB released at each of the four time points is plotted. The percentage of rhPDGF-BB release in each sample is calculated by dividing the cumulative rhPDGF-BB release at each time point with the mean value of control at the same time point. The mean values of percentage of rhPDGF-BB release for each of the triplicate samples at each time point are also calculated. The mean+/−SD for percentage of rhPDGF-BB release at each of the four time points is plotted.

Statistical Analysis

Statistical comparisons of data at each time point are done by an appropriate method according to the data distribution.

Example 11: Characterization of Release, Stability, and Biopotency of Recombinant Human Platelet-Derived Growth Factor-BB (rhPDGF-BB) Combined with Collagen Matrices Using a BenchTop Model of Arthroscopic Irrigation This study was conducted to develop a novel Bench Top Arthroscopic Model to replicate the high fluid flow arthroscopic environment, and to characterize the release, stability, and biopotency of rhPDGF-BB, eluted from four different collagen matrices considered for application in tendon to bone attachment procedures, such as anterior cruciate ligament reconstruction procedure or rotator cuff injuries treatment procedure.

Methods

Four Type I bovine collagen matrices were evaluated: three dermally derived, collagen matrices of differing collagen concentrations (A=4.5% collagen; B=5% collagen, C=6% collagen from Kensey Nash Corporation) and one Achilles tendon derived matrix (collagen D, COLLATAPE®) from Integra LifeSciences). All matrices were punched into 8 mm discs. To assess the release of rhPDGF-BB (Novartis), from the collagen matrices, each disc was hydrated with 50 µl of rhPDGF-BB at 1 mg/ml (50 µg), incubated for 10 min at room temperature, loaded into the Bench Top Arthroscopic system (see FIG. 14) prefilled with 20 ml of elution buffer (MEM containing 2% PBS), and flushed for 5 min at 200 ml/min flow rate. The same amount of rhPDGF-BB was added to the system as a control. Elution buffer samples used to wash the matrices were analyzed using a DuoSet ELISA assay (R & D Systems). Reversed phase and size exclusion high performance liquid chromatography (HPLC) was used to derive profiles of rhPDGF-BB released from the collagen matrices for assessment of changes/modification in the native/denatured structure of rhPDGF-BB. The biopotency of rhPDGF-BB released from the collagen matrices was tested using a bromodeoxyuridine (BrdU) cell proliferation assay (Promega). NIH3T3 fibroblasts were cultured in releasate containing rhPDGF-BB (0-0.24 µg/ml), BrdU was then added, and the cells incubated for 48 hours.

The mean percent rhPDGF-BB release, relative to control for each of the four collagen matrices was as follows: collagen A, 79%; collagen B, 64.6%; collagen C, 74.3%; and collagen D, 89.0%. Collagen D showed the greatest release of rhPDGF-BB, which was significantly greater than that observed for matrix B or C as demonstrated using a One Way Analysis of Variance Fisher LSD Method. No apparent changes to the rhPDGF-BB were found following combination with matrix D, as demonstrated by reversed phase HPLC, but mild rhPDGF-BB oxidation occurred with collagen matrices A, B, and C, however these changes did not appear to affect biopotency (as evaluated by BrdU).

This study shows that the Bench Top Arthroscopic model is an effective system to evaluate matrices for the delivery of recombinant protein therapeutics proposed for use in sports medicine arthroscopic repair/regenerative procedures. Collagens A and D released more rhPDGF-BB than did collagens B and C, and collagen D did not result in any changes to the rhPDGF-BB, exhibiting great potential for use in sports medicine regenerative procedures. Further, this arthroscopic model represents an excellent in vitro tool which allows one to tailor recombinant protein therapeutic devices to provide the optimal delivery dose for maximum effectiveness.

Example 12: Cell Migration in BIOBLANKET™ Matrices of Different Densities and COLLATAPE® in Response to rhPDGF-BB Via a Scanning Electron Microscopic (SEM) Assessment This study assessed the extent of cell migration into BIOBLANKET™ and COLLATAPE® matrices by culturing primary ovine tenocytes that are treated with or without rhPDGF-BB and subsequently assessed via scanning electron microscopic (SEM) technique.

Materials and Methods

The migration of ovine tenocytes into the BIOBLANKET™ matrices and COLLATAPE® was evaluated by seeding the matrices with a known quantity of cells and then culturing the matrices for 4 days. The matrices were then processed by critical point drying and the cell distribution and density in the matrices were assessed under scanning electron microscope.

The test materials include 1) 5%, 6%, or 7% BIOBLANKET™ (Lot # R436-1, R436-2, R436-3); 2) COLLATAPE® (Lot #1072549); 3) rhPDGF-BB (0.3 mg/ml; Lot #: BMTI204), and 4) fresh ovine foot, amputated at the ankle joint. The study design is listed in Table 11.

TABLE 11

Sample Layout

| Sample No. | Materials | Cell suspension (P+)" | | Cell suspension (P-)" | |
|---|---|---|---|---|---|
| | | Medium (P+)' | Medium (P-)d | Medium (P+) | Medium (P-) |
| 01 | 5% Collagen | | | | |
| 02 | 5% Collagen | | | | |
| 03 | 5% Collagen | | | | |
| 04 | 5% Collagen | | | | |
| 05 | 6% Collagen | | | | |
| 06 | 6% Collagen | | | | |
| 07 | 6% Collagen | | | | |
| 08 | 6% Collagen | | | | |
| 09 | 7% Collagen | | | | |
| 10 | 7% Collagen | | | | |
| II | 7% Collagen | | | | |
| 12 | 7% Collagen | | | | |

TABLE 11-continued

Sample Layout

| Sample No. | Materials | Cell suspension (P+)" | | Cell suspension (P-)" | |
|---|---|---|---|---|---|
| | | Medium (P+)' | Medium (P-)d | Medium (P+) | Medium (P-) |
| 13 | COLLATAPE ® | | | | |
| 14 | COLLATAPE ® | | | | |
| 15 | COLLATAPE ® | | | | |
| 16 | COLLATAPE ® | | | | | aSuspension (P+): the cell seeding suspension contains 1.2 mg/ml rhPDGF-BB
bSuspension (P-): the cell seeding suspension does not contain rhPDGF-BB
"Medium (P+): cell culture medium contains 30 ng/ml of rhPDGF-BB
dMedium (P-): cell culture medium does not contain rhPDGF-BB (i) Isolation and Culture of Primary Ovine Tenocytes Fresh ovine foot was cleaned, sprayed and washed using soap, water, and 70% alcohol. About 3 inch wide of skin from the surface of flexor tendon was excised. The incision was sprayed with 70% alcohol and covered with surgical drapes. An incision over the tendon sheath was made to expose the tendon. The tendon was then severed from distal side. The tendon was pulled as long as possible, and the proximal side was severed. Tendon was then placed in a 50 ml conical tube filled with ice-cold DPBS. The foot and waste tissue were discarded.

The tendon tissue was minced to small pieces in a sterile 120 mm cell culture dish in a laminar flow hood working area. The minced tissue was then transferred to a fresh 50 ml conical tube. The minced tendon tissue was washed twice with DPBS and once with DMEM/F-12 medium. Tendon tissue was then digested with 500 Units/ml Pronase protease in DMEM/F-12 medium for hour. The pronase protease was aspirated and washed twice with DPBS and once with serum-free DMEM/F-12 medium.

The tenocytes were then liberated with 0.2 collagenase P plus. 150 Units/ml DNAse-11 in serum free DMEM/F-12 medium for one hour. The digest was filtered through a 75-μm cell strainer. The tissue left was returned in the strainer to a 50 ml conical tube, and the tenocytes were liberated with 0.2% collagenase P plus 150 Units/ml DNAse-II in serum free DMEM/F-12 medium for one hour. The cells were pelleted by centrifugation at 1200-1500 RPM for 5 minutes at 4° C. The cells were resuspended in 10 ml of DMEM/F12 growth medium and a cell count was performed using Trypan blue and hemacytometer. The cells were plated in T75 or T150 flasks with DMEM/F-12 growth medium at a density between 5000-7500 cells/cm$^2$. The entire process described in this paragraph was repeated every one hour until all the tendon tissues were digested. The growth medium was changed every two days and changed to basic medium 24 hours prior to seeding the cells to the BIOBLANKET™ and COLLATAPE® matrices.

(ii) Cell Seeding and rhPDGF-BB Addition

Using sterile technique, 8 mm discs from the BIOBLANKET™ and COLLATAPE® matrices were punched using a biopsy punch. One BIOBLANKET™ or COLLATAPE® disc on each 27 G½ needle was gently impaled and the needle was bent 90 degree angle twice to an open rectangular shape to secure the disc form sliding down. The needle impaled with BIOBLANKET™ and COLLATAPE® matrices disc were connected to 1 ml syringe head in the specially designed chamber. Tenocytes were trypsinized and suspended (less than 4 passages) in 1 ml of DMEM basic medium containing 2% PBS and antibiotics at a concentration of $10^6$ cells/ml. A total amount of 60 ng (30 ng/ml in 2 ml medium) of rhPDGF-BB was loaded to each disc. BIOBLANKET™ and COLLATAPE® matrices discs were then seeded with cells and incubated in the chamber in the incubator without media immersion for 1 hour. DMEM medium containing 2% PBS was prepared and added in 2 ml to 8 wells of each 24-well ultra low attachment plate for total 8 wells as rhPDGF-BB treated group. After 1 hour incubation, the cell-seeded discs from the loading boxes were removed. By using hemostat, the needle tip from the plastic root was broken. The cell-seeded discs were transferred together with the needle tip to wells prefilled with media containing different compositions. The needle tip attached in the discs kept the disc floating in the medium, so the cells on both sides of the disc were fed evenly with nutrition. Total four treatments were conducted for each material and triplicate samples were prepared for each material and each treatment. After 12 hours' static culture in the incubator at 37° C. and 5% $CO_2$ atmosphere, the plates were placed with cell-seeded collagen matrices on an orbital shaker in the incubator. The medium containing the same compositions as the first time feeding was changed every 48 hours.

(iii) Scanning Electron Microscopic Process

After four days of culture, each cell-seeded disc from 24-well plate was transferred to a cryovial with emersion of medium. The medium from the cryovial was then removed and the samples were washed in DPBS twice. The samples were fixed in 2.5% glutaraldehyde for 2 hours. The samples were then washed in DPBS five times and post-fixed in 2% osmium tetroxide for two hours. The samples were soaked in deionized water for 10 minutes and washed five times with deionized water to remove excess osmium tetroxide. The samples were dehydrated in anascending series of ethanol and then dried in a Polaron critical point drier. The samples were coated with gold-palladium and viewed with a Hitachi SEM.

Results and Conclusions

The tenocytes were grown on the surface of all BIOBLANKET™ matrices with different concentration of collagen slurry, but grown inside the COLLATAPE® matrix. Most of the tenocytes were in round shape while growing on all BIOBLANKET™ matrices with different concentration of collagen slurry but in spindle shape on the COLLATAPE® matrix. See FIG. 15.

Example 12: Rotator Cuff Repair Using rhPDGF-BB and Type I Bovine Collagen Matrix in an Ovine Model The purpose of this study was to determine the efficacy of an rhPDGF-BB laden matrix intended to promote stronger reattachment of the infraspinatus tendon to the humerus for rotator cuff repair using an ovine model. The experimental design is provided as follows: 1) Suture only (n=9); 2) Suture+Collagen Matrix+Buffer (n=9); 3) Suture+Collagen Matrix+0.15 mg/ml (or 75 µg) rhPDGF-BB (n=9); 4) Suture+Collagen Matrix+0.30 mg/ml (or 150 µg) rhPDGF-BB (n=9); 5) Suture+Collagen Matrix+1.0 mg/ml (or 500 µg) rhPDGF-BB (n=9); and 6) iCTL (n=9) Intact Contra Lateral Control. 9 Animals from suture only, suture+Collagen Matrix+buffer, and the three dose groups were utilized for biomechanical testing, and 3 each for histology testing. The iCTL group was smaller with 6 animals for biomechanical testing and 3 for histology testing.

Surgical Procedure

The infraspinatus tendon of skeletally mature sheep (3.5+ years) was surgically exposed and sharply detached from the humeral head. The tendon footprint was decorticated and three perforations were made into the bone to induce bleeding. The test articles were placed as an interpositional graft between the tendon and the bone. Two sutures were passed through the tendon using a Mason-Allen technique and the tendon was secured to the humeral head through a single-row repair consisting of 3 bone tunnels. The surgical site was closed using standard procedure and the sheep were allowed to ambulate normally. Animals were sacrificed 12 weeks after surgery.

Materials and Methods

Biomechanical Testing

Shoulders from animals allocated for biomechanical testing were harvested and denuded of all musculature, while leaving the humerus-infraspinatus tendon construct intact. A total of 51 shoulders were biomechanically evaluated. Following cleaning, specimens were wrapped in saline soaked gauze and stored at $-20°$ C. until biomechanical testing. The humeri were potted in 2" PVC pipe using high strength poly-methyl-methacrylate (PMMA) resin. Specimens were kept hydrated during the potting preparation and biomechanical testing with a saline spray at 15 minute intervals. The potted humeri were mounted in a custom-designed testing fixture that was rigidly attached to the materials testing system loading frame (MTS MiniBionix, Edan Prairie, Minn.). A custom-designed cryoclamp which was designed to preserve the natural cross section of the infraspinatus tendon and minimize soft tissue slippage was to apply a uniaxial traction forces to the construct at an angle of approximately 135° to the potted humerus. This was done to mimic the physiological force vector of the tendon. Testing commenced when a thermocouple attached to the cryoclamp registered $-22°$ C., a temperature previously reported to be sufficient to ensure secure coupling between the tendon and clamp.

Three retroreflective markers were sutured or glued onto the potted construct: one on the humerus immediately adjacent to the repair site, one on the tendon proximal to the repair interface, and the third on the cryoclamp. Three cameras (Motion Analysis, Santa Rosa, Calif.) recorded the spatial movement of the markers at 60 Hz. Marker displacement measurements using the camera system allowed for real-time monitoring of local tissue deformation across the rotator cuff repair site.

Phase 1: 30 Cycle Dynamic Preconditioning

A cyclic loading test was initially employed to precondition the rotator cuff repair. A 10 Newton (N) preload was applied in force control for two minutes, following which the repaired construct were cyclically preconditioned in a force-control protocol from 10 to 50 N at 0.25 Hz for 60 cycles to reach a steady-state condition. Sixty (n=60) cycles was chosen based on pilot experiments in our laboratory that have demonstrated that the slope of the displacement versus time curve reaches a repeatable steady-state behavior between 50 and 60 cycles. Conditioning elongation and peak-to-peak elongation were determined during the cyclic preconditioning test. Conditioning elongation was defined as the distance in y-displacement between the 1st cyclic peak and the 60th cyclic peak. Peak-to-peak elongation was defined as the average of the local minimum to maximum of the 58th, 59th, and 60th cycles.

Phase 2: Quasi-Static Failure Loading

Following preconditioning, the repaired constructs were loaded to failure under displacement control at a rate of 1 mm/s. Biomechanical parameters of interest included ultimate load-to-failure and quasi-static stiffness (defined as the slope of the load-displacement curve). Finally, the failure mechanism was documented for each specimen. Digital images were taken as appropriate.

Statistical Analysis

A One-Way ANOVA and post-hoc Fisher's LSD and Tukey test were used to identify significant differences in continuous biomechanical parameters between treatment groups excluding the intact controls. Significance was set at $p \leq 0.05$ and all analyses were performed with SigmaStat 3.1 (Systat Software, Inc., San Jose, Calif.).

Results

Figure 16:
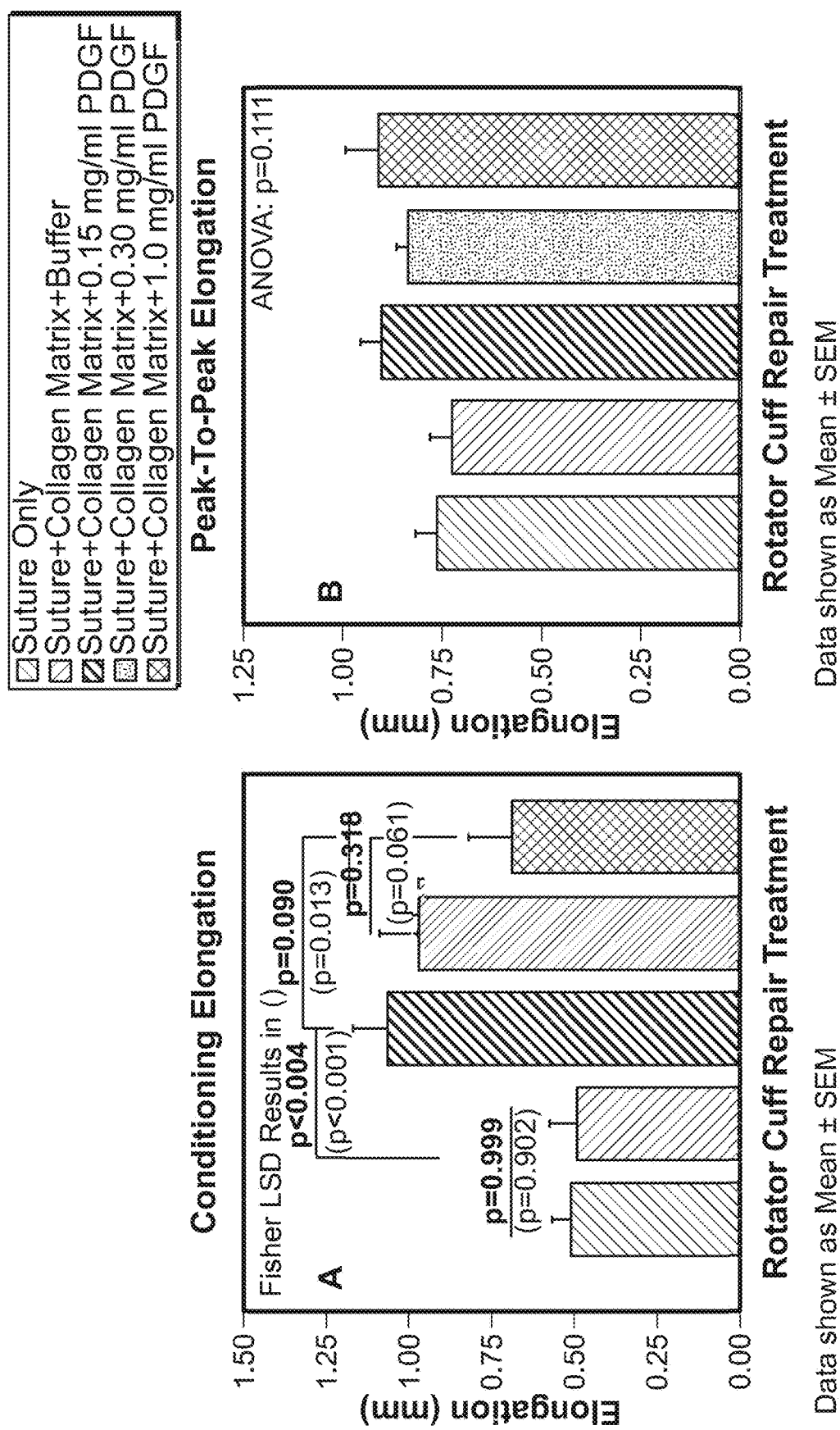
FIG. 16 shows the Dynamic Preconditioning Results of the Rotator Cuff Injury Treatment.

Raw data from the cyclic preconditioning component of testing are presented in Table 12. The 0.15 mg/ml PDGF and 0.30 mg/ml rhPDGF-BB groups underwent significantly greater conditioning elongation than the Suture Only and Suture+Collagen Matrix groups (Tukey's: $p \leq 0.024$; Fisher LSD: $p \leq 0.003$). FIG. 16A. There were no significant differences in peak-to-peak elongation between any groups ($p=0.111$, FIG. 16B).

TABLE 12

Summary Data from Cyclic Preconditioning Analysis. Data Reported as Mean ± S.E.M.

| Treatment | n | Conditioning Elongation (mm) | Peak-to-Peak Elongation (mm) |
|---|---|---|---|
| Suture Only | 9 | 0.510 ± 0.058 | 0.765 ± 0.056 |
| Suture + Collagen Matrix + Buffer | 9 | 0.492 ± 0.086 | 0.729 ± 0.055 |
| Suture + Coltagen 1'v1atiix + 0.1 5 mg/ml PDGF | 9 | 1.069 ± 0.103 | 0.908 ± 0.051 |
| Suture + Collagen Matrix + 0.30 mg/ml PDGF | 9 | 0.971 ± 0.119 | 0.841 ± 0.028 |
| Stiture + Collagє n Matrix + 1.0 mg/ml PDGF | 9 | 0.689 ± 0.133 | 0.913 ± 0.086 |
| iCTL | 6 | 0.070 ± 0.017 | 0.354 ± 0.030 |

Figure 17:
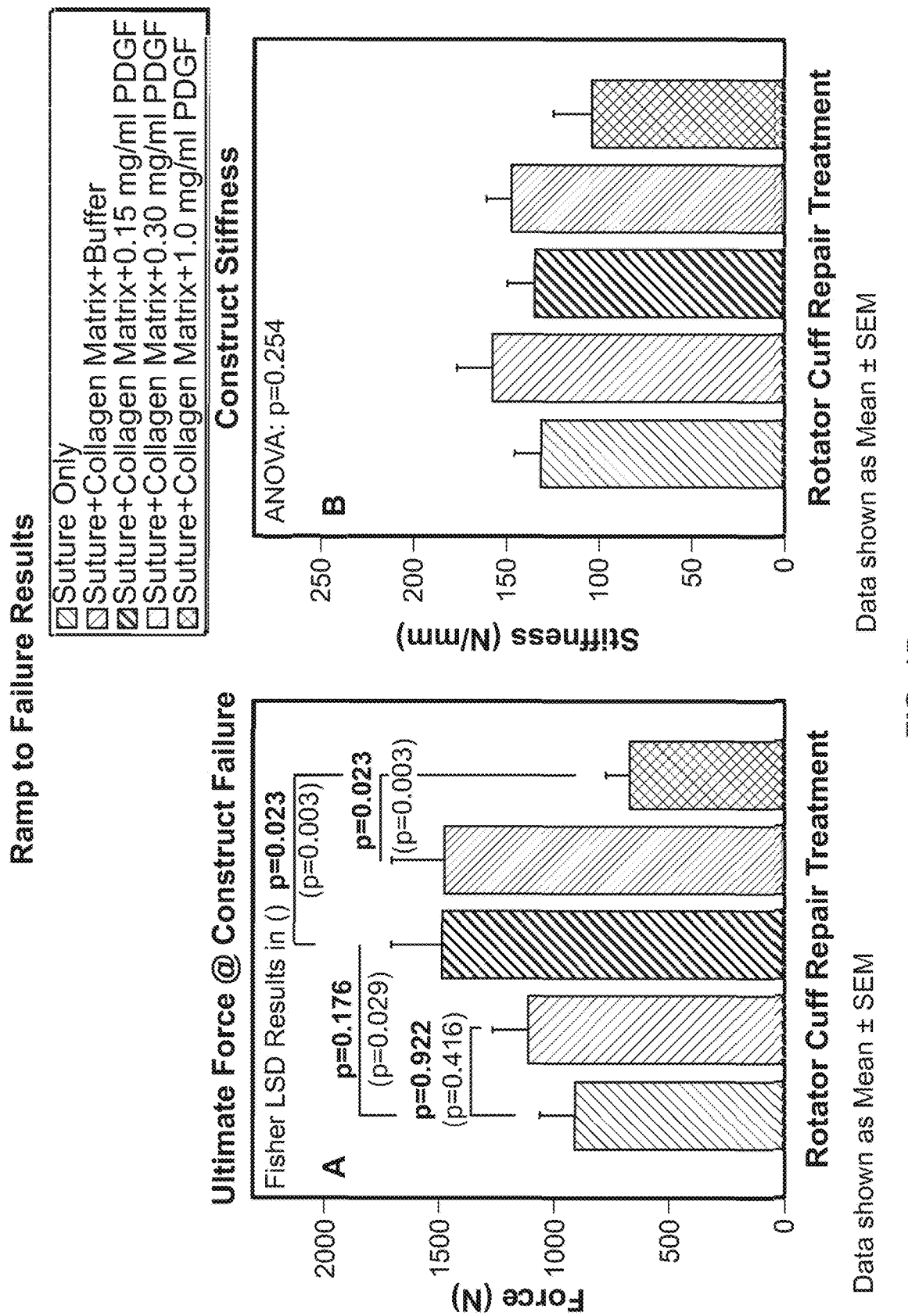
FIG. 17 shows the Ramp to Failure Results of the Rotator Cuff Injury Treatment.

Raw data from the ramp to failure component of the biomechanical testing are presented in Table 13. Repair augmentation with 0.15 mg/ml and 0.30 mg/ml rhPDGF-BB resulted in a 63.7% and 63.3% increase in load to failure relative to the Suture Only group, respectively (Tukey: $p=0.176$; Fischer LSD: $p=0.029$ and Tukey: $p=0.181$; Fisher LSD: $p=0.030$, FIG. 17A). Further, load at failure data indicated that the lower rhPDGF-BB doses of 0.15 mg/ml and 0.30 mg/ml outperformed the higher 1.0 mg/ml PDGF dose, manifested as a 120% and 119.3% increase, respectively, in load at failure ($p=0.023$ and $p=0.023$ (Fisher: $p=0.003$)). No statistical differences in construct stiffness were identified between groups ($p=0.254$, FIG. 17B). Constructs in the 0.15 mg/ml and 0.30 mg/ml rhPDGF-BB group exhibited significantly greater elongation at failure relative to the Suture Only group ($p \leq 0.018$ and $p \leq 0.024$, respectively). Fisher's LSD indicated that the 0.15 mg/ml and 0.30 mg/ml PDGF groups elongated significantly more that the Suture+Collagen Matrix Buffer group ($p=0.015$ and $p=0.011$, respectively). No differences in elongation at failure were identified between the 0.15 mg/ml, 0.30 mg/ml or 1.0 mg/ml rhPDGF-BB groups ($p \geq 0.054$).

TABLE 13

Summary Data from Ramp to Failure Testing. Data Reported as Mean ± S.E.M.

| Treatment | n | Peak Force (N) | Global Stiffness (N/mm) | Peak Elongation (mm) |
|---|---|---|---|---|
| Suture Only | 9 | 910.39 ± 156.13 | 131.41 ± 14.23 | 8.96 ± 0.62 |
| Suture + Collagen Matrix + Buffer | 9 | 1120.36 ± 157.43 | 157.33 ± 18.99 | 10.16 ± 1.01 |
| Suture + Collagen Matrix + 0.15 mg/ml PDGF | 9 | 1490.51 ± 224.51 | 134.44 ± 15.53 | 15.17 ± 0.98 |
| Suture + Collagen Matrix + 0.30 mg/ml PDGF | 9 | 1486.59 ± 228.95 | 147.47 ± 13.71 | 15.38 ± 2.35 |
| Suture + Collagen Matrix + 1.0 mg/ml PDGF | 9 | 677.75 ± 105.94 | 104.25 ± 21.36 | 11.48 ± 1.34 |
| iCTL | 6 | 4211.61 ± 229.57 | 300.31 ± 17.68 | 16.79 ± 1.30 |

For the Suture Only, Suture+Collagen Matrix+Buffer, and Suture+Collagen Matrix+1.0 mg/ml rhPDGF-BB treatment groups, construct failure in every specimen was manifested as mid-substance tissue failure at the insertion site on the humerus. No humeral avulsion failures were noted in any (n=27) of the tendons in these three groups. In contrast, failure modes in the 0.15 mg/ml rhPDGF-BB and 0.30 mg/ml rhPDGF-BB treatment groups were mixed, manifesting as either mid-substance tissue failure at the insertion site on the humerus or mid-substance tissue failure combined with some bony avulsion. Specifically, 6 of 9 (66.7%) of the shoulders in the 0.15 mg/ml rhPDGF-BB group exhibited some degree of bony avulsion while 5 of 9 (55.6%) of the shoulders in the 0.30 mg/ml rhPDGF-BB group exhibited some degree of bony avulsion. Failure of the intact, contralateral constructs was manifested as either middiaphyseal humoral fracture (n=5) or bony avulsion at the infraspinatus tendon insertion site on the humerus (n=1).

Conclusion

Augmentation of a humoral infraspinatus tendon reattachment with a 0.15 mg/ml and 0.30 mg/ml of rhPDGF improved mechanical function after three months in an ovine model relative to the Suture Only, Suture+Collagen Matrix+Buffer and Suture+Collagen Matrix+1.0 mg/ml rhPDGF-BB groups. Enhanced biomechanical integrity of the lower doses of rhPDGF-BB was manifested as a 63% increase in load to failure relative to the Suture Only group and 120% increase in load at failure relative to the 1.0 mg/ml rhPDGF-BB group. The data reported here support a dose-dependent effect on rotator cuff augmentation, with lower rhPDGF-BB doses eliciting a greater healing response relative to the higher 1.0 mg/ml dose of the growth factor. Further, failure modes in the 0.15 mg/ml rhPDGF-BB and 0.30 mg/ml rhPDGF-BB treatment groups were similar to the failure mode consistently seen in the intact, non-operated shoulders, as 6 of 9 (66.7%) of the shoulders in the 0.15 mg/ml rhPDGF-BB group exhibited some degree of bony avulsion while 5 of 9 (55.6%) of the shoulders in the 0.30 mg/ml rhPDGF-BB group exhibited some degree of bony avulsion. This finding show that the lower doses of PDGF (e.g., rhPDGF-BB) promoted greater tendinacious integration with the humoral tuberosity over the course of the 12 week healing period and that the lower doses of PDGF are more suitable for augmenting rotator cuff repairs.

Example 13: Rotator Cuff Repair Using rhPDGF-BB and a Type I Bovine Collagen Matrix in an Ovine Model: Histological Results This study was designed to assess the effectiveness of Recombinant Human Platelet-Derived Growth Factor-BB (rhPDGF-BB) in combination with a Type I Bovine Collagen matrix to promote healing and regeneration of the sheep rotator cuff insertion. Optimal healing of rotatorcuff injuries involves reinsertion of the tendon into bone at the original site of attachment (tendon "footprint"). Without reinsertion of the tendon fibers into bone, the healed site is considered "weaker" than the original attachment, potentially limiting function and leading to greater chances for re-injury. Previous studies have reported a relatively high rate of failure following rotator cuff repair (See, e.g., Boileau P., et al., *J Bone Joint Surg Am,* 87:1229-1240 (2005); Galatz L. M., et al., *J. Bone Joint Surg Am.,* 86:219-224 (2004)); Gazielly D. F., *Clin. Orthop Relat Res,* 304:43-53 (1994)); Gerber C. J. et al., *Bone Joint Surg Am,* 82:505-515 (2000); and Harryman D. T., et al., *J. Bone Joint Surg Am,* 73:982-989 (1991)), which has been postulated to result from a variety of different factors (see, e.g., Goutalier D., et al., *Clin Orthop,* 304:78-83 (1994); Gerber C. et al., *J Bone Joint Surg Br,* 76:371-380 (1994); Warner J. P., et al., *J Bone Joint Surg Am,* 74:36-45 (1992)). Tendon tissue quality and tendon-to-bone healing have been proposed as two of the most important factors contributing to failed rotator cuff repairs, and the delivery of growth factors or cells to augment tendon-to-bone healing have been suggested as methods to optimize healing of these injuries (see, e.g., Gamradt S. C., et al., *Tech in Orthop,* 22:26-33 (2007) and Dovacevic D., et al., *Clin. Orthop Relat Res,* 466:622-633 (2008)). PDGF-BB is a well characterized wound healing protein which is known to be chemotactic (cell migration) and mitogenic (cell proliferation) for cells of mesenchymal origin, including bone (osteoblast) and tendon (tenocyte) cells. Additionally, PDGF-BB has been shown to upregulate vascular endothelial growth factor (VEGF), leading to increased angiogenesis (revascularization), which is essential for successful regenerative processes. The purpose of this study was to determine efficacy of rhPDGF-BB, combined with a Type I Bovine Collagen matrix, at the site of tendon repair to augment and improve tendon reattachment using biomechanical and histological outcome measures.

Study Design

A total of 17 skeletally mature ovine were included as part of the study. Animals underwent surgical detachment followed by immediate reattachment of the right infraspinatus tendon, to the humeral greater tuberosity, using sutures through bone tunnels. In the first set of experiment, the experimental animals (n=3) received a type I collagen carrier combined with rhPDGF-BB with concentrations of 0.15 (n=3) or 0.3 (n=3) mg/ml in 20 mM sodium acetate (Acetate) buffer at the tendon-bone interface. Survival time for all animals was 12 weeks. Treatment allocations are presented in Table 14.

TABLE 14

Specimens allocated for histology

| Treatment Group | Animals (n) | Survival Time (weeks) | rhPDGF-BB Dose | Endpoint |
|---|---|---|---|---|
| Suture + Collagen Matrix + 0.15 mg/ml rhPDGF-BB | 3 | 12 | 0.15 mg/ml | Histology |
| Suture + Collagen Matrix + 0.3 mg/ml rhPDGF-BB | 3 | 12 | 0.3 mg/mL | Histology |

In the second set of experiment, the experimental animals (n=3/group) received a type I collagen carrier (collagen matrix) combined with rhPDGF-BB with concentration of 1.0 mg/mL or collagen matrix alone in 20 mM sodium acetate (Acetate) buffer at the tendon-bone interface. Table 15.

TABLE 15

Specimens Allocated for Histological Evaluation

| Treatment | Sample Size |
|---|---|
| Suture Only | n = 3 |
| Suture + Collagen Matrix + Acetate Buffer | n = 3 |
| Suture + Collagen Matrix + rhPDGF-BB (1.0 mg/mL) | n = 3 |
| Intact Control | n = 2 |
| Total Number of Specimens for Histology | n = 11 |

Tissue Harvest and Trimming

Animals were humanely euthanized after 12 weeks of healing and operated (right) shoulders were harvested and placed in 10% neutral buffered formalin for histological processing. Each shoulder was bisected through the infraspinatus tendon and its humeral attachment site into cranial and caudal halves using a scalpel for the tendon and a diamond blade saw for the humerus (Exakt Technologies, Oklahoma City, Okla.). Digital images were taken of each specimen during trimming. One half (either the cranial or caudal aspect) was processed for decalcified histology; the other half was processed for undecalcified histological analysis.

Decalcified Histological Processing

Either the cranial or caudal aspect was processed for decalcified histology and embedded in paraffin. The specimens were fixed, decalcified, dehydrated, cleared, infiltrated, and embedded using standard paraffin histology techniques and equipment (Sakura Tissue TEK V.I.P. Processor, Sakura Finetek USA, Inc., Torrance, Calif. and Shandon Histocentre 2, Thermo Shandon, Inc, Pittsburgh, Pa.). The paraffin blocks were faced and approximately 8 μm sections cut on a Shandon Finesse rotary microtome (Thermo Shandon, Inc, Pittsburgh, Pa.). Five histological sections were obtained from each shoulder at spatial thickness increments of approximately 250 microns. High-resolution digital images were acquired field by field for the entire stained slide and regions of interest using an Image Pro Imaging system (Media Cybernetics, Silver Spring, Md.), a Nikon E800 microscope (AG Heinze, Lake Forest, Calif.), and a Spot digital camera (Diagnostic Instruments, Sterling Heights, Mich.), and a Pentium IBM-based computer with expanded memory capabilities (Dell Computer Corp., Round Rock, Tex.).

Semi-Quantitative Histopathology

All tissue sections were graded according to a grading scale to assess the degree of tendon retraction (if any), evaluation of the reparative/healing tissue, the tendon bone interface, tissue response to the treatments, vascularization, inflammation, collagen orientation/fiber alignment, and interdigitation and presence of Sharpey's fibers at the insertion site. Sections were first assessed blinded to treatment and evaluated for overall healing compared to one another and given a healing score. A description of criteria for each score is presented in Table 16. The degree of tendon retraction (if any) was also measured via calibrated gross digital images using Image Pro Plus imaging system (Media Cybernetics, Silver Spring, Md.).

TABLE 16

Description of Healing Scores

| Healing Score | Description |
| --- | --- |
| High: | Majority of collagen fibers have primary alignment, higher density of collagen fibers, some Sharpey's fibers present |
| Medium: | Some collagen fibers have primary alignment, medium density of collagen fibers, some Sharpey's fibers present |
| Low: | Fewer collagen fibers have primary alignment, lower density of collagen fibers with mediocre orientation, fewer or no Sharpey's Fibers present |

Results (i)

In the first set of experiment (Collagen Matrix+0.15 mg/ml rhPDGF-BB or 0.3 mg/ml rhPDGF-BB), all operated specimens, regardless of treatment, displayed some degree of tendon retraction after 12 weeks of healing. On average, the infraspinatus tendon retracted 41.8±3.5 mm (mean±standard deviation) from the bone trough for the 0.15 mg/ml rhPDGF-BB Dose group, and 45.2±8.9 mm for the 0.3 mg/ml rhPDGF-BB Dose group.

Figure 18:
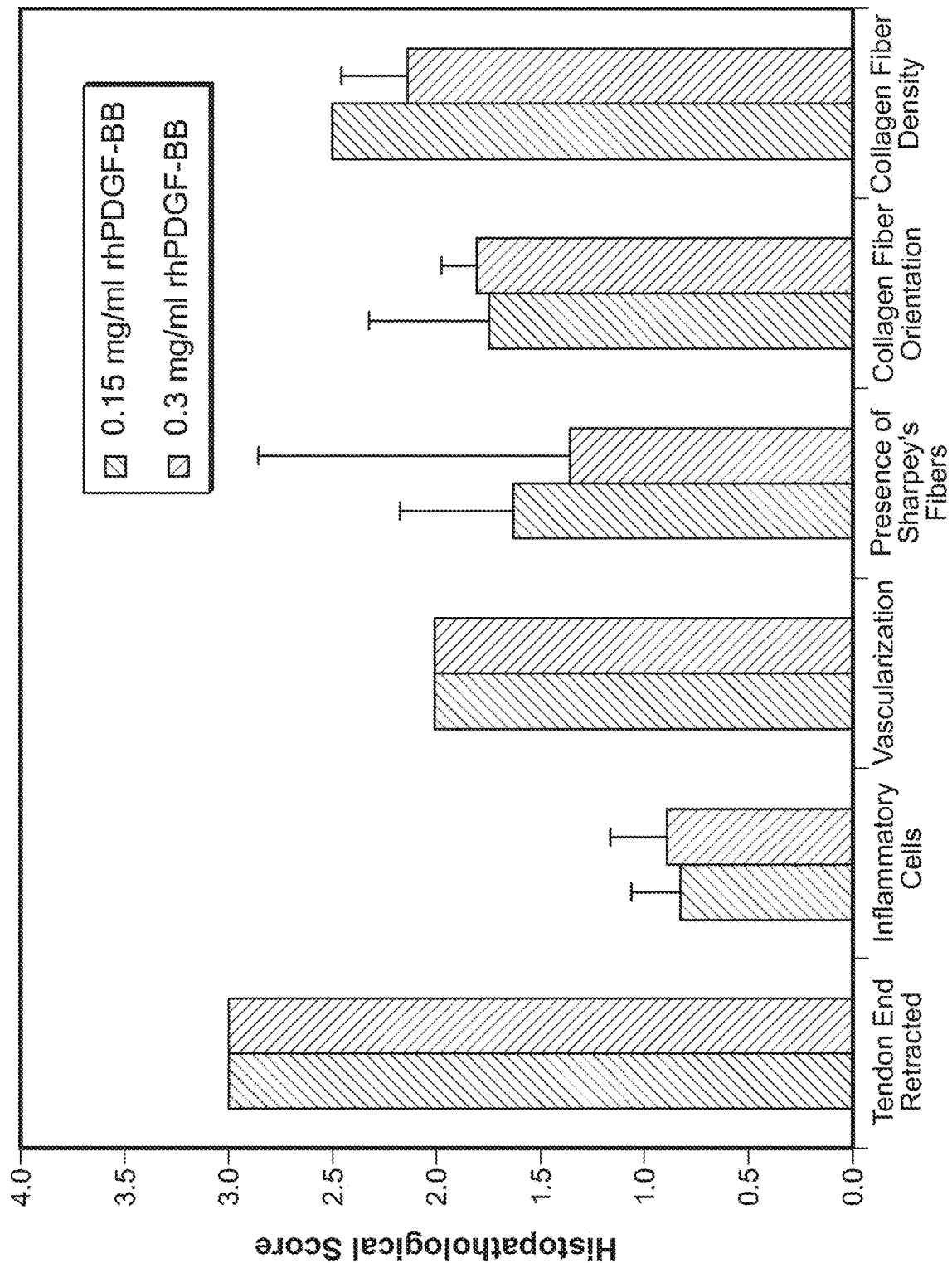
FIG. 18 is a graphical representation of histopathological scores grouped by treatment of 1) Suture+Collagen Matrix+0.15 mg/ml rhPDGF-BB or 2) Suture+Collagen Matrix+0.3 mg/ml rhPDGF-BB. Means are shown and error bars represent standard deviations.

Histopathological scores averaged by treatment in the first set of experiment are presented in Table 17; graphical representation of these results is presented in FIG. 18. The sutures were observed to be intact within the bone tunnel for 4 of the 6 specimens after 12 weeks of healing, which indicates that the failure leading to the tendon retraction occurred at the suture-tendon interface and not the bone-suture interface.

Overall, regardless of treatment, reparative tissue between the humerus and native tendon end consisted of a fibrovascular tissue (highly vascularized fibrous tissue) with active fibroplasia and moderately dense, polarizable collagen fibers present. No differences in fibroblast density were observed between treatments. All specimens displayed primary collagen fiber alignment parallel to that of the original tendon with pockets of less organized fibers. Average collagen fiber orientation and fiber density was similar between treatments.

TABLE 17

Histopathological Scores Grouped by Treatment and Averaged

| Treatment | | Tendon End Position 1 = Tendon attached to humerus 2 = Tendon slightly retracted 3 = Tendon fully retracted | Inflammatory Cells 0 = None 1 = Some 2 = Many | Vascularization 0 = None 1 = Some 2 = Abundant | Bone-Tendon Interface (Interdigitation/Sharpey's Fibers between tendon and bone) 0 = 0% Tendon-Bone attachment Area Integrated 1 = 25% Tendon-Bone attachment Area Integrated 2 = 50% Tendon-Bone attachment Area Integrated 3 = 75% Tendon-Bone attachment Area Integrated | Collagen Fiber Orientation 0 = None 1 = Some 2 = Mostly 3 = Completely | Collagen Fiber Density 1 = Low 2 = Med 3 = High |
| --- | --- | --- | --- | --- | --- | --- | --- |
| 0.15 mg/ml rhPDGF-BB | Average | 3.0 | 0.8 | 2.0 | 1.6 | 1.7 | 2.5 |
| | StDev | 0.0 | 0.2 | 0.0 | 0.5 | 0.6 | 0.0 |
| 0.3 mg/ml rhPDGF-BB | Average | 3.0 | 0.9 | 2.0 | 1.4 | 1.8 | 2.1 |
| | StDev | 0.0 | 0.3 | 0.0 | 1.5 | 0.2 | 0.3 |

At the regenerating insertion sites collagenous Sharpey's fibers of the reparative tendon tissue inserting and interdigitating either directly with bone collagen or through a layer of fibrocartilage were observed for all specimens. On average, interdigitation was observed over approximately 30-40% of the total decorticated bone surface, and this observation was consistent across all treatment groups. The Sharpey fibers observed in the operated specimens were more immature than the intact control; however, there was insertion and continuity of these regenerative fibers with the collagen of the underlying bone. In a few cases a portion of the original native tendon attachment site was observed in the operated shoulders.

Previous osteoclastic resorption of the bone surface was observed in most specimens in the decorticated region of the original attachment site. It was recognized by the scalloped surface of the bone (Howship's lacunae) where osteoclasts were no longer present or a scalloped basophilic reversal line where the surface had been covered by new bone tissue. Typically, the regions of previous resorption were covered with a layer of reactive woven bone with osteoblasts present. The reactive bone often had Sharpey fiber insertion. Resorption extent was variable. It was found over approximately 10-50% of the total bone surface regardless of treatment, and was typically covered by new woven bone. Islands of reactive woven bone and/or fibrocartilage were occasionally observed within the reparative tissue.

In all specimens, mild foreign body inflammation was observed within the healing tissue and concentrated mainly near the suture material. In a few cases, small pockets of mononuclear inflammation were observed within the reparative tissue, possibly associated with vascularization or focally damaged tissue. Inflammation was mainly mononuclear with multi-nucleated giant cells. No neutrophils were typically observed. Abundant vascularization was observed in the healing tissue in all specimens regardless of treatment. Angioblastic proliferation, indicating new vessel production, was also observed in a few specimens and was not correlated with a specific treatment. This proliferation was most probably due to the ongoing adaptational changes associated with the healing process.

Fatty infiltration is known to be one consequence of rotator cuff tendon tears, and has been shown to correlate with the degree of tendon retraction (Nakagaki et al, *J. Clin Orth Rel Res* (2008) and Bjorkenheim J. M., et al, *Acta Orthop Scand.* 60(4):461-3(1989). Fatty infiltration was observed in a few specimens in the peripheral tissue adjacent to the muscle. This was only observed in the center of the reparative tissue in one specimen (0.3 mg/ml rhPDGF-BB Dose).

(ii)

In the second set of experiment (Suture, Suture+collagen Matrix+Acetate Buffer, Suture+Collagen Matrix+rhPDGF-BB, or intact Control), the infraspinatus tendon retracted 28.1±2.8 mm from the bone trough for the Suture Only group, 39.0±4.6 mm for the Suture+Collagen Matrix+Acetate Buffer group, and 40.9±8.3 mm for the Suture+Collagen Matrix+rhPDGF-BB group.

The sutures were intact within the bone tunnel for all specimens after 12 weeks of healing which indicates that the failure leading to the tendon retraction occurred at the suture-tendon interface and not the bone-suture interface. Healing within and between treatments was variable. Healing for the Suture Only group was the most variable, with specimens ranging from the best healing to the worst healing of the groups. Suture+Collagen Matrix+Acetate Buffer specimens ranged in grading from medium/high to medium/low healing, and Suture+Collagen Matrix+rhPDGF-BB specimens ranged from medium/low to low healing. The treatment itself was not visible in any of the stained histological slides. Healing scores for all specimens arranged best healing to worst healing of the groups are shown in Table 18.

TABLE 18

Healing Scores for Individual Specimens

| specimen | Treatment | Healing Score |
|---|---|---|
| BS32 | Suture Only | High |
| BS12 | Suture + Collagen Matrix + Acetate Buffer | Medium/High |
| BS11 | Suture Only | Medium |
| BS13 | Suture + Collagen Matrix + Acetate Buffer | Medium |
| BS9 | Suture + Collagen Matrix + rhPGDF-BB | Medium/Low |
| BS24 | Suture + Collagen Matrix + Acetate Buffer | Medium/Low |
| BS30 | Suture + Collagen Matrix + rhPGDF-BB | Medium/Low |
| BS19 | Suture + Collagen Matrix + rhPGDF-BB | Low |
| BS6 | Suture Only | Low |

Figure 19:
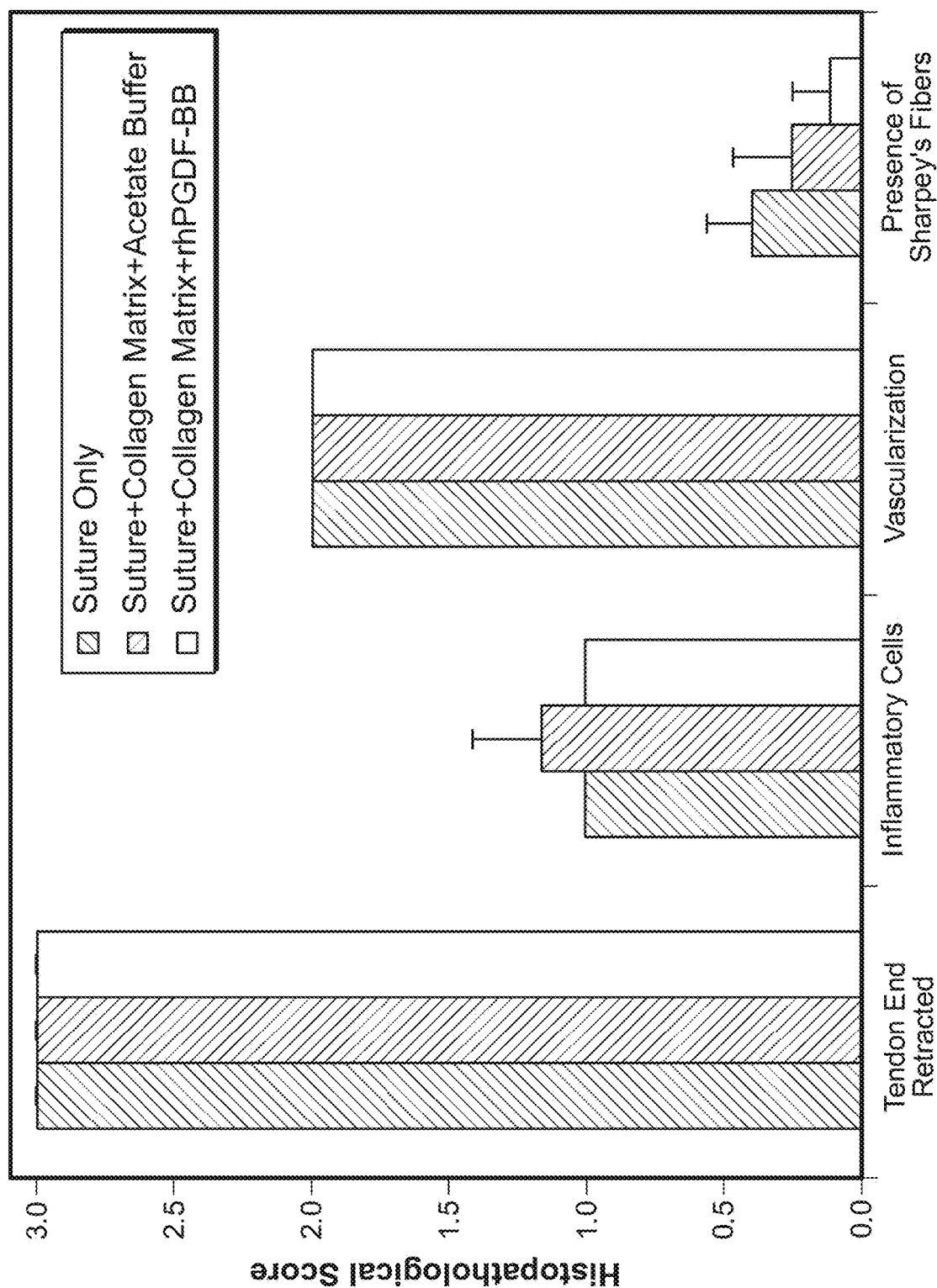
FIG. 19 is a graphical representation of histopathological scores grouped by treatment of 1) Suture only; 2) Suture+Collagen Matrix acetate buffer or 3) Suture+Collagen Matrix+1.0 mg/ml rhPDGF-BB. Means are shown and error bars represent standard deviations.

Histopathological scores averaged by treatment are presented in Table 19 and FIG. 19 Overall, regardless of treatment, reparative tissue between the humerus and native tendon end consisted of a fibrovascular tissue (highly vascularized fibrous tissue) with active fibroplasia and polarizable collagen fibers present. No differences in fibroblast density were observed between treatments. Some specimens had regions of primary collagen fiber alignment (with collagen alignment parallel to that of the original tendon) and others did not; most specimens had regions of both organized and unorganized collagen fiber alignment. In general, collagen alignment was better near the bone surface rather than near the retracted tendon end.

TABLE 19

Histopathological Scores Grouped by Treatment and Averaged

| Treatment | | Tendon End Position<br>1 = Tendon attached to humerus<br>2 = Tendon slightly retracted<br>3 = Tendon fully retracted | Inflammatory Cells<br>0 = None<br>1 = Some<br>2 = Many | Vascularization<br>0 = None<br>1 = Some<br>2 = Abundant | Bone-Tendon Interface<br>(Interdigitation/Sharpey's Fibers between tendon and bone, increments of 0.25)<br>0 = 0% Tendon-Bone attachment Area Integrated<br>1 = 25% Tendon-Bone attachment Area Integrated<br>2 = 50% Tendon-Bone attachment Area Integrated<br>3 = 75% Tendon-Bone attachment Area Integrated<br>4 = 100% Tendon-Bone attachment |
|---|---|---|---|---|---|
| Suture Only | Average | 3 | 1 | 2 | 0.4 |
| | StDev | 0 | 0 | 0 | 0.2 |
| Suture + Collagen Matrix + Acetate Buffer | Average | 3 | 1.2 | 2 | 0.3 |
| | StDev | 0 | 0.2 | 0 | 0.2 |
| Suture + Collagen Matrix + rhPGDf.-BB | Average | 3 | 1 | 2 | 0.1 |
| | StDev | 0 | 0 | 0 | 0.1 |

In general, the collagenous Sharpey fibers of the tendon at its insertion and their interdigitation with bone collagen through a layer of fibrocartilage were observed, but in very small regions; Interdigitation was usually observed over less than 10% of the total bone attachment surface. Small regions of Sharpey fiber insertion were observed in all three Suture Only (alone) specimens, in two of the Suture+Collagen Matrix+Acetate Buffer specimens, and in all Suture+Collagen Matrix+rhPDGF-BB specimens. In a few cases a portion of the original native tendon attachment site was observed in the operated shoulders.

Osteoclastic resorption of the bone surface was observed in most specimens in the decorticated region of the original attachment site. It was recognized by the scalloped surface of the bone (Howship's lacunae) where osteoclasts were no longer present or the surface had been covered by other tissue. Resorption occurred over approximately 10-20% of the total bone surface regardless of treatment. Reactive woven bone and/or fibrocartilage was observed within the reparative tissue and at the surface of the bone in all three Suture Only specimens and one Suture+Collagen Matrix+Acetate Buffer specimen.

In all specimens, mild foreign body inflammation was observed within the healing tissue concentrated mainly near the suture material. In a few cases, small pockets of mononuclear inflammation were observed within the reparative tissue, possibly associated with focally damaged tissue. Inflammation was mainly mononuclear with multi-nucleated giant cells. Generally, no neutrophils were observed. Abundant vascularization was observed in the healing tissue in all specimens regardless of treatment. Angioblast proliferation, indicating new vessel production, was also observed in a few specimens regardless of treatment and probably represented ongoing adaptational changes in the healing process.

Conclusion

Augmentation of a humural infraspinatus tendon reattachment with an rhPDGF-BB soaked collagen matrix did not prevent failure at the suture-tissue interface. The tendon was retracted from the humerus and replaced by reparative fibrovascular tissue in all specimens after 12 weeks of healing, which suggests that retraction occurred within the first several weeks postoperatively.

Figure 20A:
FIGS. 20A-20B show regions of interdigitation of tendon collagen (box) with bone at the fibrocartilage interface (arrows). A: suture+collagen matrix, 20×. B: suture+collagen matrix+0.3 mg/ml (or 150 μg) rhPDGF-BB, 20×.
Figure 20B:
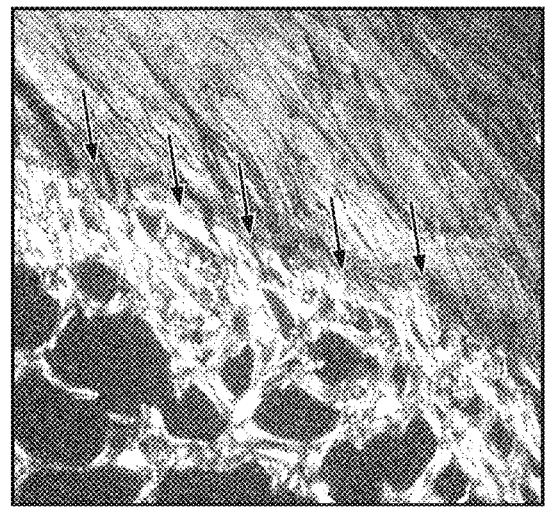

Specimens exhibited varying degrees of new bone formation, inflammation, vascularity, and Sharpey's fiber's inserting the tendon to the bone at the insertion site. No differences were noted in the suture only, suture+collagen, and suture+collagen+1.0 mg/mlrhPDGF-BB groups in the assessment of tendon retraction, inflammatory cells, vascularization, or Sharpey's fibers. Histologic sections of the Suture+Collagen Matrix+0.15 mg/ml rhPDGF-BB and Suture+Collagen Matrix+0.3 mg/ml rhPDGF-BB groups displayed increased tendon repair and interdigitation of tendon collagen with that of bone at the fibrocartilage interface. FIGS. 20A and 20B.

Unless defined otherwise, the meanings of all technical and scientific terms used herein are those commonly understood by one of skill in the art to which this invention belongs. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

The invention claimed is:

1. A method for treatment of a tendon injury or a ligament injury not involving a bone in an individual comprising:
   a) administering to an affected site of the injury of the individual an effective amount of a composition comprising: a biocompatible matrix and platelet-derived growth factor (PDGF), wherein the PDGF is present as a solution comprising PDGF, the concentration of PDGF in the solution is about 0.1 mg/ml to about 2.0 mg/ml, the biocompatible matrix comprises pores, the biocompatible matrix has a porosity of at least about 80%, and at least about 50% of the PDGF is released within about 24 hours after administration; and
   b) mechanically stabilizing the tendon by suturing the tendon or ligament with sutures, wherein the sutures comprise PDGF.

2. The method of claim 1, wherein the biocompatible matrix has a porosity of at least about 85%.

3. The method of claim 1, wherein the biocompatible matrix has a porosity of at least about 90%.

4. The method of claim 1, wherein the biocompatible matrix has a porosity of at least about 92%.

5. The method of claim 1, wherein the biocompatible matrix has a porosity of at least about 95%.

6. The method of claim 1, wherein the pores have an average area ranging from about 2500 $\mu m^2$ to about 20,000 $\mu m^2$.

7. The method of claim 1, wherein the pores have an average perimeter ranging from about 200 $\mu m$ to about 600 $\mu m$.

8. The method of claim 1, wherein the pores have diameters ranging from about 1 $\mu m$ to about 1 mm.

9. The method of claim 8, wherein the pores have diameters at least about 5 $\mu m$.

10. The method of claim 1, wherein the pores are interconnected pores.

11. The method of claim 1, wherein at least about 60% of the PDGF is released within about 24 hours.

12. The method of claim 1, wherein at least about 70% of the PDGF is released within about 24 hours.

13. The method of claim 1, wherein at least about 80% of the PDGF is released within about 24 hours.

14. The method of claim 1, wherein the biocompatible matrix is resorbed within about 21 days of in vivo administration.

15. The method of claim 1, wherein the biocompatible matrix is resorbed within about 18 days of in vivo administration.

16. The method of claim 1, wherein the biocompatible matrix is resorbed within about 15 days of in vivo administration.

17. The method of claim 1, wherein the biocompatible matrix comprises collagen.

18. The method of claim 17, wherein the collagen is soluble.

19. The method of claim 17, wherein the collagen is cross-linked.

20. The method of claim 17, wherein the biocompatible matrix further comprises a glycosaminoglycan.

21. The method of claim 20, wherein the glycosaminoglycan is chondroitin sulfate.

22. The method of claim 1, wherein the composition is a gel, particle, powder, sheet, pad, paste, patch, or sponge.

23. The method of claim 1, wherein the composition is flowable.

24. The method of claim 1, wherein the concentration of PDGF in the solution is about 0.1 mg/ml to about 0.4 mg/ml.

25. The method of claim 1, wherein the concentration of PDGF in the solution is about 0.9 mg/ml to about 1.5 mg/ml.

26. The method of claim 1, wherein cells infiltrate the composition within about 4 days after exposure to the composition.

27. The method of claim 23, wherein the step of administering comprises administering to the affected site of the injury of said individual the effective amount of the composition using a syringe.

28. The method of claim 1, wherein the tendon is selected from the group consisting of patellar tendon, anterior tibialis tendon, Achilles tendon, Hamstring tendon, semitendinosus tendon, gracilis tendon, abductor tendon, adductor tendon, supraspinatus tendon, infraspinatus tendon, subscapularis tendon, tere minor tendon, flexor tendon, rectus femoris tendon, tibialis posterior tendon, and quadriceps femoris tendon.

29. The method of claim 1, wherein the ligament is selected from the group consisting of anterior cruciate ligament, lateral collateral ligament, posterior cruciate ligament, medial collateral ligament, cranial cruciate ligament, caudal cruciate ligament, cricothyroid ligament, periodontal ligament, suspensory ligament of the lens, anterior sacroiliac ligament, posterior sacroiliac ligament, sacrotuberous ligament, sacrospinous ligament, inferior pubic ligament, superior pubic ligament, suspensory ligament, palmar radiocarpal ligament, dorsal radiocarpal ligament, ulnar collateral ligament, and radial collateral ligament.

30. The method of claim 1, wherein the tendon or ligament injury is tendon or ligament rupture, severance, tearing, delamination, strain, or deformation.

31. The method of claim 1, wherein the sutured tendon or ligament is positioned such that the ends of the injured ligament are substantially re-approximated.

32. The method of claim 1, wherein the sutures are coated with the PDGF or soaked with a solution comprising the PDGF.

33. The method of claim 32, wherein the solution has a PDGF concentration ranging from about 5 mg/mL to about 20 mg/mL.

34. The method of claim 32, wherein the sutures are resorbable.

* * * * *